US010788499B2

(12) United States Patent
Gelb et al.

(10) Patent No.: US 10,788,499 B2
(45) Date of Patent: Sep. 29, 2020

(54) METHODS FOR ASSAYING PALMITOYL PROTEIN THIOESTERASE 1 AND TRIPEPTIDYL PEPTIDASE ACTIVITY IN DRIED BLOOD SPOTS FOR DETECTION OF NEURONAL CEROID LIPOFUSCINOSES IN NEWBORNS

(71) Applicant: University of Washington, Seattle, WA (US)

(72) Inventors: Michael H. Gelb, Seattle, WA (US); Frantisek Turecek, Seattle, WA (US)

(73) Assignee: University of Washington, Seattle, WA (US)

( * ) Notice: Subject to any disclaimer, the term of this patent is extended or adjusted under 35 U.S.C. 154(b) by 220 days.

(21) Appl. No.: 15/744,736

(22) PCT Filed: Jul. 13, 2016

(86) PCT No.: PCT/US2016/042143
§ 371 (c)(1),
(2) Date: Jan. 12, 2018

(87) PCT Pub. No.: WO2017/011582
PCT Pub. Date: Jan. 19, 2017

(65) Prior Publication Data
US 2018/0209989 A1 Jul. 26, 2018

Related U.S. Application Data

(60) Provisional application No. 62/191,942, filed on Jul. 13, 2015.

(51) Int. Cl.
| | | |
|---|---|---|
| C07K 5/00 | (2006.01) | |
| C07K 5/08 | (2006.01) | |
| G01N 33/68 | (2006.01) | |
| C12Q 1/37 | (2006.01) | |
| C12N 9/48 | (2006.01) | |
| C07K 5/083 | (2006.01) | |
| C12Q 1/44 | (2006.01) | |
| G01N 33/53 | (2006.01) | |
| C07K 5/087 | (2006.01) | |

(52) U.S. Cl.
CPC .......... *G01N 33/6848* (2013.01); *C07K 5/00* (2013.01); *C07K 5/08* (2013.01); *C07K 5/0806* (2013.01); *C07K 5/0812* (2013.01); *C12N 9/48* (2013.01); *C12Q 1/37* (2013.01); *C12Q 1/44* (2013.01); *G01N 33/53* (2013.01); *C12Q 2334/20* (2013.01); *C12Q 2337/22* (2013.01); *G01N 2333/916* (2013.01); *G01N 2800/04* (2013.01); *G01N 2800/28* (2013.01)

(58) Field of Classification Search
None
See application file for complete search history.

(56) References Cited

U.S. PATENT DOCUMENTS 7,615,224 B2    11/2009 Meikle et al.

FOREIGN PATENT DOCUMENTS

| EP | 2 910 644   | * | 8/2015 |
| EP | 2 910 644 A1 |   | 8/2015 |

OTHER PUBLICATIONS

Barcenas et al. (Anal Chem. Aug. 5, 2014;86(15):7962-8) (Year: 2014).*
Chennamaneni et al. (Anal. Chem. 2014, 86, 4508-4514). (Year: 2014).*
Barcenas, M., et al., "Tandem Mass Spectrometry Assays of Palmitoyl Protein Thioesterase 1 and Tripeptidyl Peptidase Activity in Dried Blood Spots for the Detection of Neuronal Ceroid Lipofuscinoses in Newborns," Analytical Chemistry 86(15):7962-7968, Aug. 2014.
Bellizzi, J.J., III, et al., "The Crystal Structure of Palmitoyl Protein Thioesterase 1 and the Molecular Basis of Infantile Neuronal Ceroid Lipofuscinosis," Proceedings of the National Academy of Scienses of the USA (PNAS) 97(9):4573-4578, Apr. 2000.
Camp, L.A., and S.L. Hofmann, "Purification and Properties of a Palmitoyl-Protein Thioesterase That Cleaves Palmitate From H-Ras," Journal of Biological Chemistry 268(30):22566-22574, Oct. 1993.
Chang, M., et al., "Intraventricular Enzyme Replacement Improves Disease Phenotypes in a Mouse Model of Late Infantile Neuronal Ceroid Lipofuscinosi," Molecular Therapy 16(4):649-656, Apr. 2008. Chennamaneni, N.K., et al., "Improved Reagents for Newborn Screening of Mucopolysaccharidosis Types I, II, and VI by Tandem Mass Spectrometry," Analytical Chemistry 86(9):4508-4514, May 2014.
Duffey, T.A., et al., "A Tandem Mass Spectrometry Triplex Assay for the Detection of Fabry, Pompe, and Mucopolysaccharidosis-I (Hurler)," Clinical Chemistry 56(12):1854-1861, Dec. 2010.
Elbin, C.S., et al., "The Effect of Preparation, Storage and Shipping of Dried Blood Spots on the Activity of Five Lysosomal Enzymes," Clinica Chimica Acta 412(13-14):1207-1212, Jun. 2011.
Haltia, M., "The Neuronal Ceroid-Lipofuscinoses: From Past to Present," Biochimica et Biophysica Acta (BBA)—Molecular Basis of Disease 1762(10):850-856, Oct. 2006.

(Continued)

*Primary Examiner* — Sergio Coffa
(74) *Attorney, Agent, or Firm* — Christensen O'Connor Johnson Kindness PLLC

(57) ABSTRACT

The present disclosure provides assays for lysosomal enzymes, specifically palmitoyl protein thioesterase 1 (PPT1) and tripeptidyl peptidase 1 (TPP1), using, for example, tandem mass spectrometry. The assays involve the detection of enzymatic products obtained through the action of the lysosomal enzymes on new enzyme substrates, and can be used for quantitative enzyme activity measurements. The assays for the enzymes utilize a minimum steps for sample work up and can be run in a simplex format or in a duplex format for the detection of neuronal ceroid lipofuscinoses, or in a multiplex format with other mass spectrometry-based assays for screening of neuronal ceroid lipofuscinoses and other lysosomal storage disorders.

20 Claims, 19 Drawing Sheets

(56) References Cited

OTHER PUBLICATIONS

Hofmann, S., and L. Peltonen, "The Neuronal Ceroid Lipofuscinoses," in C.R. Beaudet et al. (eds.), "The Metabolic and Molecular Basis of Inherited Disease," 8th ed., McGraw-Hill, New York, 2001; pp. 3877-3894.

Jalanko, A., and T. Braulke, "Neuronal Ceroid Lipofuscinoses," Biochimica et Biophysica Acta (BBA)—Molecular Cell Research 1793(4):697-709, Apr. 2009.

Kohan, R., et al., "Therapeutic Approaches to the Challenge of Neuronal Ceroid Lipofuscinoses," Current Pharmaceutical Biotechnology 12(6):867-883, Jun. 2011. (Author Manuscript provided, PMCID: PMC3632406, available in PMC Apr. 22, 2013, 32 pages).

Li, Y. et al., "Direct Multiplex Assay of Lysosomal Enzymes in Dried Blood Spots for Newborn Screening," Clinical Chemistry 50(10):1785-1796, Oct. 2004.

Lin, L., and P. Lobel, "Production and Characterization of Recombinant Human CLN2 Protein for Enzyme-Replacement Therapy in Late Infantile Neuronal Ceroid Lipofuscinosis," Biochemical Journal 357(Pt. 1):49-55, Jul. 2001.

Lukacs, Z., et al., "Rapid and Simple Assay for the Determination of Tripeptidyl Peptidase and Palmitoyl Protein Thioesterase Activities in Dried Blood Spots," Clinical Chemistry 49(3):509-511, Mar. 2003.

Rijkers, D.T.S., et al., "A Convenient Solid Phase Synthesis of S-Palmitoyl Transmembrane Peptides," Tetrahedron Letters 46(19):3341-3345, May 2005.

Santavuori, P., et al., "Infantile Type of So-Called Neuronal Ceroid-Lipofuscinosis," Developmental Medicine & Child Neurology 16(5):644-653, Oct. 1974.

Scott, C.R., et al., "Identification of Infants at Risk for Developing Fabry, Pompe, or Mucopolysaccharidosis-I From Newborn Blood Spots by Tandem Mass Spectrometry," Journal of Pediatrics 163(2):498-503, Aug. 2013.

Selden, N.R., et al., "CNS Stem Cell Transplantation for Neuronal Ceroid Lipofuscinoses: Summary of Long-Term Follow-up Study Results," Neurosurgery 60 (Suppl. 1):161-162, Aug. 2013.

Sohar, I., et al., "Enzyme-Based Diagnosis of Classical Late Infantile Neuronal Ceroid Lipofuscinosis: Comparison of Tripeptidyl Peptidase I and Pepstatin-Insensitive Protease Assays," Clinical Chemistry 46(7):1005-1008, Jul. 2000.

Špáčil, Z., et al., "High-Throughput Assay of 9 Lysosomal Enzymes for Newborn Screening," Clinical Chemistry 59(3):502-511, Mar. 2013.

Špáčil, Z., et al., "Protonation Sites and Dissociation Mechanisms of t-Butylcarbamates in Tandem Mass Spectrometric Assays for Newborn Screening," Journal of Mass Spectrometry 46(10):1089-1098, Oct. 2011.

Tian, Y., et al., "Determination of the Substrate Specificity of Tripeptidyl-Peptidase I Using Combinatorial Peptide Libraries and Development of Improved Fluorogenic Substrates," Journal of Biological Chemistry 281(10):6559-6572, Mar. 2006.

Van Diggelen, O.P., et al., "A Rapid Fluorogenic Palmitoyl-Protein Thioesterase Assay: Pre- and Postnatal Diagnosis of INCL," Molecular Genetics and Metabolism 66(4):240-244, Apr. 1999.

Williams, R.E., and S.E. Mole, "New Nomenclature and Classification Scheme for the Neuronal Ceroid Lipofuscinoses," Neurology 79(2):183-191, Jul. 2012.

Wolfe, B.J., et al., "New Substrates and Enzyme Assays for the Detection of Mucopolysaccharidosis III (Sanfilippo Syndrome) Types A, B, C, and D by Tandem Mass Spectrometry," Bioconjugate Chemistry 23(3):557-564, Mar. 2012.

Wong, A.M., et al., "Current Therapies for the Soluble Lysosomal Forms of Neuronal Ceroid Lipofuscinosis," Biochemical Society Transactions 38(6):1484-1488, Dec. 2010.

Barcenas, Mariana, et al. "Tandem Mass Spectrometry Assays of Palmitoyl Protein Thioesterase 1 and Tripedptidyl Peptidase Activity in Dried Blood Spots for the Detection of Neuronal Ceroid Lipofuscinoses in Newborns." Anal. Chem., vol. 86, Jul. 14, 2014, pp. 7962-7968, dx.doi.org/10.1021/ac501994b.

PCT/US2016/042143, "International Search Report," dated Dec. 16, 2016, 4 pages.

PCT/US2016/042143, "Written Opinion of the International Searching Authority," dated Dec. 16, 2016, 7 pages.

\* cited by examiner

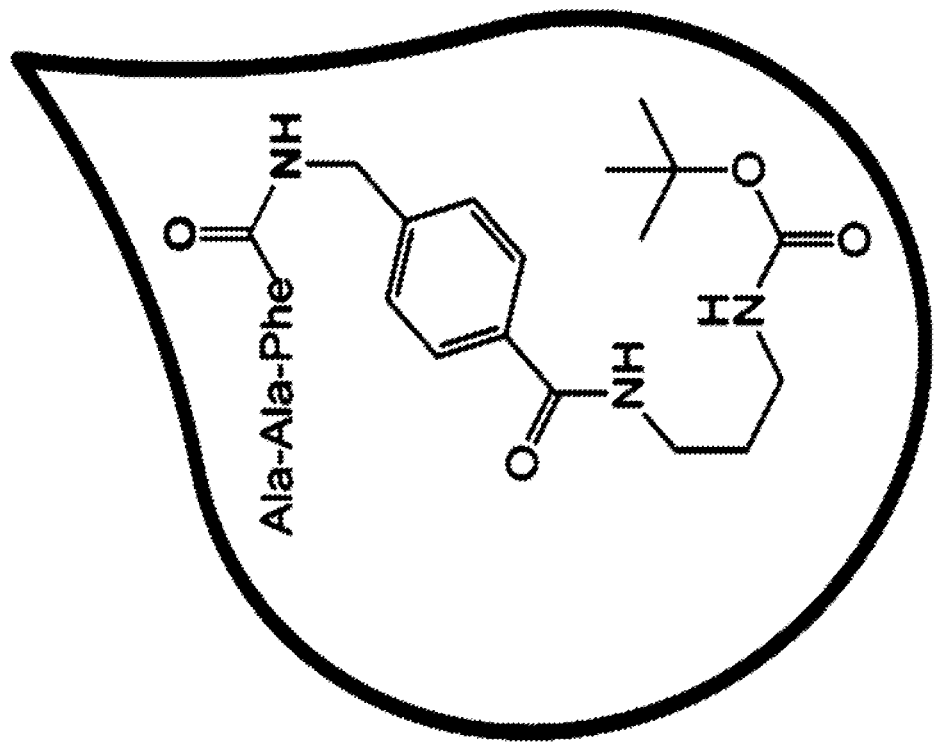
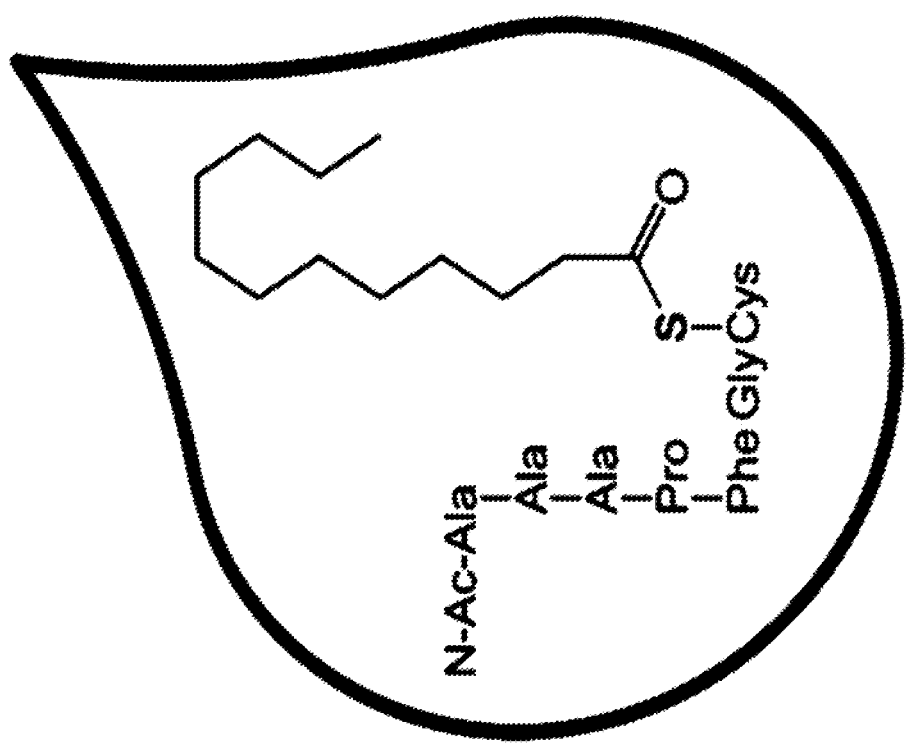
FIG. 5

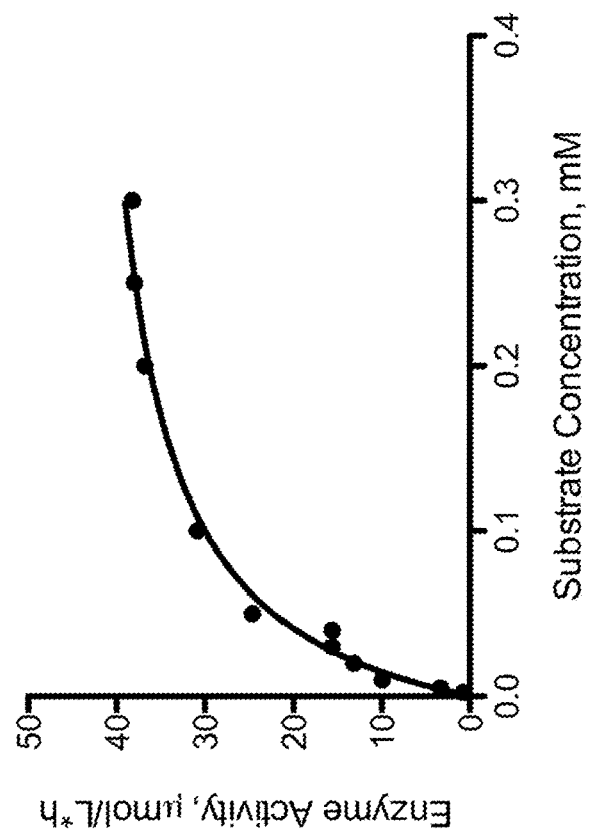
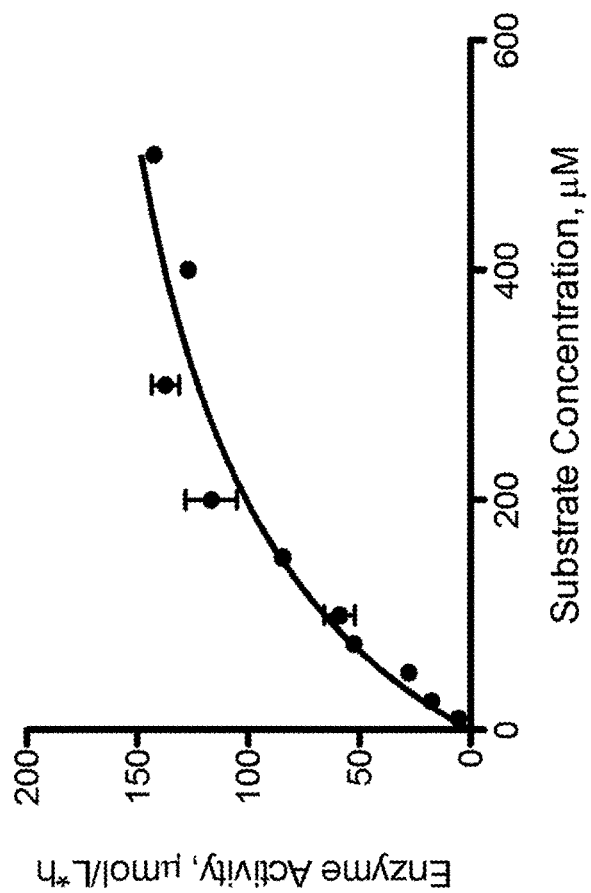
FIG. 12B
FIG. 12A

METHODS FOR ASSAYING PALMITOYL PROTEIN THIOESTERASE 1 AND TRIPEPTIDYL PEPTIDASE ACTIVITY IN DRIED BLOOD SPOTS FOR DETECTION OF NEURONAL CEROID LIPOFUSCINOSES IN NEWBORNS

CROSS-REFERENCE(S) TO RELATED APPLICATION(S)

This application claims the benefit of U.S. Patent Application No. 62/191,942, filed Jul. 13, 2015, the disclosure of which is hereby incorporated by reference in its entirety.

STATEMENT OF GOVERNMENT LICENSE RIGHTS

This invention was made with Government support under R01 DK067859, awarded by National Institutes of Health. The Government has certain rights in the invention.

BACKGROUND

The neuronal ceroid lipofuscinoses (NCLs) are a group of lysosomal storage disorders primarily affecting children and adolescents. NCLs are inherited as autosomal recessive disorders that cause neurodegenerative diseases manifesting similar clinical features, including seizures, mental regression, vision loss, behavior changes, movement disorders, and shortened life expectancy in affected individuals.

Of the two most prevalent forms, infantile neuronal ceroid lipofuscinosis (INCL), also called the Santavuori-Haltia disease, is caused by mutations in the CLN1 gene located on chromosome 1p32 which encodes the lysosomal enzyme palmitoyl protein thioesterase I (PPT1, EC3.1.2.22). Over 40 mutations of the CLN1 gene are known. PPT1 cleaves thioester-linked fatty acid groups from C-terminal cysteine residues in lipoproteins. PPT1 is structurally similar to lipases and has a peptide binding site as well as a well-defined fatty acid binding pocket.

The other NCL form, classic late infantile neuronal ceroid lipofuscinosis (NCL II, also called the Jansky-Bielschowsky disease) results from mutations in the TPP1 gene (previously named CLN2) which is located on chromosome 11p15 and encodes the lysosomal enzyme tripeptidylpeptidase 1 (TPP1). TPP1 is a serine protease that cleaves three amino acid residues from unsubstituted protein N-termini. The human form of TPP1 shows preferential cleavage of the Ala-Ala-Phe peptide triad.

NCLs collectively constitute the most common hereditary neurodegenerative disorder in childhood with an estimated prevalence of 1:12,500 newborns in the U.S. A particularly high incidence of INCL is found in Finland where it is due to a missense mutation (W122R). NCLs are incurable disorders and treatment of affected children has been mainly supportive. However, recent reports of enzyme replacement therapies and neuronal stem transplantation indicated that animals treated with recombinant enzymes showed significantly decreased levels of lysosomal storage material. This could possibly open an avenue for the development of a therapy for human NCLs. Because INCL is characterized by early onset (6 months to 1 year) and rapid progression, the success of any potential therapy strongly depends on early diagnosis. A detection strategy for such rare metabolic disorders, which is currently being explored on a large scale, is by screening the enzyme defects in dried blood spots (DBS) collected from entire newborn populations.

The most direct and specific diagnosis of NCLs relies on enzymatic assays in biological samples such as leukocytes or cultured skin fibroblasts, using radiometric or fluorescence detection. The radiometric method for PPT1 measures the release of tritium-labeled palmitate from a palmitate-labeled H-Ras protein. The fluorometric assay for PPT1, uses an S-palmitoyl-6-thiogalactosylcoumarin conjugate that requires a coupling enzyme to release the fluorescent 7-hydroxy-4-methylcoumarin for detection. The fluorometric assay for TPP1 uses Ala-Ala-Pro-7-amido-4-methylcoumarin that releases the fluorescent 7-amino-4-methylcoumarin upon enzymatic hydrolysis. These assays have been applied to analysis of dried blood spots (DBSs) from newborns.

Several assays of lysosomal enzyme activities in DBS using tandem mass spectrometry and selected reaction monitoring (SRM) have previously been reported. The enzymes were assayed with synthetic compounds that are structurally similar to the natural enzyme substrates and at the same time allow highly sensitive and specific detection of products by SRM-tandem mass spectrometry. The assays are designed to allow for simple sample handling and purification to be compatible with the work flow in newborn screening laboratories. The substrates are designed for multiplexed detection of several enzyme products and their quantitation by SRM in a single analytical run. Recent results of a pilot triplex study of over 100,000 dried blood spot (DBS) samples from newborns in Washington state showed a very low rate (<0.005%) of false positives, which indicated that multiplex analysis by tandem mass spectrometry is a robust and practical method of newborn screening for lysosomal storage disorders.

There is a need for developing a fast, inexpensive, and reliable diagnostic procedure that uses dried blood spots as a sample source, such as those submitted to newborn screening laboratories. A need also exists for methods and reagents for newborn screening of the activity of lysosomal enzymes, particularly methods and reagents that allow for improved screening of PPT1 and TPP1. The present disclosure fulfills this need and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure provides reagents for screening PPT1 and TPP1; methods for screening for PPT1 and TPP1, alone, in combination, or in combination with methods for screening of MPS metabolic syndromes caused by a deficiency of a lysosomal enzyme degrading glycosaminoglycans; and kits that include the reagents.

In one aspect, the disclosure provides methods for assaying for a lysosomal enzyme associated with a lysosomal storage disease, including:

(a) contacting a sample with a first solution to provide a solution including one or more lysosomal enzymes;

(b) contacting the one or more lysosomal enzymes in solution with one or more lysosomal enzyme substrates, and incubating the substrates with the lysosomal enzymes for a time sufficient to provide a solution comprising one or more enzyme products for the one or more lysosomal enzymes present in the sample, wherein the enzyme substrate includes a compound of Formula (TPP1-S1) and/or Formula (PPT1-S1):

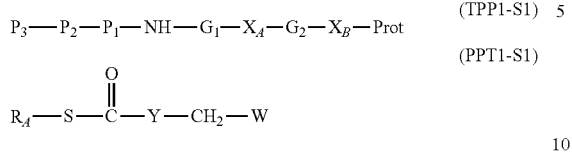

wherein in the compound of Formula (TPP1-S1),
P$_3$ is an achiral amino acid residue, a D-amino acid residue, or a L-amino acid residue;
P$_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, L-Lys, D-Asn, L-Asn, D-Asp, L-Asp, D-Arg, L-Arg, D-His, and L-His;
P$_1$ is an amino acid residue selected from D-Phe, L-Phe, D-Leu, L-Leu, D-Nle, L-Nle, D-Tyr, L-Tyr, D-Glu, L-Glu, D-Trp, L-Trp, D-Asp, L-Asp, D-Gln, L-Gln, D-Ala, L-Ala, D-Ser, L-Ser, D-Lys, L-Lys, D-Arg, L-Arg, D-Asn, L-Asn, D-His, L-His, D-Val, L-Val, D-Ile, L-Ile, D-Thr, L-Thr, Gly, D-Pro, and L-Pro;
wherein P$_3$ is located at a N-terminus of the P$_3$-P$_2$-P$_1$ moiety, and P$_1$ is located at a C-terminus of the P$_3$-P$_2$-P$_1$ moiety;
G$_1$ is a first linker including 2-20 carbon atoms in which one or more carbon atoms may be replaced with a heteroatom selected from N, O, and S, and/or one or more of carbon atoms may be substituted with a C$_1$-C$_6$ alkyl group, C$_1$-C$_6$ haloalkyl, halo, or amino;
X$_A$ is a first linking functionality linking G$_1$ to G$_2$ selected from a bond, amide, thioamide, sulfonamide, ether, sulfide, ureido, thioureido, and ester;
G$_2$ is a second linker including 2-20 carbon atoms in which one or more carbon atoms may be replaced with a heteroatom selected from N, O, and S, and/or one or more of carbon atoms may be substituted with a C$_1$-C$_6$ alkyl group or halogen; and
X$_B$ is a second linking functionality linking G$_2$ to Prot selected from a bond, NH, amide, thioamide, sulfonamide, ether, sulfide, ureido, thioureido, and ester;
Prot is a protecting group that is capable of fragmenting by one dominant pathway at an efficiency of greater than 5% to provide a residual enzyme product fragment that is detectable by mass spectrometry; and
wherein in the compound of Formula (PPT1-S1),
R$_A$ is selected from a peptide, a polymer, a polysaccharide, an aromatic hydrocarbon group, and an aliphatic hydrocarbon group;
W is selected from H and NHCO—C$_1$-C$_6$ alkyl; and
Y is a C$_2$-C$_{19}$ alkylene; and
(c) determining the quantities of the one or more enzyme products.

In another aspect, the disclosure provides methods of assaying for tripeptidyl peptidase 1, including:
(a) contacting a sample with a first solution to provide a solution including tripeptidyl peptidase 1;
(b) contacting the tripeptidyl peptidase 1 in solution with a tripeptidyl peptidase 1 substrate and incubating the substrate with the tripeptidyl peptidase 1 for a time sufficient to provide a solution including a tripeptidyl peptidase 1 product in the sample,
wherein the tripeptidyl peptidase 1 substrate is a compound of Formula (TPP1-S1):

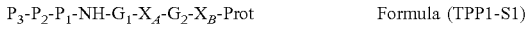

wherein:
P$_3$ is an achiral amino acid residue, a D-amino acid residue, or a L-amino acid residue, provided that the amino acid residue is not Pro;
P$_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, L-Lys, D-Asn, L-Asn, D-Asp, L-Asp, D-Arg, L-Arg, D-His, and L-His;
P$_1$ is an amino acid residue selected from D-Phe, L-Phe, D-Leu, L-Leu, D-Nle, L-Nle, D-Tyr, L-Tyr, D-Glu, L-Glu, D-Trp, L-Trp, D-Asp, L-Asp, D-Gln, L-Gln, D-Ala, L-Ala, D-Ser, L-Ser, D-Lys, L-Lys, D-Arg, L-Arg, D-Asn, L-Asn, D-His, L-His, D-Val, L-Val, D-Ile, L-Ile, D-Thr, L-Thr, Gly, D-Pro, and L-Pro;
wherein P$_3$ is located at a N-terminus of the P$_3$-P$_2$-P$_1$ moiety, P$_1$ is located at a C-terminus of the P$_3$-P$_2$-P$_1$ moiety;
G$_1$ is a first linker including 2-20 carbon atoms in which one or more carbon atoms may be replaced with a heteroatom selected from N, O, and S, and/or one or more of carbon atoms may be substituted with a C$_1$-C$_6$ alkyl group, C$_1$-C$_6$ haloalkyl, halo, or amino;
X$_A$ is a first linking functionality linking G$_1$ to G$_2$ selected from a bond, amide, thioamide, sulfonamide, ether, sulfide, ureido, thioureido, and ester;
G$_2$ is a second linker including 2-20 carbon atoms in which one or more carbon atoms may be replaced with a heteroatom selected from N, O, and S, and/or one or more of carbon atoms may be substituted with a C$_1$-C$_6$ alkyl group or halogen; and
X$_B$ is a second linking functionality linking G$_2$ to Prot selected from a bond, NH, amide, thioamide, sulfonamide, ether, sulfide, ureido, thioureido, and ester;
Prot is a protecting group that is capable of fragmenting by one dominant pathway at an efficiency of greater than 5% to provide a residual enzyme product fragment that is detectable by mass spectrometry, and
(c) determining the quantity of tripeptidyl peptidase 1 product.

In yet another aspect, the disclosure provides methods of assaying for palmitoyl protein thioesterase 1, comprising:
(a) contacting a sample with a first solution to provide a solution including palmitoyl protein thioesterase 1;
(b) contacting the palmitoyl protein thioesterase 1 in solution with a palmitoyl protein thioesterase 1 substrate and incubating the substrate with the palmitoyl protein thioesterase 1 for a time sufficient to provide a solution including a palmitoyl protein thioesterase 1 product in the sample,
wherein the palmitoyl protein thioesterase 1 substrate is a compound having Formula (PPT1-S1):

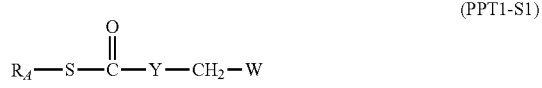

wherein:
R$_A$ is selected from a peptide, a polymer, a polysaccharide, an aromatic hydrocarbon group, and an aliphatic hydrocarbon group;
W is selected from H and NHCO—C$_1$-C$_6$ alkyl; and
Y is a C$_2$-C$_{19}$ alkylene, and
(c) determining the quantity of palmitoyl protein thioesterase product.

In some embodiments, the one or more lysosomal enzymes includes an enzyme selected from tripeptidyl peptidase 1 and palmitoyl protein thioesterase 1.

In some embodiments, in any of the above-mentioned assays, in step (b), the lysosomal enzyme substrates further includes a compound having a carbohydrate moiety and an aglycone moiety and having Formula (MPS-S):

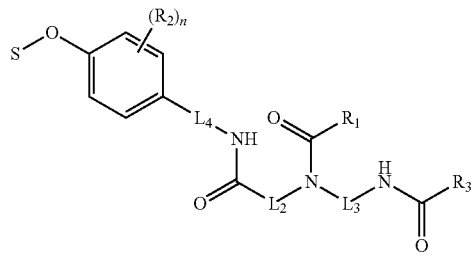

(MPS-S)

wherein S is the carbohydrate moiety that when covalently coupled to the aglycone moiety provides a substrate for an enzyme selected from the group consisting of:
(i) alpha-L-iduronidase;
(ii) iduronate 2-sulfatase;
(iii) heparan N-sulfatase;
(iv) N-acetyl-alpha-D-glucosaminidase;
(v) N-acetylgalactosamine 6-sulfate-sulfatase;
(vi) N-acetylgalactosamine 4-sulfate-sulfatase; and
(vii) beta-glucuronidase;

L$_2$ is a linker including 1-20 carbon atoms in which one or more carbon atoms may be replaced with a heteroatom selected from N, O, and S, and/or one or more of carbon atoms may be substituted with a C$_1$-C$_6$ alkyl group or halogen;

L$_3$ is a linker including 1-20 carbon atoms in which one or more carbon atoms may be replaced with a heteroatom selected from N, O, or S, and/or one or more of carbon atoms may be substituted with a C$_1$-C$_6$ alkyl group or halogen;

L$_4$ is optional and when present is a linker including 1-20 carbon atoms in which one or more carbon atoms may be replaced with a heteroatom selected from N, O, or S, and/or one or more of carbon atoms may be substituted with a C$_1$-C$_6$ alkyl group or halogen;

R$_1$ is a C$_1$-C$_{10}$ alkyl group or a C$_1$-C$_{10}$ alkoxy group;

R$_2$ at each occurrence is independently selected from a C$_1$-C$_{10}$ alkyl group, a C$_1$-C$_{10}$ alkoxy group, halogen, nitro, —C(=O)NHR, and —C(=O)OR, where R is C$_1$-C$_8$ alkyl group;

R$_3$ is a C$_1$-C$_{10}$ alkyl group or a substituted or unsubstituted C$_6$-C$_{10}$ aryl group; and n is 0, 1, 2, 3, or 4.

In some embodiments, the assayed lysosomal enzymes include one or more enzymes selected from the group consisting of:
(a) alpha-L-iduronidase;
(b) iduronate 2-sulfatase;
(c) heparan N-sulfatase;
(d) N-acetyl-alpha-D-glucosaminidase;
(e) N-acetylgalactosamine 6-sulfate-sulfatase;
(f) N-acetylgalactosamine 4-sulfate-sulfatase;
(g) beta-glucuronidase;
(h) tripeptidyl peptidase 1; and
(i) palmitoyl protein thioesterase 1.

In yet another aspect, the disclosure provides one or more internal standards including a structure of Formula (TPP1-IS1) and/or (PPT1-IS1),

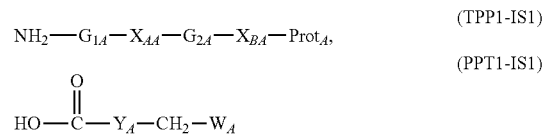

wherein in the structure of Formula (TPP1-IS1)
G$_{1A}$ is a first linker comprising 2-20 carbon atoms in which one or more carbon atoms may be replaced with a heteroatom selected from N, O, and S, and/or one or more of carbon atoms may be substituted with a C$_1$-C$_6$ alkyl group, C$_1$-C$_6$ haloalkyl, halo, or amino;

X$_{AA}$ is a first linking functionality linking G$_{1A}$ to G$_{2A}$ selected from a bond, amide, thioamide, sulfonamide, ether, sulfide, ureido, thioureido, and ester; G$_{2A}$ is a second linker comprising 2-20 carbon atoms in which one or more carbon atoms may be replaced with a heteroatom selected from N, O, and S, and/or one or more of carbon atoms may be substituted with a C$_1$-C$_6$ alkyl group or halogen;

X$_{BA}$ is a second linking functionality linking G$_{2A}$ to Prot$_A$ selected from a bond, NH, amide, thioamide, sulfonamide, ether, sulfide, ureido, thioureido, and ester; and Prot$_A$ is a protecting group that is capable of fragmenting by one dominant pathway at an efficiency of greater than 5% to provide a residual enzyme product fragment that is detectable by mass spectrometry, wherein the compound of Formula (TPP1-IS1) includes at least one hydrogen that is replaced by deuterium, a carbon-12 that is replaced by carbon-13, or a nitrogen-14 that is replaced by nitrogen-15; and wherein in the structure of Formula (PPT1-IS1)
W$_A$ is selected from H, NHCO—C$_1$-C$_6$ alkyl; and
Y$_A$ is a C$_2$-C$_{19}$ alkylene, and
wherein the compound of Formula (PPT1-IS1) includes at least one hydrogen that is replaced by deuterium, a carbon-12 that is replaced by carbon-13, or a nitrogen-14 that is replaced by nitrogen-15.

In yet another aspect, the disclosure provides a substrate for tripeptidyl peptidase 1, including a compound of Formula (TPP1-S1):

P$_3$-P$_2$-P$_1$-NH-G$_1$-X$_A$-G$_2$-X$_B$-Prot    (TPP1-S1)

wherein:
P$_3$ is an achiral amino acid residue, a D-amino acid residue, or a L-amino acid residue, provided that the amino acid residue is not Pro;

P$_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, L-Lys, D-Asn, L-Asn, D-Asp, L-Asp, D-Arg, L-Arg, D-His, and L-His;

P$_1$ is an amino acid residue selected from D-Phe, L-Phe, D-Leu, L-Leu, D-Nle, L-Nle, D-Tyr, L-Tyr, D-Glu, L-Glu, D-Trp, L-Trp, D-Asp, L-Asp, D-Gln, L-Gln, D-Ala, L-Ala, D-Ser, L-Ser, D-Lys, L-Lys, D-Arg, L-Arg, D-Asn, L-Asn, D-His, L-His, D-Val, L-Val, D-Ile, L-Ile, D-Thr, L-Thr, Gly, D-Pro, and L-Pro;

wherein $P_3$ is located at a N-terminus of the $P_3$-$P_2$-$P_1$ moiety, $P_1$ is located at a C-terminus of the $P_3$-$P_2$-$P_1$ moiety;

$G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $G_2$ selected from a bond, amide, thioamide, sulfonamide, ether, sulfide, ureido, thioureido, and ester;

$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen; and $X_B$ is a second linking functionality linking $G_2$ to Prot selected from a bond, NH, amide, thioamide, sulfonamide, ether, sulfide, ureido, thioureido, and ester; and Prot is a protecting group that is capable of fragmenting by one dominant pathway at an efficiency of greater than 5% to provide a residual enzyme product fragment that is detectable by mass spectrometry.

In yet another aspect, the disclosure provides a substrate for palmitoyl protein thioesterase 1, comprising a compound having Formula (PPT1-S1):

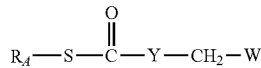

(PPT1-S1)

wherein:

$R_A$ is selected from a peptide, a polymer, a polysaccharide, an aromatic hydrocarbon group, and an aliphatic hydrocarbon group;

W is selected from H and NHCO—$C_1$-$C_6$ alkyl; and

Y is a $C_2$-$C_{19}$ alkylene.

In yet another aspect, the disclosure provides a method of assaying for one or more lysozymal enzymes, including:

(a) contacting a sample with a first solution to provide a solution comprising one or more lysosomal enzymes;

(b) contacting the one or more lysosomal enzymes in solution with one or more lysosomal enzyme substrates, and incubating the substrates with the lysosomal enzymes for a time sufficient to provide a solution comprising one or more enzyme products comprising a compound of Formula (TPP1-P1) and/or (PPT1-P1);

NH$_2$—G$_1$—X$_A$—G$_2$—X$_B$—Prot    (TPP1-P1)

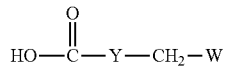

(PPT1-P1)

wherein in the compound for Formula (TPP1-P1), $G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $G_2$ selected from a bond, amide, thioamide, sulfonamide, ether, sulfide, ureido, thioureido, and ester;

$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen;

$X_B$ is a second linking functionality linking $G_2$ to Prot selected from a bond, NH, amide, thioamide, sulfonamide, ether, sulfide, ureido, thioureido, and ester;

Prot is a protecting group that is capable of fragmenting by one dominant pathway at an efficiency of greater than 5% to provide a residual enzyme product fragment that is detectable by mass spectrometry; and wherein in the compound of Formula (PPT1-P1), W is selected from H and NHCO—$C_1$-$C_6$ alkyl; and Y is a $C_2$-$C_{19}$ alkylene; and (c) determining the quantities of one or more of the enzyme products.

In yet another aspect, the disclosure provides a method of assaying for palmitoyl protein thioesterase 1, including:

(a) contacting a sample with a first solution to provide a solution including palmitoyl protein thioesterase 1;

(b) contacting the palmitoyl protein thioesterase 1 in solution with a palmitoyl protein thioesterase 1 substrate, and incubating the palmitoyl protein thioesterase 1 substrate with the palmitoyl protein thioesterase 1 for a time sufficient to provide a solution comprising a palmitoyl protein thioesterase 1 product comprising a compound of Formula (PPT1-P1);

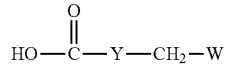

(PPT1-P1)

wherein in the compound of Formula (PPT1-P1)

W is selected from H and NHCO—$C_1$-$C_6$ alkyl; and

Y is a $C_2$-$C_{19}$ alkylene; and (c) determining the quantities of one or more of the enzyme products.

In yet another aspect, the disclosure provides a method of assaying for tripeptidyl peptidase 1, including:

(a) contacting a sample with a first solution to provide a solution comprising tripeptidase peptidase 1;

(b) contacting the tripeptidase peptidase 1 in solution with a tripeptidase peptidase 1 substrate, and incubating the tripeptidase peptidase 1 substrate with the tripeptidase peptidase 1 for a time sufficient to provide a solution comprising a tripeptidase peptidase 1 product including a compound of Formula (TPP1-P1);

NH$_2$-G$_1$-X$_A$-G$_2$-X$_B$-Prot    (TPP1-P1)

wherein in the compound for Formula (TPP1-P1), $G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $G_2$ selected from a bond, amide, thioamide, sulfonamide, ether, sulfide, ureido, thioureido, and ester;

$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen;

$X_B$ is a second linking functionality linking $G_2$ to Prot selected from a bond, NH, amide, thioamide, sulfonamide, ether, sulfide, ureido, thioureido, and ester; and Prot is a protecting group that is capable of fragmenting by one dominant pathway at an efficiency of greater than 5% to provide a residual enzyme product fragment that is detectable by mass spectrometry; and (c) determining the quantities of tripeptidase peptidase 1.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIG. 5 is a graphical representation of dry blood spots in contact with an embodiment of a PPT1 substrate (left) and an embodiment of a TPP1 substrate (right).

FIG. 12A is a Michaelis-Menten enzymatic activity plot for PPT1.

FIG. 12B is a Michaelis-Menten enzymatic activity plot for TPP1.

DETAILED DESCRIPTION

Figure 1A:
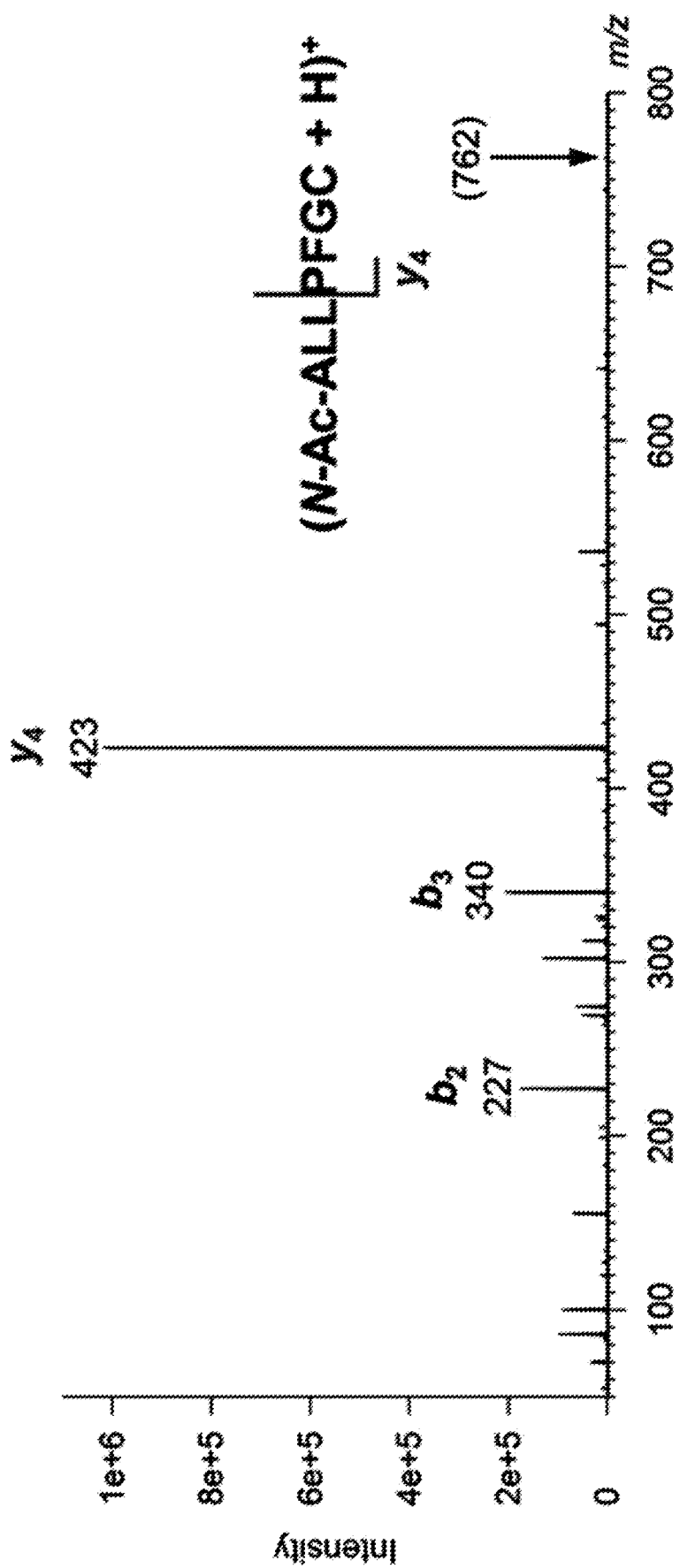
FIG. 1A is a tandem mass spectrum of (N-Ac-ALLP-FGC+H)$^+$ ion at m/z 762, obtained at 25 eV laboratory ion collision energy.

The present disclosure provides assays for lysosomal enzymes, specifically palmitoyl protein thioesterase 1 (PPT1) and tripeptidyl peptidase 1 (TPP1), using, for example, tandem mass spectrometry. The assays involve the detection of enzymatic products obtained through the action of the lysosomal enzymes on new enzyme substrates, and can be used for quantitative enzyme activity measurements. The assays for the enzymes utilize a minimum steps for sample work up and can be run in a simplex format or in a duplex format for the detection of neuronal ceroid lipofuscinoses (e.g., infantile neuronal ceroid lipofuscinosis (INCL, also called the Santavuori-Haltia disease); and/or classic late infantile neuronal ceroid lipofuscinosis (NCL II, also called the Jansky-Bielschowsky disease)), or in a multiplex format with other mass spectrometry-based assays for screening of neuronal ceroid lipofuscinoses and other lysosomal storage disorders.

In some embodiments, the assays use synthetic compounds that are designed to mimic the natural lysosomal enzyme substrates. Incubation of an enzyme present in, for example, a dried blood spot, with the synthetic compounds can produces relatively small quantities of enzymatic products per blood spot that can be quantified by tandem mass spectrometry (MS/MS) using synthetic internal standards and selected reaction monitoring.

Definitions

At various places in the present specification, substituents of compounds of the disclosure are disclosed in groups or in ranges. It is specifically intended that the disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

"Optionally substituted" groups can refer to, for example, functional groups that may be substituted or unsubstituted by additional functional groups. For example, when a group is unsubstituted, it can be referred to as the group name, for example alkyl or aryl. When a group is substituted with additional functional groups, it may more generically be referred to as substituted alkyl or substituted aryl.

As used herein, the term "alkyl" is meant to refer to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 50, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group.

As used herein, "alkenyl" refers to an alkyl group having one or more double carbon-carbon bonds. The alkenyl group can be linear or branched. Example alkenyl groups include ethenyl, propenyl, and the like. An alkenyl group can contain from 2 to about 50, from 2 to about 24, from 2 to about 20, from 2 to about 10, from 2 to about 8, from 2 to about 6, or from 2 to about 4 carbon atoms.

As used herein, "alkenylene" refers to a linking alkenyl group.

As used herein, "alkynyl" refers to an alkyl group having one or more triple carbon-carbon bonds. The alkynyl group can be linear or branched. Example alkynyl groups include ethynyl, propynyl, and the like. An alkynyl group can contain from 2 to about 50, from 2 to about 24, from 2 to about 20, from 2 to about 10, from 2 to about 8, from 2 to about 6, or from 2 to about 4 carbon atoms.

As used herein, "alkynylene" refers to a linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "haloalkenyl" refers to an alkenyl group having one or more halogen substituents.

As used herein, "haloalkynyl" refers to an alkynyl group having one or more halogen substituents.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "arylene" refers to a linking aryl group.

As used herein, "monocyclic aromatic hydrocarbs" refers to monocyclic aromatic hydrocarbons and monocyclic aromatic heterocycles having at least one heteroatom ring member such as sulfur, oxygen, or nitrogen. Any ring-forming N atom in a monocyclic aromatic heterocycle can also be oxidized to form an N-oxo moiety. Examples of monocyclic aromatic hydrocarbons include benzene and the like. In some embodiments, the monocyclic aromatic hydrocarbons have 6 carbon atoms. Examples of monocyclic aromatic heterocycles include without limitation, pyridine, pyrimidine, pyrazine, pyridazine and the like. In some embodiments, the monocyclic aromatic heterocycle contains 6 to about 14 ring-forming atoms. In some embodiments, the monocyclic aromatic heterocycle has 1 to about 4, 1 to about 3, or 1 to 2 heteroatoms.

As used herein, "polycyclic aromatic hydrocarbons" refers to a fused aromatic ring system (e.g., having 2, 3, 4, 5, 6, 7, 8, 9, 10, 11, 12, 13, 14, 15, or 16 fused rings) that optionally includes one or more heteroatom ring members such as sulfur, oxygen, or nitrogen. Examples of polycyclic aromatic hydrocarbons include naphthyl, anthracenyl, phenanthrenyl, indanyl, indenyl, and the like. Examples of polycyclic aromatic hydrocarbons that include one or more heteroatom ring members include quinoline, isoquinoline, benzofuran, benzothiophene, benzthiazole, pyrazino[2,3-g]quinoxaline, acenaphtho[1',2':5,6]pyrazino[2,3-g]acenaphtho[1,2-b]quinoxaline, and the like. In some embodiments, the polycyclic aromatic hydrocarbon has from 1 to about 30 carbon atoms, 1 to about 20 carbon atoms, and in further embodiments from about 6 to about 20 carbon atoms. In some embodiments, the polycyclic aromatic hydrocarbons contains 3 to about 20, 3 to about 14, 3 to about 7, or 5 to 6 ring-forming atoms. In some embodiments, the polycyclic aromatic hydrocarbon has 1 to about 8, 1 to about 4, 1 to about 3, or 1 to 2 heteroatoms.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like.

As used herein, "cycloalkylene" refers to a linking cycloalkyl group.

As used herein, "heteroalkyl" refers to an alkyl group having at least one heteroatom such as sulfur, oxygen, or nitrogen.

As used herein, "heteroalkylene" refers to a linking heteroalkyl group.

As used herein, a "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heteroarylene" refers to a linking heteroaryl group.

As used herein, "heterocycloalkyl" refers to a non-aromatic heterocycle where one (or more) of the ring-forming atom(s) is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. A heterocycloalkyl group having one or more fused aromatic rings can be attached though either the aromatic or non-aromatic portion. Also included in the definition of heterocycloalkyl are moieties where one (or more) ring-forming atom(s) is substituted by 1 or 2 oxo or sulfido groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "heterocycloalkylene" refers to a linking heterocycloalkyl group.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-(haloalkyl) group.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated.

Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

In some embodiments, the compounds of the disclosure, and salts thereof, are substantially isolated. By "substantially isolated" is meant that the compound is at least partially or substantially separated from the environment in which it was formed or detected. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Lysosomal Enzyme Assays

In one aspect, the present disclosure provides reagents that can be advantageously utilized to assay enzymes. The reagents include enzyme substrates (S), enzyme products (P), and assay internal standards (IS). In certain embodiments, one or more substrates (S) and their corresponding internal standards (IS) are incubated in a suitable buffer (e.g., 100 mM ammonium formate pH 4.5 containing 5 mM barium acetate and 7.5 mM cerium acetate) with a suitable source of enzymes, such as a dried blood spot from a newborn screening card or a urine sample, for a sufficient time, to form one or more products (P) that are subsequently detected by tandem mass spectrometry. In certain embodiments, the internal standard (IS) is chemically similar or identical to the enzyme-formed product except the standard has a different mass (e.g., homolog or heavy isotope substituted such as deuterium, carbon-13, and/or nitrogen-15 substitutions). In other embodiments, one or more substrates (S) are incubated in a suitable buffer with a suitable source of enzymes to form one or more products (P) that are subsequently detected by fluorescence analysis.

In general, to assay for the lysosomal enzymes in a dried blood spot, a dried blood spot or a portion thereof is contacted with an amount of a solution, such as an aqueous solution (e.g., an aqueous buffer such as phosphate buffered solution), to provide a solution containing one or more enzymes. The enzyme-containing solution is contacted with a substrate for at least one of the lysosomal enzymes, an internal standard for at least one of the lysosomal enzymes, and incubated for a period of time sufficient to provide a sample that includes one or more enzyme products. In some embodiments, incubation can occur in the presence of a surfactant, such as a non-ionic surfactant. After the period of incubation, the sample can be optionally quenched by addition of, for example, and acid and/or an organic solvent. The enzyme product and the internal standard can then be isolated. In some embodiments, the isolation includes solid phase extraction and elution from the solid phase using a solvent or a solvent mixture. In some embodiments, the isolation includes extraction into a solvent, such as an organic solvent. The isolated enzyme product and internal standard can then be analyzed (e.g., quantitated), for example, using mass spectrometry and/or fluorimetry.

The lysosomal enzyme assays can be carried out in a simplex, duplex, or multiplex manner. In a simplex assay, the activity of a single lysosomal enzyme, such as TPP1 or PPT1, is measured. As described above, the assay can include contacting the enzyme-containing solution with a substrate for either TPP1 or PPT1 and the corresponding internal standard for the TPP1 or PPT1 lysosomal enzyme, incubating the resulting sample, optionally quenching the sample, and isolating and analyzing the TPP1 or the PPT1 enzyme product and internal standard to determine the activity of the assayed lysosomal enzyme.

In a duplex assay, the activity of two lysosomal enzymes, such as TPP1 and PPT1, is measured. As described above, the assay can include contacting the enzyme-containing solution with a substrate and the corresponding internal standard for each of the two lysosomal enzymes (e.g., TPP1 and PPT1), incubating the resulting sample, optionally quenching the sample, and isolating and analyzing the enzyme product of each of the two lysosomal enzymes (e.g., TPP1 and PPT1) and internal standards to determine the activity of each of the two assayed lysosomal enzymes. In some embodiments, the assay includes separately contacting an enzyme-containing solution with a substrate and the corresponding internal standard for a given lysosomal enzyme, incubating the resulting sample, optionally quenching the sample, and isolating the enzyme product and internal standard for each of the lysosomal enzymes. The isolated enzyme product and internal standard for each of the two lysosomal enzymes (e.g., TPP1 and PPT1) can then be combined and the activities of the two assayed lysosomal enzymes can be analyzed together and simultaneously, for example, using mass spectrometry or fluorimetry.

In some embodiments, the lysosomal enzyme assays can be carried out in multiplex manner. The multiplex assay can be similarly carried out to a duplex assay, where the assay can include contacting the enzyme-containing solution with a substrate and the corresponding internal standard for each of the lysosomal enzymes to be assayed, incubating the resulting sample, optionally quenching the sample, and isolating and analyzing the enzyme products and internal standards to determine the activity of each of the assayed lysosomal enzymes. In some embodiments, the assay includes separately contacting an enzyme-containing solution with a substrate and the corresponding internal standard for a given lysosomal enzyme, incubating the resulting sample, optionally quenching the sample, and isolating the enzyme product and internal standard for each of the lysosomal enzymes. The isolated enzyme product and internal standard for each of the lysosomal enzymes can then be combined and the activities of the assayed lysosomal enzymes can be analyzed together and simultaneously, for example, using mass spectrometry or fluorimetry.

In some embodiments, enzymes that are advantageously assayed with the reagents of the disclosure include palmitoyl protein thioesterase 1 (PPT1) and tripeptidyl peptidase 1 (TPP1). The substrates, products, and internal standards for each of these two enzymes are described in detail below. Methods for detection of neuronal ceroid lipofuscinoses using tandem mass spectrometry from dried blood spots from human subjects using the substrates, products, and internal standards of the present disclosure are also described. Furthermore, reagents and methods for performing multiplex assays are presented.

TPP1 Substrates

In general, the TPP1 substrates includes a tripeptide moiety, $P_3$-$P_2$-$P_1$, where the $P_3$ is located at the N-terminus and the $P_1$ is located at the C terminus. The enzyme TPP1 cleaves the tripeptide at the C-terminus of $P_1$ of the tripeptide moiety.

In one embodiment, the disclosure provides TPP1 substrates defined by a compound of Formula (TPP1-S1):

$$P_3\text{-}P_2\text{-}P_1\text{-}NH\text{-}G_1\text{-}X_A\text{-}G_2\text{-}X_B\text{-}Prot \qquad \text{(TPP1-S1)}$$

wherein:

$P_3$ is an achiral amino acid residue, a D-amino acid residue, or a L-amino acid residue;

$P_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, L-Lys, D-Asn, L-Asn, D-Asp, L-Asp, D-Arg, L-Arg, D-His, and L-His;

$P_1$ is an amino acid residue selected from D-Phe, L-Phe, D-Leu, L-Leu, D-Nle, L-Nle, D-Tyr, L-Tyr, D-Glu, L-Glu, D-Trp, L-Trp, D-Asp, L-Asp, D-Gln, L-Gln, D-Ala, L-Ala, D-Ser, L-Ser, D-Lys, L-Lys, D-Arg, L-Arg, D-Asn, L-Asn, D-His, L-His, D-Val, L-Val, D-Ile, L-Ile, D-Thr, L-Thr, Gly, D-Pro, and L-Pro;

wherein $P_3$ is located at a N-terminus of the $P_3$-$P_2$-$P_1$ moiety, $P_1$ is located at a C-terminus of the $P_3$-$P_2$-$P_1$ moiety;

$G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $G_2$ selected from a bond, amide (e.g., —NHCO—), thioamide (e.g., —C(S)NH—), sulfonamide (e.g., —SO$_2$NH—), ether (e.g., —O—), sulfide (e.g., —S—), ureido (e.g., —NHC(O)NH—), thioureido (e.g., —NHS(O)NH—), and ester (e.g., —C(O)O—);

$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen; and $X_B$ is a second linking functionality linking $G_2$ to Prot selected from a bond, NH, amide, thioamide, sulfonamide, ether, sulfide, ureido, thioureido, and ester;

Prot is a protecting group that is capable of fragmenting by one dominant pathway at an efficiency of greater than 5% to provide a residual enzyme product fragment that is detectable by mass spectrometry.

As used herein, a linking functionality designates a functionality that covalently bonds two groups to one another. While examples of linking functionalities are given in one direction, it is understood that the linking functionality encompasses both the forward and the reverse linking directions, unless otherwise specified. For example, while an example of an amide linking functionality is given as —NHCO— (e.g., for linking $G_1$ to $G_2$), it is understood that —CONH— (e.g., for linking $G_1$ to $G_2$) is also encompassed by the amide linking functionality.

It is believed that the enzyme tripeptidyl peptidase 1 cleaves a tripeptide substrate at the C-terminal side of the tripeptide. In a compound of Formula TPP1-S1, $P_3$ is positioned at the N-terminal position and $P_1$ is positioned at the C-terminal position of the tripeptide, with the $P_3$ carboxyl coupled to the $P_2$ amino, the $P_2$ carboxyl coupled to the $P_1$ amino, and with the carboxyl group of $P_1$ coupled to the NH moiety in Formula TPP1-S1 (i.e., forming an amide linkage). Without wishing to be bound by theory, it is believed that TPP1 prefers P1 to be Phe, Leu, Nle (nor-leucine), or Tyr. In some embodiments, the enzyme secondarily prefers $P_1$ to be Glu, Trp, Asp, Gln, Ala, Ser, or Lys. In certain embodiments, the enzyme P1 recognizes Arg, Asn, His, Val, Ile, Thr, Gly, or Pro as P1, although less preferentially than Glu, Trp, Asp, Gln, Ala, Ser, or Lys.

For $P_2$, without wishing to be bound by theory, it is believed that when $P_1$ is Phe, Nle, or Leu, the preferred $P_2$ amino acid residues for TPP1 recognition are Nle, Pro, Ala, Phe, and Tyr, followed by Trp, Ile, Val, Thr, Glu, Ser, Leu, Gly, Gln, and Lys, which in turn are followed by Asn, Asp, Arg, and His. When $P_1$ is Tyr, it is believed that the enzyme prefers $P_2$ to be Nle, Pro, Ala, Phe, or Tyr.

For $P_3$, without wishing to be bound by theory, it is believed that all amino acid residues are tolerated except Pro.

In some embodiments, $P_2$ and $P_3$ can include D- or L-amino acid residues.

In some embodiments, $P_3$ is an amino acid residue selected from D-Ala, L-Ala, D-Arg, L-Arg, D-Asn, L-Asn, D-Asp, L-Asp, D-Cys, L-Cys, D-Glu, L-Glu, D-Gln, L-Gln, Gly, D-His, L-His, D-Ile, L-Ile, D-Leu, L-Leu, D-Lys, L-Lys, D-Met, L-Met, D-Phe, L-Phe, D-Pro, L-Pro, D-Ser, L-Ser, D-Thr, L-Thr, D-Trp, L-Trp, D-Tyr, L-Tyr, D-Val, and L-Val;

$P_2$ is an amino acid residue selected from L-Nle, L-Pro, L-Ala, L-Phe, and L-Tyr;

$P_1$ is an amino acid residue selected from L-Phe, L-Leu, L-Nle, and L-Tyr;

$G_1$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_A$ is amide;

$G_2$ is $(CH_2)_p$, wherein p is an integer from 3 to 20;

$X_B$ is selected from NH and amide; and

Prot is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

In some embodiments, $P_3$ is an amino acid residue selected from D-Ala, L-Ala, D-Arg, L-Arg, D-Asn, L-Asn, D-Asp, L-Asp, D-Cys, L-Cys, D-Glu, L-Glu, D-Gln, L-Gln, Gly, D-His, L-His, D-Ile, L-Ile, D-Leu, L-Leu, D-Lys, L-Lys, D-Met, L-Met, D-Phe, L-Phe, D-Pro, L-Pro, D-Ser, L-Ser, D-Thr, L-Thr, D-Trp, L-Trp, D-Tyr, L-Tyr, D-Val, and L-Val;

$P_2$ is an amino acid residue selected from D-Nle, L-Nle, D-Pro, L-Pro, D-Ala, L-Ala, D-Phe, L-Phe, D-Tyr, and L-Tyr;

$P_1$ is an amino acid residue selected from L-Phe, L-Leu, L-Nle, and L-Tyr;

$G_1$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_A$ is amide;

$G_2$ is $(CH_2)_p$, wherein p is an integer from 3 to 20;

$X_B$ is selected from NH and amide; and

Prot is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

In some embodiments, $P_3$ is an amino acid residue selected from D-Ala, L-Ala, D-Arg, L-Arg, D-Asn, L-Asn, D-Asp, L-Asp, D-Cys, L-Cys, D-Glu, L-Glu, D-Gln, L-Gln, Gly, D-His, L-His, D-Ile, L-Ile, D-Leu, L-Leu, D-Lys, L-Lys, D-Met, L-Met, D-Phe, L-Phe, D-Pro, L-Pro, D-Ser, L-Ser, D-Thr, L-Thr, D-Trp, L-Trp, D-Tyr, L-Tyr, D-Val, and L-Val;

$P_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, and L-Lys;

$P_1$ is an amino acid residue selected from L-Phe, L-Leu, L-Nle, and L-Tyr;

$G_1$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_A$ is amide;

$G_2$ is $(CH_2)_p$, wherein p is an integer from 3 to 20;

$X_B$ is selected from NH and amide; and

Prot is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

In some embodiments, $P_3$ is an amino acid residue selected from D-Ala, L-Ala, D-Arg, L-Arg, D-Asn, L-Asn, D-Asp, L-Asp, D-Cys, L-Cys, D-Glu, L-Glu, D-Gln, L-Gln, Gly, D-His, L-His, D-Ile, L-Ile, D-Leu, L-Leu, D-Lys, L-Lys, D-Met, L-Met, D-Phe, L-Phe, D-Pro, L-Pro, D-Ser, L-Ser, D-Thr, L-Thr, D-Trp, L-Trp, D-Tyr, L-Tyr, D-Val, and L-Val;

$P_2$ is an amino acid residue selected from L-Nle, L-Pro, L-Ala, L-Phe, L-Tyr, L-Trp, L-Ile, L-Val, L-Thr, L-Glu, L-Ser, L-Leu, Gly, L-Gln, and L-Lys;

$P_1$ is an amino acid residue selected from L-Phe, L-Leu, L-Nle, L-Tyr, L-Glu, L-Trp, L-Asp, L-Gln, L-Ala, L-Ser, and L-Lys;

$G_1$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_A$ is amide;

$G_2$ is $(CH_2)_p$, wherein p is an integer from 3 to 20;

$X_B$ is selected from NH and amide; and

Prot is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

In some embodiments, $P_3$ is an amino acid residue selected from D-Ala, L-Ala, D-Arg, L-Arg, D-Asn, L-Asn, D-Asp, L-Asp, D-Cys, L-Cys, D-Glu, L-Glu, D-Gln, L-Gln, Gly, D-His, L-His, D-Ile, L-Ile, D-Leu, L-Leu, D-Lys, L-Lys, D-Met, L-Met, D-Phe, L-Phe, D-Pro, L-Pro, D-Ser, L-Ser, D-Thr, L-Thr, D-Trp, L-Trp, D-Tyr, L-Tyr, D-Val, and L-Val;

$P_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, and L-Lys;

$P_1$ is an amino acid residue selected from L-Phe, L-Leu, L-Nle, L-Tyr, L-Glu, L-Trp, L-Asp, L-Gln, L-Ala, L-Ser, and L-Lys;

$G_1$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_A$ is amide;

$G_2$ is $(CH_2)_p$, wherein p is an integer from 3 to 20;

$X_B$ is selected from NH and amide; and

Prot is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

In some embodiments, $P_3$ is an amino acid residue selected from D-Ala, L-Ala, D-Arg, L-Arg, D-Asn, L-Asn, D-Asp, L-Asp, D-Cys, L-Cys, D-Glu, L-Glu, D-Gln, L-Gln, Gly, D-His, L-His, D-Ile, L-Ile, D-Leu, L-Leu, D-Lys, L-Lys, D-Met, L-Met, D-Phe, L-Phe, D-Pro, L-Pro, D-Ser, L-Ser, D-Thr, L-Thr, D-Trp, L-Trp, D-Tyr, L-Tyr, D-Val, and L-Val;

$P_2$ is an amino acid residue selected from L-Nle, L-Pro, L-Ala, L-Phe, L-Tyr, L-Trp, L-Ile, L-Val, L-Thr, L-Glu, L-Ser, L-Leu, Gly, L-Gln, L-Lys, L-Asn, L-Asp, L-Arg, and L-His;

$P_1$ is an amino acid residue selected from L-Phe, L-Leu, L-Nle, L-Tyr, L-Glu, L-Trp, L-Asp, L-Gln, L-Ala, L-Ser, L-Lys, L-Arg, L-Asn, L-His, L-Val, L-Ile, L-Thr, Gly, L-Pro;

$G_1$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_A$ is amide;

$G_2$ is $(CH_2)_p$, wherein p is an integer from 3 to 20;

$X_B$ is selected from NH and amide; and

Prot is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

In some embodiments, $P_3$ is an amino acid residue selected from D-Ala, L-Ala, D-Arg, L-Arg, D-Asn, L-Asn, D-Asp, L-Asp, D-Cys, L-Cys, D-Glu, L-Glu, D-Gln, L-Gln, Gly, D-His, L-His, D-Ile, L-Ile, D-Leu, L-Leu, D-Lys, L-Lys, D-Met, L-Met, D-Phe, L-Phe, D-Pro, L-Pro, D-Ser, L-Ser, D-Thr, L-Thr, D-Trp, L-Trp, D-Tyr, L-Tyr, D-Val, and L-Val;

$P_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, L-Lys, D-Asn, L-Asn, D-Asp, L-Asp, D-Arg, L-Arg, D-His, and L-His;

$P_1$ is an amino acid residue selected from L-Phe, L-Leu, L-Nle, L-Tyr, L-Glu, L-Trp, L-Asp, L-Gln, L-Ala, L-Ser, L-Lys, L-Arg, L-Asn, L-His, L-Val, L-Ile, L-Thr, Gly, and L-Pro;

$G_1$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_A$ is amide;

$G_2$ is $(CH_2)_p$, wherein p is an integer from 3 to 20;

$X_B$ is selected from NH and amide; and

Prot is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

In some embodiments, $P_3$ is an amino acid residue selected from L-Ala, L-Arg, L-Asn, L-Asp, L-Cys, L-Glu, L-Gln, Gly, L-His, L-Ile, L-Leu, L-Lys, L-Met, L-Phe, L-Pro, L-Ser, L-Thr, L-Trp, L-Tyr, and L-Val;

$P_2$ is an amino acid residue selected from L-Nle, L-Pro, L-Ala, L-Phe, and L-Tyr;

$P_1$ is an amino acid residue selected from L-Phe, L-Leu, L-Nle, and L-Tyr;

$G_1$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_A$ is amide;

$G_2$ is $(CH_2)_p$, wherein p is an integer from 3 to 20;

$X_B$ is selected from NH and amide; and

Prot is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

In some embodiments, the substrate of Formula (TPP1-S1) is a compound of Formula (TPP1-S2):

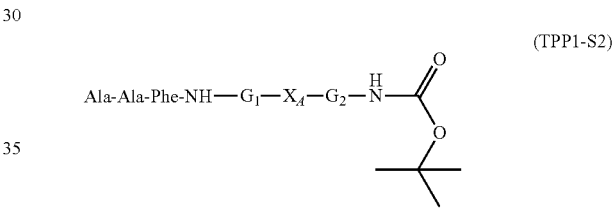

(TPP1-S2)

wherein $G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $G_2$ selected from a bond, amide, thioamide, sulfonamide, ether, sulfide, ureido, thioureido, and ester;

$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen.

In some embodiments, the substrate of Formula (TPP1-S1) is a compound of Formula (TPP1-S3):

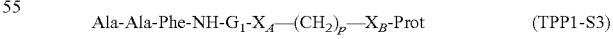

Ala-Ala-Phe-NH-$G_1$-$X_A$—$(CH_2)_p$—$X_B$-Prot  (TPP1-S3)

$G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $(CH_2)_p$ selected from a bond, amide, thioamide, sulfonamide, ether, sulfide, ureido, thioureido, and ester;

$X_B$ is a second linking functionality linking $(CH_2)_p$ to Prot selected from a bond, NH, amide, thioamide, sulfonamide, ether, sulfide, ureido, thioureido, and ester;

Prot is a protecting group that is capable of fragmenting by one dominant pathway at an efficiency of greater than 5% to provide a residual enzyme product fragment that is detectable by mass spectrometry; and p is an integer from 3 to 20.

In some embodiments, the substrate of Formula (TPP1-S1) is a compound of Formula (TPP1-S4):

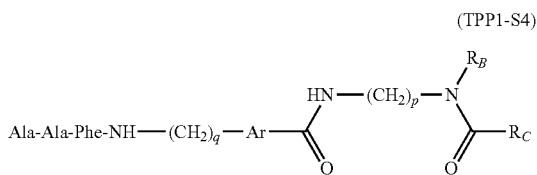

(TPP1-S4)

wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino;

$R_B$ is selected from H, $C_1$-$C_6$ alkyl, and $C_1$-$C_6$ haloalkyl;

$R_C$ is selected from $C_1$-$C_6$ alkoxy, $C_1$-$C_6$ alkyl, di-$C_1$-$C_6$ alkylamino, and $C_1$-$C_6$ alkylamino;

p is an integer from 3 to 6; and q is an integer from 0 to 4.

In some embodiments, the substrate of Formula (TPP1-S1) is a compound of Formula (TPP1-S5):

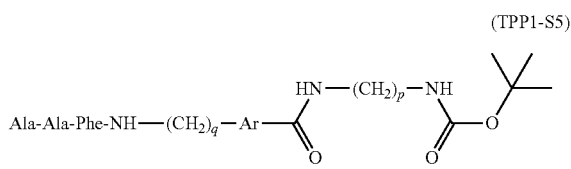

(TPP1-S5)

wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino;

p is an integer from 3 to 6; and q is an integer from 0 to 4.

In some embodiments, the substrate of Formula (TPP1-S1) is a compound of Formula (TPP1-S6):

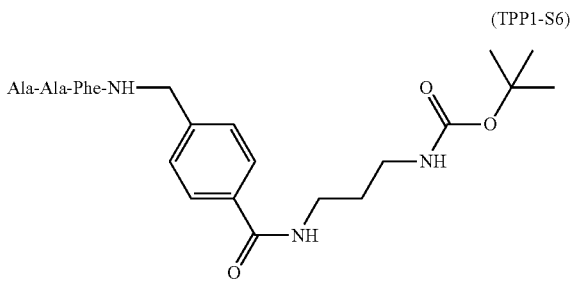

(TPP1-S6)

It is understood that where the amino acid residues do not specify the L- or D-isomeric forms, the L-form is implied.

In any of the above-described TPP1 substrates, the following embodiments can apply, in any combination.

In some embodiments, Ar is phenylene. For example, Ar can be a 1,4-phenylene, a 1-3-phenylene, or a 1,2-phenylene.

In some embodiments, $G_1$ is a first linker including one or more moieties selected from $C_6$-$C_{10}$ arylene, $C_3$-$C_{10}$ heteroarylene, $C_6$-$C_{10}$ cycloalkylene, $C_3$-$C_{10}$ heterocycloalkylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_1$ is a first linker including one or more moieties selected from $C_6$-$C_{10}$ arylene, $C_3$-$C_{10}$ heteroarylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_1$ is a first linker including one or more moieties selected from $C_6$-$C_{10}$ arylene and $C_1$-$C_{10}$ alkylene, each optionally substituted by 1, 2, 3, or 4 substituents independently selected from $C_1$-$C_6$ alkyl, $C_1$-$C_6$ haloalkyl, halo, and amino.

In some embodiments, $G_1$ is a first linker including $C_6$-$C_{10}$ arylene optionally substituted by 1, 2, 3, or 4 substituents independently selected from $C_1$-$C_6$ alkyl, $C_1$-$C_6$ haloalkyl, halo, and amino.

In some embodiments, $G_1$ is a first linker including $C_1$-$C_{10}$ alkylene optionally substituted by 1, 2, 3, or 4 substituents independently selected from $C_1$-$C_6$ alkyl, $C_1$-$C_6$ haloalkyl, halo, and amino.

In some embodiments, $X_A$ is a first linking functionality linking $G_1$ to $G_2$ selected from amide, thioamide, sulfonamide, ether, sulfide, ureido, thioureido, and ester.

In some embodiments, $X_A$ is an amide.

In some embodiments, $G_2$ is a second linker including one or more moieties selected from $C_6$-$C_{10}$ arylene, $C_3$-$C_{10}$ heteroarylene, $C_6$-$C_{10}$ cycloalkylene, $C_3$-$C_{10}$ heterocycloalkylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_2$ is a second linker including one or more moieties selected from $C_6$-$C_{10}$ arylene, $C_3$-$C_{10}$ heteroarylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_2$ is a second linker including one or more moieties selected from $C_6$-$C_{10}$ arylene and $C_1$-$C_{10}$ alkylene, each optionally substituted by 1, 2, 3, or 4 substituents independently selected from $C_1$-$C_6$ alkyl, $C_1$-$C_6$ haloalkyl, halo, and amino.

In some embodiments, $G_2$ is a second linker including $C_6$-$C_{10}$ arylene optionally substituted by 1, 2, 3, or 4 substituents independently selected from $C_1$-$C_6$ alkyl, $C_1$-$C_6$ haloalkyl, halo, and amino.

In some embodiments, $G_2$ is a second linker including $C_1$-$C_{10}$ alkylene optionally substituted by 1, 2, 3, or 4 substituents independently selected from $C_1$-$C_6$ alkyl, $C_1$-$C_6$ haloalkyl, halo, and amino.

In some embodiments, $X_B$ is a second linking functionality linking $G_1$ to $G_2$ selected from amide, NH, thioamide, sulfonamide, ether, sulfide, ureido, thioureido, and ester.

In some embodiments $X_B$ is a selected from NH and amide.

In some embodiments, $X_B$ is an amide.

In some embodiments, $X_B$ is NH.

In some embodiments, $R_B$ is selected from H and $C_1$-$C_6$ alkyl.

In some embodiments, $R_B$ is H.

In some embodiments, $R_C$ is selected from $C_1$-$C_6$ alkoxy and $C_1$-$C_6$ alkyl.

In some embodiments, $R_C$ is $C_1$-$C_6$ alkoxy.

In some embodiments, $P_3$ is a natural amino acid residue.

In some embodiments, $P_3$ is an amino acid residue selected from D-Ala, L-Ala, D-Arg, L-Arg, D-Asn, L-Asn, D-Asp, L-Asp, D-Cys, L-Cys, D-Glu, L-Glu, D-Gln, L-Gln, Gly, D-His, L-His, D-Ile, L-Ile, D-Leu, L-Leu, D-Lys, L-Lys, D-Met, L-Met, D-Phe, L-Phe, D-Pro, L-Pro, D-Ser, L-Ser, D-Thr, L-Thr, D-Trp, L-Trp, D-Tyr, L-Tyr, D-Val, and L-Val.

In some embodiments, $P_3$ is an amino acid residue selected from L-Ala, L-Arg, L-Asn, L-Asp, L-Cys, L-Glu, L-Gln, Gly, L-His, L-Ile, L-Leu, L-Lys, L-Met, L-Phe, L-Pro, L-Ser, L-Thr, L-Trp, L-Tyr, and L-Val.

In some embodiments, $P_3$ is a neutral amino acid residue.

In some embodiments, $P_3$ is an amino acid residue selected from D-Trp, L-Trp, D-Phe, L-Phe, Gly, D-Ala, L-Ala, D-Val, L-Val, D-Ile, L-Ile, D-Leu, L-Leu, D-Met, L-Met, D-Pro, L-Pro, D-Ser, L-Ser, D-Thr, L-Thr, D-Asn, L-Asn, D-Gln, L-Gln, D-Cys, and L-Cys.

In some embodiments, $P_3$ is an amino acid residue selected from L-Trp, L-Phe, Gly, L-Ala, L-Val, L-Ile, L-Leu, L-Met, L-Pro, L-Ser, L-Thr, L-Asn, L-Gln, and L-Cys.

In some embodiments, $P_3$ is selected from a D-Ala and a L-Ala amino acid residue.

In some embodiments, $P_3$ is a L-Ala amino acid residue.

In some embodiments, $P_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, L-Lys, D-Asn, L-Asn, D-Asp, L-Asp, D-Arg, L-Arg, D-His, and L-His.

In some embodiments, $P_2$ is an amino acid residue selected from L-Nle, L-Pro, L-Ala, L-Phe, L-Tyr, L-Trp, L-Ile, L-Val, L-Thr, L-Glu, L-Ser, L-Leu, Gly, L-Gln, L-Lys, L-Asn, L-Asp, L-Arg, and L-His.

In some embodiments, $P_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, and L-Lys.

In some embodiments, $P_2$ is an amino acid residue selected from L-Nle, L-Pro, L-Ala, L-Phe, L-Tyr, L-Trp, L-Ile, L-Val, L-Thr, L-Glu, L-Ser, L-Leu, Gly, L-Gln, and L-Lys.

In some embodiments, $P_2$ is an amino acid residue selected from D-Nle, L-Nle, D-Pro, L-Pro, D-Ala, L-Ala, D-Phe, L-Phe, D-Tyr, and L-Tyr.

In some embodiments, $P_2$ is an amino acid residue selected from L-Nle, L-Pro, L-Ala, L-Phe, and L-Tyr.

In some embodiments, $P_1$ is an amino acid residue selected from D-Phe, L-Phe, D-Leu, L-Leu, D-Nle, L-Nle, D-Tyr, L-Tyr, D-Glu, L-Glu, D-Trp, L-Trp, D-Asp, L-Asp, D-Gln, L-Gln, D-Ala, L-Ala, D-Ser, L-Ser, D-Lys, L-Lys, D-Arg, L-Arg, D-Asn, L-Asn, D-His, L-His, D-Val, L-Val, D-Ile, L-Ile, D-Thr, L-Thr, Gly, D-Pro, and L-Pro.

In some embodiments, $P_1$ is an amino acid residue selected from L-Phe, L-Leu, L-Nle, L-Tyr, L-Glu, L-Trp, L-Asp, L-Gln, L-Ala, L-Ser, L-Lys, L-Arg, L-Asn, L-His, L-Val, L-Ile, L-Thr, Gly, and L-Pro.

In some embodiments, $P_1$ is an amino acid residue selected from D-Phe, L-Phe, D-Leu, L-Leu, D-Nle, L-Nle, D-Tyr, L-Tyr, D-Glu, L-Glu, D-Trp, L-Trp, D-Asp, L-Asp, D-Gln, L-Gln, D-Ala, L-Ala, D-Ser, L-Ser, D-Lys, and L-Lys.

In some embodiments, $P_1$ is an amino acid residue selected from L-Phe, L-Leu, L-Nle, L-Tyr, L-Glu, L-Trp, L-Asp, L-Gln, L-Ala, L-Ser, and L-Lys.

In some embodiments, $P_1$ is an amino acid residue selected from D-Phe, L-Phe, D-Leu, L-Leu, D-Nle, L-Nle, D-Tyr, and L-Tyr.

In some embodiments, $P_1$ is an amino acid residue selected from L-Phe, L-Leu, L-Nle, and L-Tyr.

In some embodiments, $P_1$ an amino acid residue is selected from D-Glu, L-Glu, D-Trp, L-Trp, D-Asp, L-Asp, D-Gln, L-Gln, D-Ala, L-Ala, D-Ser, L-Ser, D-Lys, and L-Lys.

In some embodiments, $P_1$ is an amino acid residue selected from L-Glu, L-Trp, L-Asp, L-Gln, L-Ala, L-Ser, and L-Lys.

In some embodiments, $P_1$ is an amino acid residue selected from D-Arg, L-Arg, D-Asn, L-Asn, D-His, L-His, D-Val, L-Val, D-Ile, L-Ile, D-Thr, L-Thr, Gly, D-Pro, and L-Pro.

In some embodiments, $P_1$ is an amino acid residue selected from L-Arg, L-Asn, L-His, L-Val, L-Ile, L-Thr, Gly, and L-Pro.

In some embodiments, when $P_1$ is an amino acid residue selected from L-Phe, L-Nle, and L-Leu, $P_2$ is an amino acid residue selected from D-Nle, L-Nle, D-Pro, L-Pro, D-Ala, L-Ala, D-Phe, L-Phe, D-Tyr, and L-Tyr.

In some embodiments, when $P_1$ is an amino acid residue selected from L-Phe, L-Nle, and L-Leu, $P_2$ is an amino acid residue selected from L-Nle, L-Pro, L-Ala, L-Phe, and L-Tyr.

In some embodiments, when $P_1$ is selected from L-Phe, L-Nle, and L-Leu, $P_2$ is an amino acid residue selected from D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys and L-Lys.

In some embodiments, when $P_1$ is selected from L-Phe, L-Nle, and L-Leu, $P_2$ is an amino acid residue selected from L-Trp, L-Ile, L-Val, L-Thr, L-Glu, L-Ser, L-Leu, Gly, L-Gln, and L-Lys.

In some embodiments, when $P_1$ is selected from L-Phe, L-Nle, or L-Leu, $P_2$ is an amino acid residue selected from D-Asn, L-Asn, D-Asp, L-Asp, D-Arg, L-Arg, D-His, and L-His.

In some embodiments, when $P_1$ is selected from L-Phe, L-Nle, or L-Leu, $P_2$ is an amino acid residue selected from L-Asn, L-Asp, L-Arg, and L-His.

In some embodiments, when $P_1$ is a L-Tyr amino acid residue, $P_2$ is selected from D-Nle, L-Nle, D-Pro, L-Pro, D-Ala, L-Ala, D-Phe, L-Phe, D-Tyr, and L-Tyr.

In some embodiments, when $P_1$ is a L-Tyr amino acid residue, $P_2$ is selected from L-Nle, L-Pro, L-Ala, L-Phe, and L-Tyr.

In some embodiments, Prot is capable of fragmenting by one dominant pathway at a fragmentation efficiency of greater than 10% (e.g., greater than 20%, greater than 30%, greater than 40%, greater than 50%, greater than 60%, greater than 70%, or greater than 80%), when the substrate is subjected to collision-induced fragmentation in a tandem mass spectrometer, to improve sensitivity and to provide a residual enzyme product fragment that is detectable by mass spectrometry. For example, Prot can be $C(O)OC(CH_3)_3$, which can fragment nearly completely by the loss of 100 Da (e.g., loss of t-butyl group and the $CO_2$ group).

TPP1 Product

In some embodiments, the TPP1 substrates described above when subjected to the TPP lysosomal enzyme, provide TPP1 products (TPP1-P) having Formula (TPP1-P1):

                                         (TPP1-P1)

wherein $G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $G_2$ selected from a bond, amide, thioamide, sulfonamide, ether, sulfide, ureido, thioureido, and ester;

$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen;

$X_B$ is a second linking functionality linking $G_2$ to Prot selected from a bond, NH, amide, thioamide, sulfonamide, ether, sulfide, ureido, thioureido, and ester;

Prot is a protecting group that is capable of fragmenting by one dominant pathway at an efficiency of greater than 5% to provide a residual enzyme product fragment that is detectable by mass spectrometry.

The compound of Formula (TPP1-P1) can be detected by mass spectrometry. When subjected to mass spectrometric conditions, the compound can fragments by the loss of the Prot group, which can fragment by one dominant pathway at an efficiency of greater than 5% (e.g., greater than 10%, greater than 20%, greater than 30%, greater than 40%, greater than 50%, greater than 60%, greater than 70%, or greater than 80%) to provided enhanced sensitivity. The TPP1-P1 enzymatic product can be extracted from a sample mixture, for example, with an organic solvent like ethyl acetate to desalt prior to tandem mass spectrometry. Therefore, the $G_1$ moiety can be relatively hydrophobic, such that it can provide organic solvent solubility to the enzymatic product.

In some embodiments, $G_1$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_A$ is amide;

$G_2$ is $(CH_2)_p$, wherein p is an integer from 3 to 20;

$X_B$ is selected from NH and amide; and

Prot is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

In some embodiments, the compound of Formula (TPP1-P1) is a compound of Formula (TPP1-P2):

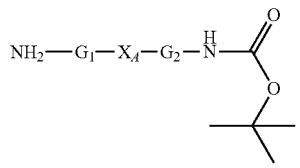                                         (TPP1-P2)

wherein $G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $G_2$ selected from a bond, amide, thioamide, sulfonamide, ether, sulfide, ureido, thioureido, and ester;

$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen.

In some embodiments, the compound of Formula (TPP1-P1) is a compound of Formula (TPP1-P3):

                                         (TPP1-P3)

$G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $(CH_2)_p$ selected from a bond, amide, thioamide, sulfonamide, ether, sulfide, ureido, thioureido, and ester;

$X_B$ is a second linking functionality linking $(CH_2)_p$ to Prot selected from a bond, NH, amide, thioamide, sulfonamide, ether, sulfide, ureido, thioureido, and ester;

Prot is a protecting group that is capable of fragmenting by one dominant pathway at an efficiency of greater than 5% to provide a residual enzyme product fragment that is detectable by mass spectrometry; and p is an integer from 3 to 20.

In some embodiments, the compound of Formula (TPP1-P1) is a compound of Formula (TPP1-P4):

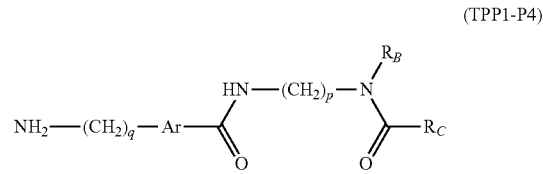

(TPP1-P4)

wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino;

$R_B$ is selected from H, $C_1$-$C_6$ alkyl, and $C_1$-$C_6$ haloalkyl;

$R_C$ is selected from $C_1$-$C_6$ alkoxy, $C_1$-$C_6$ alkyl, di-$C_1$-$C_6$ alkylamino, and $C_1$-$C_6$ alkylamino;

p is an integer from 3 to 6; and q is an integer from 0 to 4.

In some embodiments, the compound of Formula (TPP1-P1) is a compound of Formula (TPP1-P5):

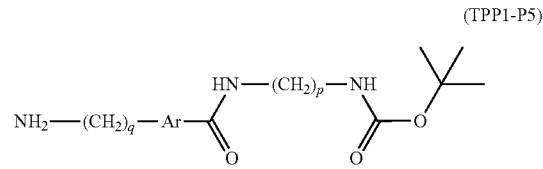

(TPP1-P5)

wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino;

p is an integer from 3 to 6; and q is an integer from 0 to 4.

In some embodiments, the compound of Formula (TPP1-P1) is a compound of Formula (TPP1-P6):

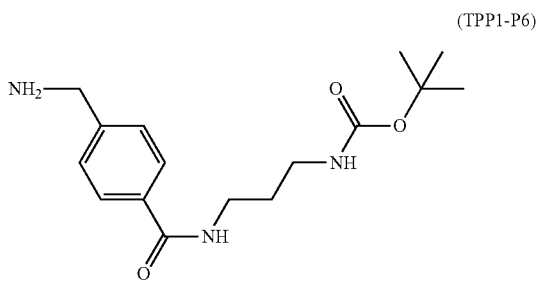 [SMILES: CC(C)(C)OC(=O)NCCCNC(=O)c1ccc(CN)cc1]

(TPP1-P6)

In any of the above-described TPP1 products (TPP1-P), the following embodiments can apply, in any combination.

In some embodiments, Ar is phenylene. For example, Ar can be a 1,4-phenylene, a 1-3-phenylene, or a 1,2-phenylene.

In some embodiments, $G_1$ is a first linker including one or more moieties selected from $C_6$-$C_{10}$ arylene, $C_3$-$C_{10}$ heteroarylene, $C_6$-$C_{10}$ cycloalkylene, $C_3$-$C_{10}$ heterocycloalkylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_1$ is a first linker including one or more moieties selected from $C_6$-$C_{10}$ arylene, $C_3$-$C_{10}$ heteroarylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_1$ is a first linker including one or more moieties selected from $C_6$-$C_{10}$ arylene and $C_1$-$C_{10}$ alkylene, each optionally substituted by 1, 2, 3, or 4 substituents independently selected from $C_1$-$C_6$ alkyl, $C_1$-$C_6$ haloalkyl, halo, and amino.

In some embodiments, $G_1$ is a first linker including $C_6$-$C_{10}$ arylene optionally substituted by 1, 2, 3, or 4 substituents independently selected from $C_1$-$C_6$ alkyl, $C_1$-$C_6$ haloalkyl, halo, and amino.

In some embodiments, $G_1$ is a first linker including $C_1$-$C_{10}$ alkylene optionally substituted by 1, 2, 3, or 4 substituents independently selected from $C_1$-$C_6$ alkyl, $C_1$-$C_6$ haloalkyl, halo, and amino.

In some embodiments, $X_A$ is a first linking functionality linking $G_1$ to $G_2$ selected from amide, thioamide, sulfonamide, ether, sulfide, ureido, thioureido, and ester.

In some embodiments, $X_A$ is an amide.

In some embodiments, $G_2$ is a second linker including one or more moieties selected from $C_6$-$C_{10}$ arylene, $C_3$-$C_{10}$ heteroarylene, $C_6$-$C_{10}$ cycloalkylene, $C_3$-$C_{10}$ heterocycloalkylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_2$ is a second linker including one or more moieties selected from $C_6$-$C_{10}$ arylene, $C_3$-$C_{10}$ heteroarylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_2$ is a second linker including one or more moieties selected from $C_6$-$C_{10}$ arylene and $C_1$-$C_{10}$ alkylene, each optionally substituted by 1, 2, 3, or 4 substituents independently selected from $C_1$-$C_6$ alkyl, $C_1$-$C_6$ haloalkyl, halo, and amino.

In some embodiments, $G_2$ is a second linker including $C_6$-$C_{10}$ arylene optionally substituted by 1, 2, 3, or 4 substituents independently selected from $C_1$-$C_6$ alkyl, $C_1$-$C_6$ haloalkyl, halo, and amino.

In some embodiments, $G_2$ is a second linker including $C_1$-$C_{10}$ alkylene optionally substituted by 1, 2, 3, or 4 substituents independently selected from $C_1$-$C_6$ alkyl, $C_1$-$C_6$ haloalkyl, halo, and amino.

In some embodiments, $X_B$ is a second linking functionality linking $G_1$ to $G_2$ selected from NH, amide, thioamide, sulfonamide, ether, sulfide, ureido, thioureido, and ester.

In some embodiments, $X_B$ is selected from NH and amide.

In some embodiments, $X_B$ is an amide.

In some embodiments, $X_B$ is NH.

In some embodiments, $R_B$ is selected from H and $C_1$-$C_6$ alkyl.

In some embodiments, $R_B$ is H.

In some embodiments, $R_C$ is selected from $C_1$-$C_6$ alkoxy and $C_1$-$C_6$ alkyl.

In some embodiments, $R_C$ is $C_1$-$C_6$ alkoxy.

In some embodiments, Prot is capable of fragmenting by one dominant pathway at an efficiency of greater than 10% (e.g., greater than 20%, greater than 30%, greater than 40%, greater than 50%, greater than 60%, greater than 70%, or greater than 80%), when the substrate is subjected to collision-induced fragmentation in a tandem mass spectrometer, to provide a residual enzyme product fragment that is detectable by mass spectrometry.

PPT1 Substrate

In one embodiment, the disclosure provides PPT1 substrates (PPT1-S) defined by a compound of Formula (PPT1-S1)

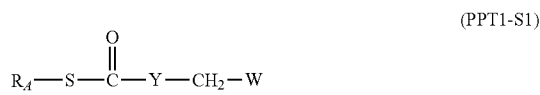

(PPT1-S1)

wherein:

$R_A$ is any group;

W is selected from H and NHCO—$C_1$-$C_6$ alkyl; and

Y is a $C_2$-$C_{19}$ alkylene; and (c) determining the quantities of the one or more enzyme products.

In some embodiments, $R_A$ is selected from a peptide (e.g., a naturally occurring peptide), a polymer, a polysaccharide, an aromatic hydrocarbon group, and an aliphatic hydrocarbon group.

In some embodiments, the PPT1 substrate of Formula (PPT1-S1) is a compound of Formula (PPT1-S2):

(PPT1-S2)

wherein

Ac is acetyl, and

Pal is C(O)—$C_{15}$ alkyl.

ALLPFGC in formula (PPT1-S2) refers to the peptide sequence Ala-Leu-Leu-Pro-Phe-Gly-Cys, N-Ac refers to an acylated N-terminus on the Ala residue.

In some embodiments, the PPT substrate of Formula (PPT1-S1) is a compound of Formula (PPT1-S3):

N-Ac-Ala-Ala-Ala-Pro-Phe-Gly-Cys-S-Pal         (PPT1-S3)

wherein
Ac is acetyl, and
Pal is C(O)—C$_{15}$ alkyl.

In some embodiments, the PPT substrate of Formula (PPT1-S1) is a compound of Formula (PPT1-S3):

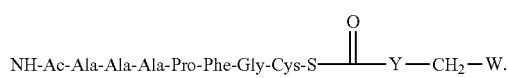
NH-Ac-Ala-Ala-Ala-Pro-Phe-Gly-Cys-S—C(=O)—Y—CH$_2$—W.     (PPT1-S4)

wherein
Ac is acetyl,
W is selected from H and NHCO—C$_1$-C$_6$ alkyl; and
Y is a C$_2$-C$_{19}$ alkylene.

In any of the above-described PPT1 substrates (PPT1-S), the following embodiments can apply, in any combination.

In some embodiments, R$_A$ is selected from a peptide, a polymer, a polysaccharide, an aromatic hydrocarbon group, and an aliphatic hydrocarbon group.

In some embodiments, R$_A$ has a molecular weight of greater than 500.

In some embodiments, R$_A$ is a small molecule having a molecular weight of less than 2000.

In some embodiments, R$_A$ is a peptide. In some embodiments, the peptide is naturally occurring.

In some embodiments, R$_A$ is N-acetyl-Ala-Ala-Ala-Pro-Phe-Gly-Cys, and S in Formula (II) is a sulfur on the Cys side chain.

In some embodiments, R$_A$ is N-acetyl-Ala-Leu-Leu-Pro-Phe-Gly-Cys, and S in Formula (II) is a sulfur on the Cys side chain.

In some embodiments, W is NHCO—C$_1$-C$_6$ alkyl.
In some embodiments, W is NHCOCH$_3$.
In some embodiments, Y is a C$_3$-C$_{11}$ alkylene.

In some embodiments, for the PPT1-S compounds, when a fatty acyl group (e.g., CH$_3$—(CH$_2$)$_{10}$—C=O, a lauroyl group) is on the thiol of the Cys side chain via a thiol ester linkage, PPT1 removes the fatty acyl group leaving the R$_A$ group, which can, for example, be a peptide. The R$_A$ group can be detected by tandem mass spectrometry. Alternatively, the enzymatically-cleaved HOOC—Y—CH$_2$—W can be extracted into an organic solvent during a desalting procedure. The enzymatically-cleaved HOOC—Y—CH$_2$-W can be multiplexed with other lysosomal assays that use an organic solvent extraction for desalting. When W is H, the resulting fatty acid product can be detected in negative ion mode in tandem mass spectrometry. When W is NHCO—C$_1$-C$_6$ alkyl, the terminal amido can protonate and the product can be observed in positive ion mode along with the other products in a multiplex assay of the other lysosomal enzymes, which can be done in positive mode. Without wishing to be bound by theory, it is believed that the PPT1 enzyme is tolerant of many R$_A$ groups. For example, R$_A$ can include cysteine-containing peptides where a fatty acyl group is covalently linked to a cysteine residue's side chain via the thiol group.

PPT1 Product

In some embodiments, the PPT1 substrates (PPT1-S) described above when subjected to the PPT1 lysosomal enzyme, provide PPT1 products (PPT1-P) having Formula (PPT1-P1):

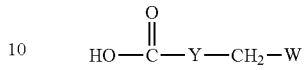
HO—C(=O)—Y—CH$_2$—W        (PPT1-P1)

wherein:
W is selected from H and NHCO—C$_1$-C$_6$ alkyl; and
Y is a C$_2$-C$_{19}$ alkylene.

In any the above-described PPT1 products, the following embodiments can apply, in any combination.

In some embodiments, W is NHCO—C$_1$-C$_6$ alkyl.
In some embodiments, W is NHCOCH$_3$.
In some embodiments, Y is a C$_3$-C$_{11}$ alkylene.

Internal Standards

Heavy Atom Derivatives.

In certain embodiments, the reagents of the disclosure include their heavy atom derivatives (i.e., derivatives that include one or more heavy atom isotopes). The heavy atom derivatives are useful as internal standards for assays utilizing mass spectrometric analysis. In certain embodiments, the TPP1 and PPT1 substrates have one or more (e.g., three or more) hydrogen atoms replaced with deuterium, or one or more (e.g., three or more) carbon atoms replaced with carbon-13 such that the mass of the TPP1 and PPT1 substrates is increased by one or more Daltons. As between an enzyme product and internal standard pair, the reagents differ in mass and the difference in mass can be achieved through the use of additional (or fewer) atoms (e.g., changing the length of a portion of the compound by one or more methylenes for, for example, G$_1$, G$_2$, Y, W) or through the incorporation of heavy atoms (e.g., deuterium for hydrogen, $^{13}$C for carbon, $^{15}$N for nitrogen in, for example, G$_1$, G$_2$, X$_A$, X$_B$, Prot, R$_A$, W, and/or Y).

The internal standard for each lysosomal enzyme can be analyzed before, after, or simultaneously with contacting the lysosomal enzymes with the one or more substrates.

TPP1 Internal Standard

In general, the TPP1 internal standards (TPP1-IS) can have the same structure as the TPP1 substrates, except that the internal standards have one or more (e.g., three or more) hydrogen atoms replaced with deuterium, one or more (e.g., three or more) carbon atoms replaced with carbon-13, or one or more (e.g., three or more) nitrogen atoms replaced with nitrogen-15 such that the mass of the TPP1 internal standards is increased by one or more Daltons compared to the corresponding substrates. In some embodiments, the internal standards can differ from the corresponding substrates by additional or fewer atoms (e.g., changing the length of a portion of the compound by one or more methylenes for, for example, G$_1$, G$_2$) or through the incorporation of heavy atoms (e.g., deuterium for hydrogen, $^{13}$C for carbon, $^{15}$N for nitrogen in, for example, G$_1$, G$_2$, X$_A$, X$_B$, Prot).

In one embodiment, the internal standard for a TPP1 assay has a structure of Formula (TPP1-IS1), NH$_2$-G$_{1A}$-X$_{AA}$-G$_{2A}$-X$_{BA}$-Prot$_A$         (TPP1-IS1)

wherein

G$_{1A}$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_{AA}$ is a first linking functionality linking $G_{1A}$ to $G_{2A}$ selected from a bond, amide, thioamide, sulfonamide, ether, sulfide, ureido, thioureido, and ester;

$G_{2A}$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen;

$X_{BA}$ is a second linking functionality linking $G_{2A}$ to $Prot_A$ selected from a bond, NH, amide, thioamide, sulfonamide, ether, sulfide, ureido, thioureido, and ester; and $Prot_A$ is a protecting group that is capable of fragmenting by one dominant pathway at an efficiency of greater than 5% to provide a residual enzyme product fragment that is detectable by mass spectrometry, wherein the compound of Formula (TPP1-IS1) includes at least one hydrogen that is replaced by deuterium, at least one carbon-12 that is replaced by carbon-13, or at least one nitrogen-14 that is replaced by nitrogen-15.

In some embodiments, $G_{1A}$ is $(CH_2)_q$—Ar, wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino; and q is an integer from 0 to 4;

$X_{AA}$ is amide;

$G_{2A}$ is $(CH_2)_p$, wherein p is an integer from 3 to 20;

$X_{BA}$ is selected from NH and amide; and $Prot_A$ is selected from $C(O)OC_1$-$C_6$ alkyl, $C_1$-$C_6$ alkoxy, $C_1$-$C_6$ alkyl, di-$C_1$-$C_6$ alkylamino, and $C_1$-$C_6$ alkylamino, wherein the compound of Formula (TPP1-IS1) includes at least one hydrogen that is replaced by deuterium, at least one carbon-12 that is replaced by carbon-13, and/or at least one nitrogen-14 that is replaced by nitrogen-15.

In some embodiments, the internal standard of Formula (TPP1-IS1) is a compound of Formula (TPP1-IS2):

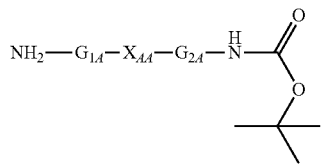

(TPP1-IS2)

wherein $G_{1A}$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_{AA}$ is a first linking functionality linking $G_{1A}$ to $G_{2A}$ selected from a bond, amide, thioamide, sulfonamide, ether, sulfide, ureido, thioureido, and ester;

$G_{2A}$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen, wherein the compound of Formula (TPP1-IS2) includes at least one hydrogen that is replaced by deuterium, at least one carbon-12 that is replaced by carbon-13, and/or at least one nitrogen-14 that is replaced by nitrogen-15.

In some embodiments, the compound of Formula (TPP1-IS1) is a compound of Formula (TPP1-IS3):

(TPP1-IS3)

$G_{1A}$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_{AA}$ is a first linking functionality linking $G_{1A}$ to $(CH_2)_p$ selected from a bond, amide, thioamide, sulfonamide, ether, sulfide, ureido, thioureido, and ester;

$X_{BA}$ is a second linking functionality linking $(CH_2)_p$ to $Prot_A$ selected from a bond, NH, amide, thioamide, sulfonamide, ether, sulfide, ureido, thioureido, and ester;

$Prot_A$ is a protecting group that is capable of fragmenting by one dominant pathway at an efficiency of greater than 5% to provide a residual enzyme product fragment that is detectable by mass spectrometry; and p is an integer from 3 to 20, wherein the compound of Formula (TPP1-IS3) includes at least one hydrogen that is replaced by deuterium, at least one carbon-12 that is replaced by carbon-13, and/or at least one nitrogen-14 that is replaced by nitrogen-15.

In some embodiments, the compound of Formula (TPP1-IS1) is a compound of Formula (TPP1-IS4):

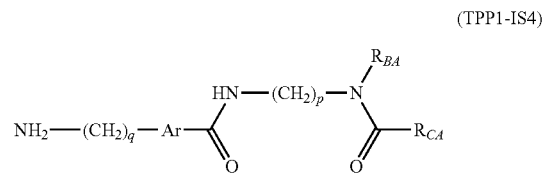

(TPP1-IS4)

wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino;

$R_{BA}$ is selected from H, $C_1$-$C_6$ alkyl, and $C_1$-$C_6$ haloalkyl;

$R_{CA}$ is selected from $C_1$-$C_6$ alkoxy, $C_1$-$C_6$ alkyl, di-$C_1$-$C_6$ alkylamino, and $C_1$-$C_6$ alkylamino;

p is an integer from 3 to 6; and q is an integer from 0 to 4, wherein the compound of Formula (TPP1-IS4) includes at least one hydrogen that is replaced by deuterium, at least one carbon-12 that is replaced by carbon-13, and/or at least one nitrogen-14 that is replaced by nitrogen-15.

In some embodiments, the compound of Formula (TPP1-IS1) is a compound of Formula (TPP1-IS5):

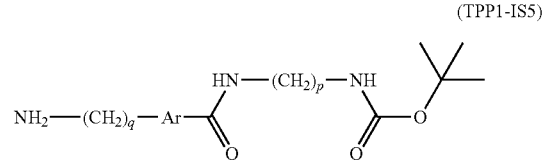

(TPP1-IS5)

wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino;

p is an integer from 3 to 6; and q is an integer from 0 to 4, wherein the compound of Formula (TPP1-IS5) includes at least one hydrogen that is replaced by deuterium, at least one carbon-12 that is replaced by carbon-13, and/or at least one nitrogen-14 that is replaced by nitrogen-15.

In some embodiments, the internal standard of Formula (TPP1-IS1) is a compound of Formula (TPP1-IS6):

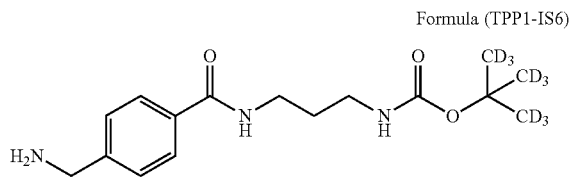 [SMILES: [2H]C([2H])([2H])C(OC(=O)NCCCNC(=O)c1ccc(CN)cc1)(C([2H])([2H])[2H])C([2H])([2H])[2H]]

Formula (TPP1-IS6)

In any of the above-described TPP1 internal standards (TPP1-IS), the following embodiments can apply, in any combination.

In some embodiments, Ar is phenylene. For example, Ar can be a 1,4-phenylene, a 1-3-phenylene, or a 1,2-phenylene.

In some embodiments, $G_{1A}$ is a first linker including one or more moieties selected from $C_6$-$C_{10}$ arylene, $C_3$-$C_{10}$ heteroarylene, $C_6$-$C_{10}$ cycloalkylene, $C_3$-$C_{10}$ heterocycloalkylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_{1A}$ is a first linker including one or more moieties selected from $C_6$-$C_{10}$ arylene, $C_3$-$C_{10}$ heteroarylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_{1A}$ is a first linker including one or more moieties selected from $C_6$-$C_{10}$ arylene and $C_1$-$C_{10}$ alkylene, each optionally substituted by 1, 2, 3, or 4 substituents independently selected from $C_1$-$C_6$ alkyl, $C_1$-$C_6$ haloalkyl, halo, and amino.

In some embodiments, $G_{1A}$ is a first linker including $C_6$-$C_{10}$ arylene optionally substituted by 1, 2, 3, or 4 substituents independently selected from $C_1$-$C_6$ alkyl, $C_1$-$C_6$ haloalkyl, halo, and amino.

In some embodiments, $G_{1A}$ is a first linker including $C_1$-$C_{10}$ alkylene optionally substituted by 1, 2, 3, or 4 substituents independently selected from $C_1$-$C_6$ alkyl, $C_1$-$C_6$ haloalkyl, halo, and amino.

In some embodiments, $X_{AA}$ is a first linking functionality linking $G_1$ to $G_2$ selected from amide, thioamide, sulfonamide, ether, sulfide, ureido, thioureido, and ester.

In some embodiments, $X_{AA}$ is an amide.

In some embodiments, $G_{2A}$ is a second linker including one or more moieties selected from $C_6$-$C_{10}$ arylene, $C_3$-$C_{10}$ heteroarylene, $C_6$-$C_{10}$ cycloalkylene, $C_3$-$C_{10}$ heterocycloalkylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_{2A}$ is a second linker including one or more moieties selected from $C_6$-$C_{10}$ arylene, $C_3$-$C_{10}$ heteroarylene, $C_1$-$C_{10}$ alkylene, $C_1$-$C_{10}$ heteroalkylene, $C_2$-$C_{10}$ alkenylene, $C_2$-$C_{10}$ heteroalkenylene, $C_2$-$C_{10}$ alkynylene, and $C_2$-$C_{10}$ heteroalkynylene, each optionally substituted by 1, 2, 3, or 4 substituents independently selected from $C_1$-$C_6$ alkyl, $C_1$-$C_6$ haloalkyl, halo, and amino.

In some embodiments, $G_{2A}$ is a second linker including one or more moieties selected from $C_6$-$C_{10}$ arylene and $C_1$-$C_{10}$ alkylene, each optionally substituted by 1, 2, 3, or 4 substituents independently selected from $C_1$-$C_6$ alkyl, $C_1$-$C_6$ haloalkyl, halo, and amino.

In some embodiments, $G_{2A}$ is a second linker including $C_6$-$C_{10}$ arylene optionally substituted by 1, 2, 3, or 4 substituents independently selected from $C_1$-$C_6$ alkyl, $C_1$-$C_6$ haloalkyl, halo, and amino.

In some embodiments, $G_{2A}$ is a second linker including $C_1$-$C_{10}$ alkylene optionally substituted by 1, 2, 3, or 4 substituents independently selected from $C_1$-$C_6$ alkyl, $C_1$-$C_6$ haloalkyl, halo, and amino.

In some embodiments, $X_{BA}$ is a first linking functionality linking $G_{1A}$ to $G_{2A}$ selected from NH, amide, thioamide, sulfonamide, ether, sulfide, ureido, thioureido, and ester.

In some embodiments, $X_{BA}$ is selected from NH and amide.

In some embodiments, $X_{BA}$ is an amide.

In some embodiments, $X_{BA}$ is NH.

In some embodiments, $R_{BA}$ is selected from H and $C_1$-$C_6$ alkyl.

In some embodiments, $R_{BA}$ is H.

In some embodiments, $R_{CA}$ is selected from $C_1$-$C_6$ alkoxy and $C_1$-$C_6$ alkyl.

In some embodiments, $R_{CA}$ is $C_1$-$C_6$ alkoxy.

In some embodiments, $Prot_A$ is capable of fragmenting by one dominant pathway at an efficiency of greater than 10% (e.g., greater than 20%, greater than 30%, greater than 40%, greater than 50%, greater than 60%, greater than 70%, or greater than 80%), when the substrate is subjected to collision-induced fragmentation in a tandem mass spectrometer, to provide a residual enzyme product fragment that is detectable by mass spectrometry.

In some embodiments, the TPP1 internal standard includes at least one hydrogen that is replaced by deuterium, and/or at least one carbon-12 that is replaced by carbon-13.

In some embodiments, the TPP1 internal standard includes at least one hydrogen that is replaced by deuterium.

PPT1 Internal Standards

In general, the PPT1 internal standards can have the same structure as the PPT1 substrates, except that the internal standards have one or more (e.g., three or more) hydrogen atoms replaced with deuterium, one or more (e.g., three or more) carbon atoms replaced with carbon-13, or one or more (e.g., three or more) nitrogen atoms replaced with nitrogen-15 such that the mass of the PPT1 internal standards is increased by one or more Daltons compared to the corresponding substrates. In some embodiments, the internal standards can differ from the corresponding substrates by additional or fewer atoms (e.g., changing the length of a portion of the compound by one or more methylenes for, for example, Y, W) or through the incorporation of heavy atoms (e.g., deuterium for hydrogen, $^{13}C$ for carbon, $^{15}N$ for nitrogen in, for example, in a compound of Formula (PPT1-IS1)).

In one embodiment, the internal standard for a PPT1 assay (PPT1-IS) has a structure of Formula (PPT1-IS1):

(PPT1-IS1)

wherein:

$W_A$ is selected from H and NHCO—$C_1$-$C_6$ alkyl; and $Y_A$ is a $C_2$-$C_{19}$ alkylene, and wherein the compound of Formula (PPT1-IS1) includes at least one hydrogen that is replaced by deuterium, at least one carbon-12 that is replaced by carbon-13, and/or at least one nitrogen-14 that is replaced by nitrogen-15.

In any of the above-described PPT1 internal standards, the following embodiments can apply, in any combination.

In some embodiments, $W_A$ is NHCO—$C_1$-$C_6$ alkyl.

In some embodiments, $Y_A$ is a $C_3$-$C_{11}$ alkylene.

In some embodiments, the PPT internal standard includes at least one hydrogen that is replaced by deuterium, and/or at least one carbon-12 that is replaced by carbon-13.

In some embodiments, the PPT internal standard includes at least one hydrogen that is replaced by deuterium.

Salts

In certain embodiments, the reagents (e.g., the substrates, products, and/or internal standards) include amino groups (e.g., —$NH_2$), carboxylic acid groups (—$CO_2H$), sulfonic acid groups (e.g., —$OSO_3H$), and amidosulfonic acid groups (e.g., —$NHSO_3H$), which depending on the pH environment can become charged groups (e.g., —$NH_3^+$, —$CO_2^-$, —$OSO_3^-$, —$NHSO_3^-$). It will be appreciated that the reagents of the disclosure include their salts (e.g., metal salts).

Multiplex Assays

In some embodiments, assays using the TPP1 and/or PPT1 substrates, products, and internal standards described above can be combined with assays for the detection of deficiencies of lysosomal enzymes degrading glycosaminoglycans for the screening of certain metabolic diseases/syndromes such as mucopolysaccharidoses (MPS), as described in U.S. patent application Ser. No. 14/916,526, entitled Reagents and Methods for Screening MPS I, II, IIIA, IIIB, IVA, VI, and VII, filed Mar. 3, 2016, the entirety of which is herein incorporated by reference. Thus, in one aspect, the disclosure provides a method for simultaneously assaying TPP1, PPT1, MPS-I, MPS-II, MPS-IIIA, MPS-IIIB, MPS-IVA, MPS-VI, and MPS-VII, or any subset thereof, using the reagents described herein.

The MPS (MPS I to VII) are a group of metabolic diseases/syndromes caused by a deficiency of one of the lysosomal enzymes degrading the glycosaminoglycans (including heparan, dermatan, keratan, or chondroitin sulfate). The pertinent enzymes include five sulfatases, four exoglycosidases, and one non-hydrolytic acetyl-N-transferase. These syndromes result in non-degraded or partially-degraded glycosaminoglycans amassing in the lysosome resulting in irreversible multi-systemic organ damage.

Enzymes that can be screened in a multiplex assay with an assay for TPP1 and/or PPT1 include the following:

(a) alpha-L-iduronidase, which acts on the substrate MPS-I-S to produce the product MPS-I-P, and the assay makes use of the internal standard MPS-I-IS;

(b) iduronate-2-sulfatase, which acts on the substrate MPS-II-S to produce the product MPS-II-P, and the assay makes use of the internal standard MPS-II-IS;

(c) heparan N-sulfatase, which acts on the substrate MPS-IIIA-S to produce the product MPS-IIIA-P, and the assay makes use of the internal standard MPS-IIIA-IS;

(d) N-acetyl-alpha-D-glycosaminidase, which acts on the substrate MPS-IIIB-S to produce the product MPS-IIIB-P, and the assay makes use of the internal standard MPS-IIIB-IS;

(e) N-acetylgalactosamine-6-sulfate-sulfatase, which acts on the substrate MPS-IVA-S to produce the product MPS-IVA-P, and the assay makes use of the internal standard MPS-IVA-IS;

(f) N-acetylgalactosamine-4-sulfate-sulfatase, which acts on the substrate MPS-VI-S to produce the product MPS-VI-P, and the assay makes use of the internal standard MPS-VI-IS; and (g) beta-glucuronidase, which acts on the substrate MPS-VII-S to produce the product MPS-VII-P, and the assay makes use of the internal standard MPS-VII-IS.

For embodiments that utilize mass spectrometry to quantitate assay products, in certain embodiments, the product for each assay is mass distinct. The mass of each product differs such that a single assay can be utilized to quantitate all assay products. The mass distinctiveness is achieved by choice of substrates. For example, the representative substrates of TPP1 and PPT1 described above and of MPS-I, MPS-II, MPS-IIIA, MPS-IIIB, MPS-IVA, MPS-VI, and MPS-VII described below provide mass distinct products (i.e., no two products have the same mass). Together with their corresponding internal standards (see representative internal standards of TPP1 and PPT1 described above, and of MPS-I, MPS-II, MPS-IIIA, MPS-IIIB, MPS-IVA, MPS-VI, and MPS-VII described below), the result is the ability to perform and analyze more than a single assay at a time.

In some embodiments, more than one product ion may have the same mass. In these embodiments, quantitation can be obtained so long as the fragment masses derived from these isobaric products are different (i.e., the combination of parent ion mass/fragment ion mass are unique for each species to be quantified in the mixture).

Reagents for screening mucopolysaccharidoses I, II, IIIA, IIIB, IVA, VI, and VII, (MPS-I, II, IIIA, IIB, IVA, VI, and VII, respectively), methods for screening for MPS-I, II, IIIA, IIIB, IVA, VI, and VII, and kits that include the reagents are described below. The reagents can be used in methods that advantageously assay one or more of TPP1, PPT1, alpha-L-iduronidase (MPS-I), iduronate-2-sulfatase (MPS-II), heparan N-sulfatase (MPS-IIIA), N-acetyl-alpha-D-glycosaminidase (MPS-IIIB), N-acetylgalactosamine-6-sulfate-sulfatase (MPS-IVA), N-acetylgalactosamine-4-sulfate-sulfatase (MPS-VI), and beta-glucuronidase (MPS-VII).

The following is a description of the reagents, substrates (S), products (P), and internals standards (IS) for MPS-I, MPS-II, MPS-IIIA, MPS-IIIB, MPS IVA, MPS-VI, and MPS-VII.

MPS Reagents

Sugar-Aglycone.

The substrates of the MPS are glycosides. The term "glycoside" refers to a compound in which a sugar group (glycone) is bonded through its anomeric carbon to another group (aglycone) by a glycosidic bond.

The substrates for the MPS assays are characterized as having a sugar-aglycone structure. The sugar component of the substrates is either the natural sugar that is a substrate for the particular enzyme or a modified sugar that maintains function sufficient to be a substrate for the particular enzyme to be assayed. The aglycone component of the substrate allows for analysis of the enzymatic activity. The aglycone component of the substrate is also a component of the enzyme product, which is analyzed to determine enzymatic activity. The aglycone component includes functionality for analysis for mass spectrometry or fluorescence. When the analysis is by mass spectrometry, an internal standard having a mass that is different from the product may be employed. The internal standard is either structurally identical to the product and includes one or more isotopes (e.g., deuterium or $^{13}C$) or is structurally similar having a functionally equivalent structure and a structural variation (e.g., a homolog: —$(CH_2)_5$— v. —$(CH_2)_6$—, or vice versa).

Aglycones.

The MPS reagents include an aglycone component. The nature of the aglycone can vary depending on the nature of the analytical technique utilized to assay the enzymes of interest. Representative aglycones are represented by formulae (I)-(VI) below. In the aglycone structures below, the wavy line depicts the point of attachment to the sugar anomeric carbon.

In certain embodiments, the aglycone is a Type A aglycone having the formula:

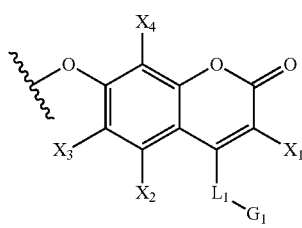

(MPS-I)

where $L_1$ is a linker that covalently couples $G_1$ to the coumarin moiety, and where $X_1$, $X_2$, $X_3$, and $X_4$ at each occurrence is independently hydrogen or halogen (e.g., chloro).

In certain embodiments, $L_1$ includes 1-20 carbon atoms (branched or linear) in which one or more carbon atoms may be replaced with an ether oxygen or —C(=O)O— group; a thioether sulfur or —C(=O)S— group; an NH, an N(R), or —C(=O)NH— or —C(=O)NR— where R is an alkyl group of 1-6 carbons. Substitution of one or more of the carbon atoms is optional. In certain embodiments, $L_1$ is —$CH_2$—C(=O)—NH—$(CH_2)_5$-$G_1$.

$G_1$ includes a positively charged group (e.g., a permanently positively charged group such as a quaternary ammonium ion) such as one of the following:

(a) $N(R_a)(R_b)(R_c)^+$, where $R_a$, $R_b$, and $R_c$ are each independently H or an alkyl group of 1-6 carbons;

(b) $S(R_a)(R_b)^+$, where $R_a$ and $R_b$ are as above;

(c) a pyridinium of the type

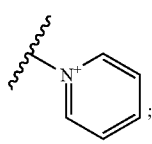 [SMILES: *[n+]1ccccc1]

(d) a pyridinium of the type

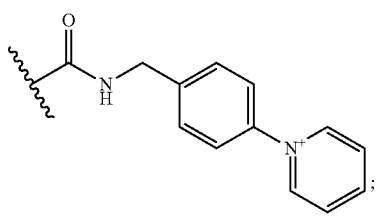 [SMILES: *C(=O)NCc1ccc(-[n+]2ccccc2)cc1]

(e) a pyridinium of the type

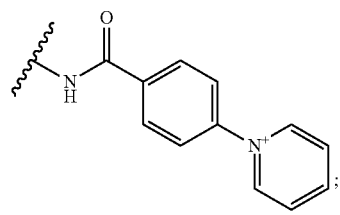 [SMILES: *NC(=O)c1ccc(-[n+]2ccccc2)cc1]

(f) a pyridinium of the type

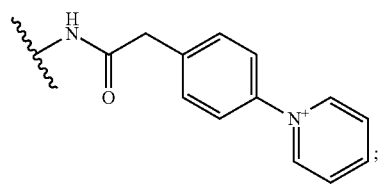 [SMILES: *NC(=O)Cc1ccc(-[n+]2ccccc2)cc1]

In certain embodiments, $L_1$ is —$CH_2$—C(=O)—NH—$(CH_2)_5$—C(=O)NH—$CH_2$—$C_6H_4$—$N^+(C_5H_5)$, where —$C_6H_4$—$N^+(C_5H_5)$ is p-pyridinium phenyl.

It will be appreciated that in addition to the coumarin (umbelliferone) aglycones defined above, other fluorescent aglycones can be utilized (e.g., fluoresceins, resorufins, rhodamines, nitrophenols, and 7-hydroxy-9H-(1,3-dichloro-9,9-dimethylacridin-2-ones, and their halogenated derivatives), as described below.

In certain embodiments, the Type A aglycone has the formula:

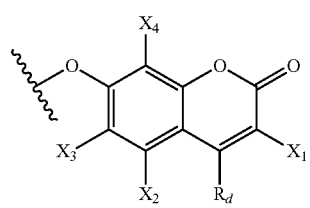

(MPS-II)

wherein $R_d$ is hydrogen or methyl, and $X_1$, $X_2$, $X_3$, and $X_4$ at each occurrence is independently hydrogen or halogen (e.g., chloro). In addition to the coumarin (umbelliferone) aglycone defined above, it will be appreciated that other fluorescent aglycones can be utilized. Suitable other aglycones include fluoresceins, resorufins, rhodamines, nitrophenols, and 7-hydroxy-9H-(1,3-dichloro-9,9-dimethylacridin-2-ones, and their halogenated derivatives. For the fluoresceins, resorufins, nitrophenols, and 7-hydroxy-9H-(1,3-dichloro-9,9-dimethylacridin-2-ones, the aglycone is coupled to the sugar through its hydroxy group as in the coumarins noted above. For the rhodamines, the aglycone is coupled to the sugar through its amino group.

Type A aglycone components can be included in the MPS reagents to impart fluorescent functionality (i.e., coumarin, umbelliferone, fluorescein, resorufin, nitrophenol, rhodamine, 7-hydroxy-9H-(1,3-dichloro-9,9-dimethylacridin-2-one moieties) and to provide reagents that can be analyzed by fluorescence techniques.

In one embodiment, the aglycone is a Type B aglycone and has the formula:

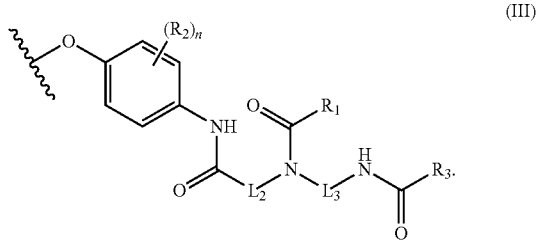

(III)

$L_2$ includes 1-20 carbon atoms (branched or linear) in which one or more carbon atoms may be replaced with a heteroatom (e.g., N, O, S) and/or one or more of the carbon atoms may be substituted (e.g., $C_1$-$C_6$ alkyl, halogen). In certain embodiments, $L_2$ is —$(CH_2)_n$—, where n is 1-6. In certain embodiments, $L_2$ is —$(CH_2)_2$—.

$L_3$ includes 1-20 carbon atoms (branched or linear) in which one or more carbon atoms may be replaced with a heteroatom (e.g., N, O, S) and/or one or more of the carbon atoms may be substituted (e.g., $C_1$-$C_6$ alkyl, halogen). In certain embodiments, $L_3$ is —$(CH_2)_m$—, where m is 1-12. In certain embodiments, $L_3$ is —$(CH_2)_m$—, where m is 4, 5, or 6.

$R_1$ is a $C_1$-$C_{10}$ alkyl group (e.g., branched or linear) or a $C_1$-$C_{10}$ alkoxy group (e.g., OtBu). In certain embodiments, $R_1$ is a $C_1$-$C_5$ alkyl group (e.g., methyl, ethyl, n-propyl, n-butyl, n-pentyl).

$R_2$ is at each occurrence is independently selected from a $C_1$-$C_{10}$ alkyl group (e.g., branched or linear), a $C_1$-$C_{10}$ alkoxy group (e.g., branched or linear), halogen (e.g., fluoro, chloro), nitro, —C(=O)NHR, or —C(=O)OR, where R is $C_1$-$C_8$ alkyl group (e.g., methyl), and n is 0, 1, 2, 3, or 4. Representative substitution patterns (relative to phenolic oxygen) for $R_2$ include 2-, 2,6-di, 3-, 3,5-di, and 2,3-di (i.e., 2- and 6-positions are ortho, and 3- and 5-positions are meta). In certain embodiments, $R_2$ is a fluoro, methyl, or methoxy group positioned either ortho or meta to the phenolic oxygen (e.g., 2-fluoro, 2-methyl, 2-methoxy, 3-fluoro, 3-methyl, 3-methoxy). In other embodiments, $R_2$ is a fluoro, methyl, or methoxy group positioned meta to the phenolic oxygen. In certain embodiments, n is zero and the phenylene group is unsubstituted.

$R_3$ is a $C_1$-$C_{10}$ alkyl group (e.g., branched or linear) or a substituted or unsubstituted $C_6$-$C_{10}$ aryl group (e.g., phenyl). Aryl groups substituents include a $C_1$-$C_{10}$ alkyl groups (e.g., branched or linear) and halogens (e.g., chloro). In certain embodiments, $R_3$ is a $C_1$-$C_6$ alkyl group (e.g., ethyl, n-propyl, n-butyl, n-pentyl). In other embodiments, $R_3$ is a phenyl group.

In certain embodiments, the Type B aglycone has the formula:

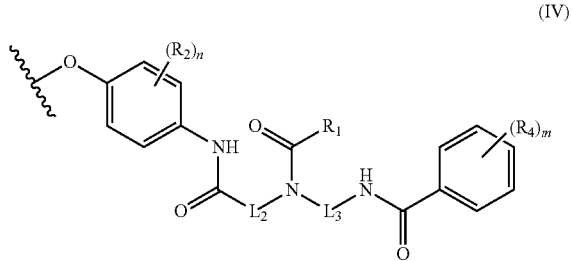

(IV)

wherein $L_2$, $L_3$, $R_1$, $R_2$, and n are as set forth above for formula (III), and $R_4$ at each occurrence is independently selected from $C_1$-$C_6$ alkyl (e.g., methyl) and m is 0, 1, 2, 3, 4, or 5. In certain embodiments, m is 0. In other embodiments, $R_4$ is a $C_1$-$C_5$ alkyl group (e.g., methyl) and m is 2.

In another embodiment, the Type B aglycone has the formula:

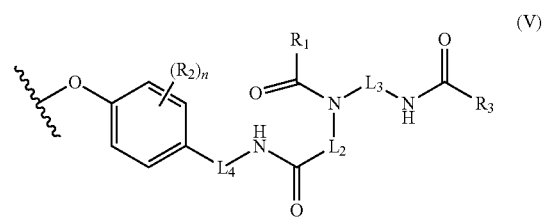

(V)

where $L_2$, $L_3$, $R_1$, $R_2$, $R_3$, and n are as set forth above for formula (III), and $L_4$ includes 1-20 carbon atoms (branched or linear) in which one or more carbon atoms may be replaced with a heteroatom (e.g., N, O, S) and/or one or more of the carbon atoms may be substituted (e.g., $C_1$-$C_6$ alkyl, halogen). In certain embodiments, $L_4$ is —$(CH_2)_n$—, where n is 1-6. In certain embodiments, $L_4$ is —$(CH_2)$—.

In certain embodiments, the Type B aglycone has the formula:

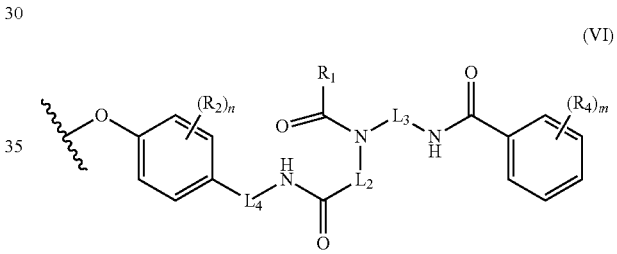

(VI)

where $L_2$, $L_3$, $L_4$, $R_1$, $R_2$, $R_4$, n, and m are as set forth above for formula (V).

Heavy Atom Derivatives.

In certain embodiments, the MPS reagents include their heavy atom derivatives (i.e., derivatives that include one or more heavy atom isotopes).

The heavy atom derivatives are useful as internal standards for assays utilizing mass spectrometric analysis. In certain embodiments, Type A and Type B aglycones have one or more (e.g., three or more) hydrogen atoms replaced with deuterium, or one or more (e.g., three or more) carbon atoms replaced with carbon-13 such that the mass of the aglycone is increased by one or more Daltons. As between an enzyme product and internal standard pair (e.g., MPS-II-P and MPS-II-IS), the reagents differ in mass and the difference in mass can be achieved through the use of additional (or fewer) atoms (e.g., changing the length of a portion of the compound by one or more methylenes for, for example, $L_1$, $L_2$, $L_3$, $L_4$, $R_1$, $R_2$, $R_3$, or $R_4$) or through the incorporation of heavy atoms (e.g., deuterium for hydrogen, $^{13}C$ for carbon, $^{15}N$ for nitrogen in, for example, $L_1$, $L_2$, $L_3$, $L_4$, $R_1$, $R_2$, $R_3$, or $R_4$).

Representative aglycones for substrate/internal standard pairs for MPS-I, II, IIIA, IIIB, IVA, VI, and VII reagents include the following:

for MPS-I substrate (referring to formula (IV)), $R_1$ is methyl, $R_2$ is hydrogen and n is 4, $L_2$ is —$CH_2CH_2$—, $L_3$ is —(CH$_2$)$_6$—, and R$_4$ is hydrogen and m is 5; for MPS-I internal standard, R$_1$ is methyl, R$_2$ is hydrogen and n is 4, L$_2$ is —CH$_2$CH$_2$—, L$_3$ is —(CH$_2$)$_6$—, and R$_4$ is deuterium and m is 5;

for MPS-II substrate (referring to formula (IV)), R$_1$ is n-butyl, R$_2$ is hydrogen and n is 4, L$_2$ is —CH$_2$CH$_2$—, L$_3$ is —(CH$_2$)$_6$—, and R$_4$ is hydrogen and m is 5; for MPS-II internal standard, R$_1$ is n-butyl, R$_2$ is hydrogen and n is 4, L$_2$ is —CH$_2$CH$_2$—, L$_3$ is —(CH$_2$)$_6$—, and R$_4$ is deuterium and m is 5;

for MPS-IIIA substrate (referring to formula (IV)), R$_1$ is ethyl, R$_2$ is hydrogen and n is 4, L$_2$ is —CH$_2$CH$_2$—, L$_3$ is —(CH$_2$)$_6$—, and R$_4$ is hydrogen and m is 5; for MPS-IIIA internal standard, R$_1$ is ethyl, R$_2$ is hydrogen and n is 4, L$_2$ is —CH$_2$CH$_2$—, L$_3$ is —(CH$_2$)$_6$—, R$_4$ is deuterium and m is 5;

for MPS-IIIB substrate (referring to formula (III)), R$_1$ is n-butyl, R$_2$ is hydrogen and n is 4, L$_2$ is —CH$_2$CH$_2$—, L$_3$ is —(CH$_2$)$_6$—, and R$_3$ is ethyl; for MPS-IIIB internal standard, R$_1$ is n-butyl, R$_2$ is deuterium and n is 4, L$_2$ is —CH$_2$CH$_2$—, L$_3$ is —(CH$_2$)$_6$—, R$_3$ is ethyl;

for MPS-IVA substrate (referring to formula (III)), R$_1$ is n-butyl, R$_2$ is hydrogen and n is 4, L$_2$ is —CH$_2$CH$_2$—, L$_3$ is —(CH$_2$)$_5$—, and R$_3$ is 3,5-dimethylphenyl; for MPS-IVA internal standard, R$_1$ is n-butyl, L$_2$ is —CH$_2$CH$_2$—, L$_3$ is —(CH$_2$)$_5$—, R$_3$ is 3,5-dimethylphenyl, and R$_2$ is deuterium and n is 4; and in an alternative embodiment, for MPS-IVA substrate, R$_1$ is n-pentyl, R$_2$ is hydrogen and n is 4, L$_2$ is —CH$_2$CH$_2$—, L$_3$ is —(CH$_2$)$_6$—, and R$_3$ is phenyl; for MPS-IVA internal standard, R$_1$ is n-pentyl, R$_2$ is hydrogen and n is 4, L$_2$ is —CH$_2$CH$_2$—, L$_3$ is —(CH$_2$)$_6$—, R$_3$ is d$_5$-phenyl;

for MPS-VI substrate (referring to formula (IV)), R$_1$ is n-butyl, R$_2$ is hydrogen and n is 4, L$_2$ is —CH$_2$CH$_2$—, L$_3$ is —(CH$_2$)$_5$—, and R$_4$ is hydrogen and m is 5; for MPS-VI internal standard, R$_1$ is n-butyl, R$_2$ is hydrogen and n is 4, L$_2$ is —CH$_2$CH$_2$—, L$_3$ is —(CH$_2$)$_5$—, and R$_4$ is deuterium and m is 5; and for MPS-VII substrate (referring to formula (III)), R$_1$ is butyl, R$_2$ is hydrogen and n is 4, L$_2$ is —CH$_2$CH$_2$—, L$_3$ is —(CH$_2$)$_6$—, and R$_3$ is propyl; for MPS-VII internal standard, R$_1$ is butyl, R$_2$ is deuterium and n is 4, L$_2$ is —CH$_2$CH$_2$—, L$_3$ is —(CH$_2$)$_6$—, and R$_3$ is propyl.

Salts.

In certain embodiments, the reagents include amino groups (e.g., —NH$_2$), carboxylic acid groups (—CO$_2$H), sulfonic acid groups (e.g., —OSO$_3$H), and amidosulfonic acid groups (e.g., —NHSO$_3$H), which depending on the pH environment can become charged groups (e.g., —NH$_3^+$, —CO$_2^-$, —OSO$_3^-$, —NHSO$_3^-$). It will be appreciated that the reagents of the disclosure include their salts (e.g., metal salts).

The preparation of representative MPS-I, II, IIIA, IIIB, IVA, and VI reagents are described in Examples 1, 4, and 5.

The following is a description of representative MPS reagents (i.e., compounds).

MPS-I Reagents

In one embodiment, the MPS-I reagents (S, P, and IS reagents) are defined by the following formula:

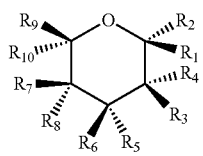

its salts and heavy atom derivatives thereof,
wherein
R$_1$=aglycone, R$_2$=H
or
R$_1$=H, R$_2$=aglycone
R$_3$=H, OH, NH$_2$ and R$_4$=H
or
R$_4$=H, OH, NH$_2$ and R$_3$=H
R$_5$=H, OH, NH$_2$ and R$_6$=H
or
R$_6$=H, OH, NH$_2$ and R$_5$=H
R$_7$=H, OH, NH$_2$ and R$_8$=H
or
R$_8$=H, OH, NH$_2$ and R$_7$=H
R$_9$=COOH and R$_{10}$=H
or
R$_{10}$=COOH and R$_9$=H
with the proviso that only one of the pair of R$_3$ and R$_4$, R$_5$ and R$_6$, and R$_7$ and R$_8$ can have each R group as hydrogen (i.e., the carbohydrate ring can include only a single methylene group (—CH$_2$—) in the ring).

For the above compounds, the aglycone is as described above.

In certain embodiments of the MPS-I reagents defined above, the carbohydrate portion is replaced by a hydrogen atom; in this case a hydrogen atom is added to the aglycone. These reagents are representative of MPS-I enzyme products and internal standards.

In one embodiment, the sugar has the formula:

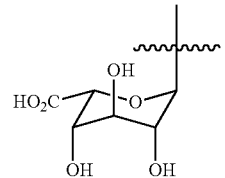 [SMILES: *C1OC(C(=O)O)C(O)C(O)C1O]

In certain embodiments, the compounds include amino groups (e.g., —NH$_2$) and carboxylic acid groups (—CO$_2$H), which depending on the pH environment can become charged groups (e.g., —NH$_3^+$ or —CO$_2^-$). It will be appreciated that the MPS compounds include their salts (e.g., metal salts).

As noted above, the compounds of the disclosure include their heavy atom derivatives. The heavy atom derivatives are useful as internal standards. In certain embodiments, Type A and Type B aglycones have one or more (e.g., three or more) hydrogen atoms replaced with deuterium, or one or more (e.g., three or more) carbon atoms replaced with carbon-13 such that the mass of the aglycone is increased by one or more Daltons. The enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}$C for carbon, $^{15}$N for nitrogen).

In certain embodiments of the MPS-I reagents defined above, the carbohydrate portion is replaced by a hydrogen atom; in this case a hydrogen atom is added to the aglycone. These reagents are representative of MPS-I enzyme products and internal standards.

Representative MPS-I reagents include the following compounds.

In certain embodiments, MPS-I substrates have the formula:

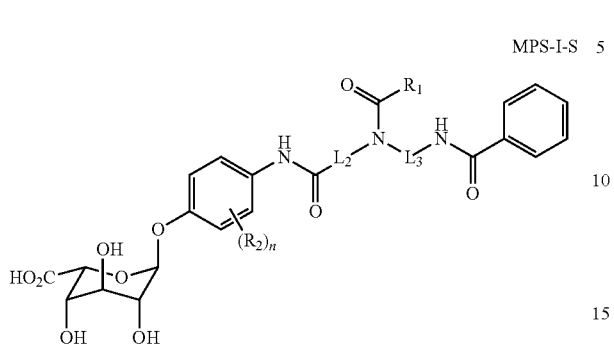
MPS-I-S where $L_2$, $L_3$, $R_1$, $R_2$, and n are as described above for formula (III).

In certain embodiments, MPS-I substrates have the formula:

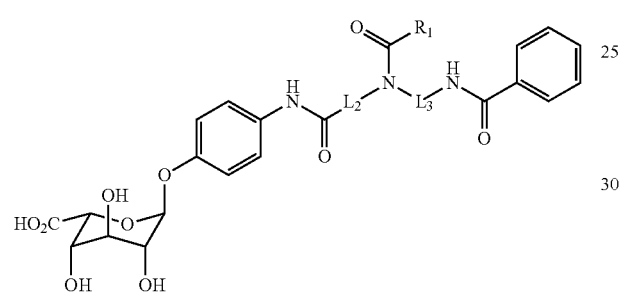

where $L_2$, $L_3$, and $R_1$ are as described above for formula (III).

A representative MPS-I substrate has the formula:

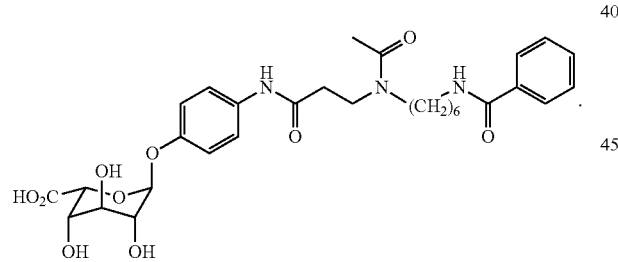

MPS-I products formed from the above substrate (MPS-I-S) have the formula:

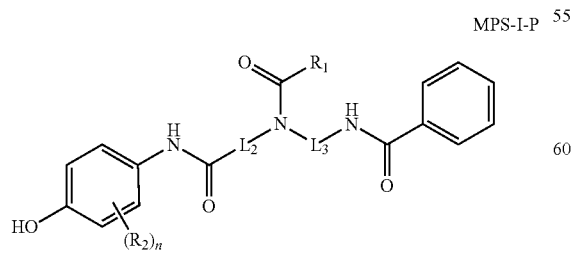
MPS-I-P where $L_2$, $L_3$, $R_1$, $R_2$, and n are as described above for formula (III).

A representative MPS-I product has the formula:

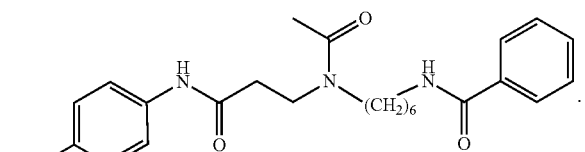

MPS-I internal standards useful for assaying products formed from the above substrate (MPS-I-S) have the formula:

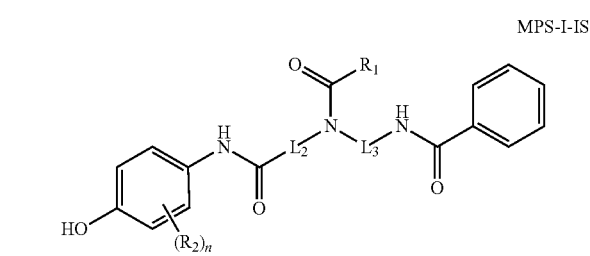
MPS-I-IS where $L_2$, $L_3$, $R_1$, $R_2$, and n are as described above for formula (III), and where the mass of MPS-I-IS differs from the mass of MPS-I-P such that the two are distinguishable by mass spectrometry. As noted above, MPS-I-IS can include one or more heavy atom isotopes (not shown in the structure above), or can have a structural variation (e.g., one or more of $L_2$, $L_3$, $R_1$, and $R_2$ for substrate differ from $L_2$, $L_3$, $R_1$, and $R_2$ for internal standard).

A representative MPS-I internal standard has the formula:

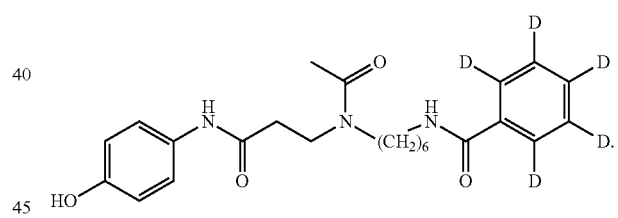

The representative MPS-I product derived from the representative MPS-I substrate can be assayed using the representative MPS-I internal standard.

MPS-II Reagents

In one embodiment, the MPS-II reagents (S, P, and IS reagents) are defined by the following formula:

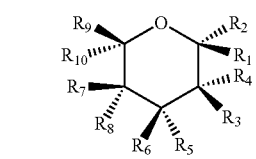

its salts and heavy atom derivatives thereof,
wherein
$R_1$=aglycone, $R_2$=H
or
$R_1$=H, $R_2$=aglycone
$R_3$=OSO$_3$H, NHSO$_3$H and $R_4$=H or
$R_4$=$OSO_3H$, $NHSO_3H$ and $R_3$=H
$R_5$=H, OH, $NH_2$ and $R_6$=H
or
$R_6$=H, OH, $NH_2$ and $R_5$=H
$R_7$=H, OH, $NH_2$ and $R_8$=H
or
$R_8$=H, OH, $NH_2$ and $R_7$=H
$R_9$=COOH and $R_{10}$=H
or
$R_{10}$=COOH and $R_9$=H
with the proviso that only one of the pair of $R_5$ and $R_6$, and $R_7$ and $R_8$ can have each R group as hydrogen (i.e., the carbohydrate ring can include only a single methylene group (—$CH_2$—) in the ring).

For the above compounds, the aglycone is as described above.

In one embodiment, the sugar has the formula:

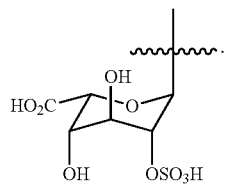

In another embodiment, the sugar has the formula:

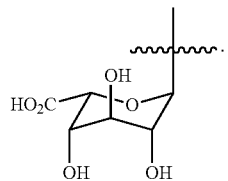

In certain embodiments, the compounds include amino groups (e.g., —$NH_2$), carboxylic acid groups (—$CO_2H$), and sulfonic acid groups (e.g., —$OSO_3H$), which depending on the pH environment can become charged groups (e.g., —$NH_3^+$, —$CO_2^-$, —$OSO_3^-$). It will be appreciated that the compounds of the disclosure include their salts (e.g., metal salts).

As noted above, the compounds of the disclosure include their heavy atom derivatives. The heavy atom derivatives are useful as internal standards. In further embodiments, Type A and Type B aglycones have one or more (e.g., three or more) hydrogen atoms replaced with deuterium, or one or more (e.g., three or more) carbon atoms replaced with carbon-13 such that the mass of the aglycone is increased by one or more Daltons. The enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

The MPS-II enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

Representative MPS-II reagents include the following compounds.

In certain embodiments, MPS-II substrates have the formula:

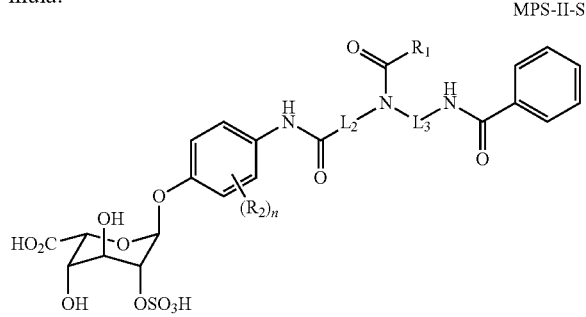

MPS-II-S where $L_2$, $L_3$, $R_1$, $R_2$, and n are as described above for formula (III).

In certain embodiments, MPS-II substrates have the formula:

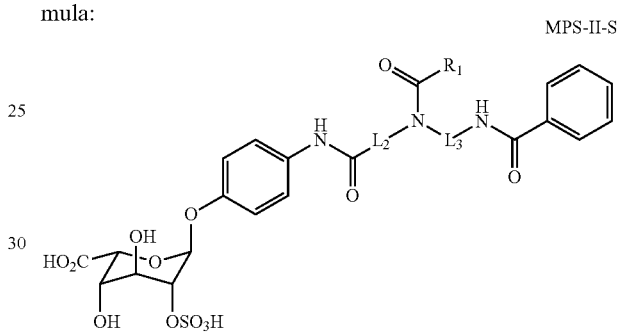

MPS-II-S where $L_2$, $L_3$, and $R_1$ are as described above for formula (III).

A representative MPS-II substrate has the formula:

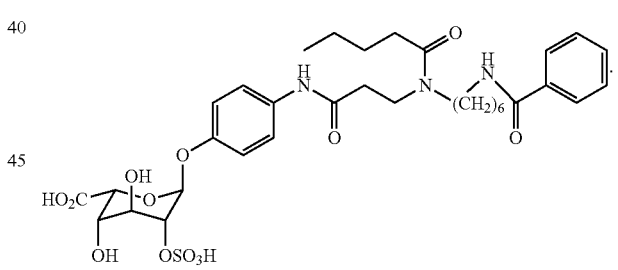

MPS-II products formed from the above substrate (MPS-II-S) have the formula:

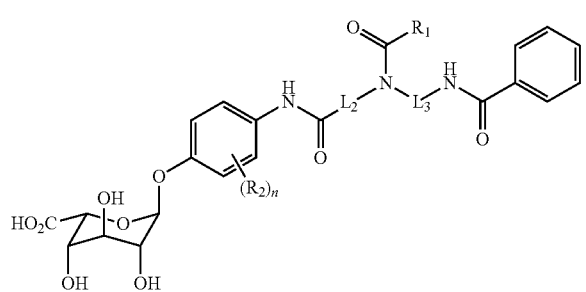

MPS-II-P where $L_2$, $L_3$, $R_1$, $R_2$, and n are as described above for formula (III).

A representative MPS-II product has the formula:

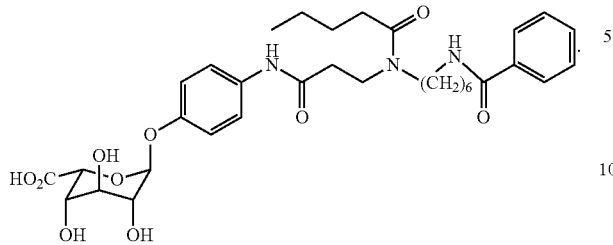

MPS-II internal standards useful for assaying products formed from the above substrate (MPS-II-S) have the formula:

MPS-II-IS

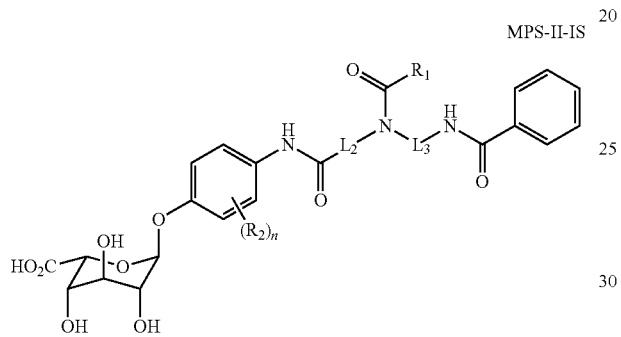

where $L_2$, $L_3$, $R_1$, $R_2$, and n are as described above for formula (III), and where the mass of MPS-II-IS differs from the mass of MPS-II-P such that the two are distinguishable by mass spectrometry. As noted above, MPS-II-IS can include one or more heavy atom isotopes (not shown in the structure above), or can have a structural variation (e.g., one or more of $L_2$, $L_3$, $R_1$, or $R_2$ for substrate differ from $L_2$, $L_3$, $R_1$, or $R_2$ for internal standard).

A representative MPS-II internal standard has the formula:

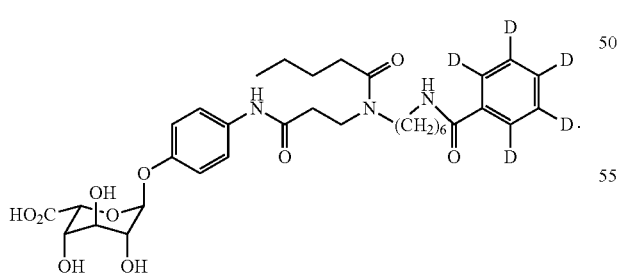

The representative MPS-II product derived from the representative MPS-II substrate can be assayed using the representative MPS-II internal standard.

MPS-IIIA Reagents

In another embodiment, the MPS-IIIA reagents (S, P, and IS reagents) are defined by the following formula:

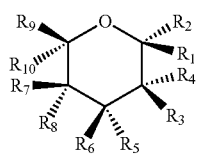

$R_1$=aglycone, $R_2$=H
or
$R_1$=H, $R_2$=aglycone
$R_3$=H, OH, $NH_2$, $NHSO_3H$, $OSO_3H$ and $R_4$=H
or
$R_4$=H, OH, $NH_2$, $NHSO_3H$, $OSO_3H$ and $R_3$=H
$R_5$=H, OH, $NH_2$ and $R_6$=H
or
$R_6$=H, OH, $NH_2$ and $R_5$=H
$R_7$=H, OH, $NH_2$ and $R_8$=H
or
$R_8$=H, OH, $NH_2$ and $R_7$=H
$R_9$=$CH_2OH$, $CH_2NH_2$ and $R_{10}$=H
or
$R_{10}$=$CH_2OH$, $CH_2NH_2$ and $R_9$=H
its salts and heavy atom derivatives thereof,
wherein the aglycone is as described above, and
with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

In one embodiment, the sugar has the formula:

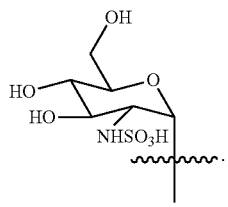

In another embodiment, the sugar has the formula:

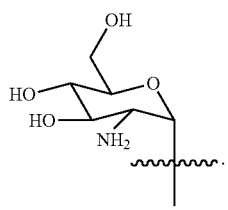 [SMILES: *C1OC(CO)C(O)C(O)C1N]

In certain embodiments, the compounds include amino groups (e.g., —$NH_2$) and amidosulfonic acid groups (e.g., —$NHSO_3H$), which depending on the pH environment can become charged groups (e.g., —$NH_3^+$, —$NHSO_3^-$). It will be appreciated that the compounds of the disclosure include their salts (e.g., metal salts).

The MPS-IIIA enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

Representative MPS-IIIA reagents include the following compounds.

In certain embodiments, MPS-IIIA substrates have the formula:

MPS-IIIA-S

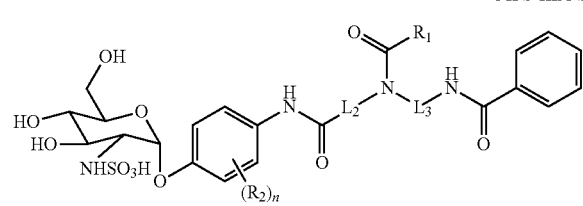

where $L_2$, $L_3$, $R_1$, $R_2$, and n are as described above for formula (III).

In certain embodiments, MPS-IIIA substrates have the formula:

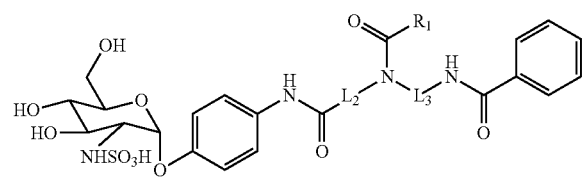

where $L_2$, $L_3$, and $R_1$ are as described above for formula (III).

A representative MPS-IIIA substrate has the formula:

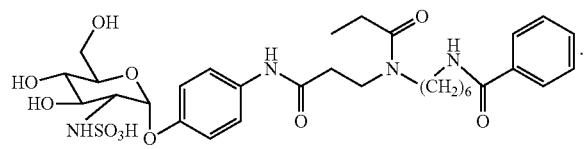

MPS-IIIA products formed from the above substrate (MPS-IIIA-S) have the formula:

MPS-IIIA-P

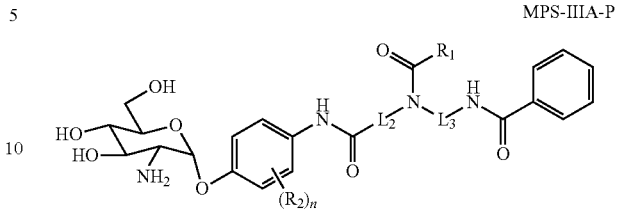

where $L_2$, $L_3$, $R_1$, $R_2$, and n are as described above for formula (III).

A representative MPS-IIIA product has the formula:

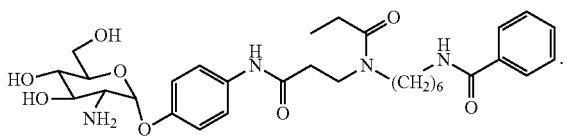

MPS-IIIA internal standards useful for assaying products formed from the above substrate (MPS-IIIA-S) have the formula:

MPS-IIIA-IS

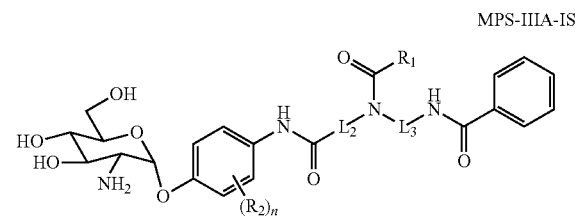

where $L_2$, $L_3$, $R_1$, $R_2$, and n are as described above for formula (III), and where the mass of MPS-IIIA-IS differs from the mass of MPS-IIIA-P such that the two are distinguishable by mass spectrometry. As noted above, MPS-IIIA-IS can include one or more heavy atom isotopes (not shown in the structure above), or can have a structural variation (e.g., one or more of $L_2$, $L_3$, $R_1$, $R_2$ for substrate differ from $L_2$, $L_3$, $R_1$, $R_2$ for internal standard).

A representative MPS-IIIA internal standard has the formula:

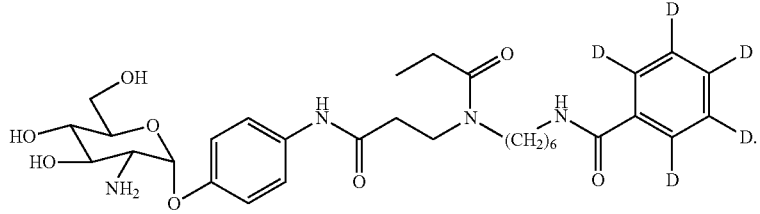

The representative MPS-IIIA product derived from the representative MPS-IIIA substrate can be assayed using the representative MPS-IIIA internal standard.

MPS-IIIB Reagents

In a further embodiment, the disclosure provides MPS-IIIB reagents (S, P, and IS reagents) defined by the following formula:

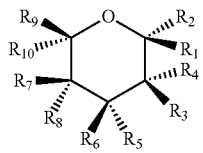

$R_1$=aglycone, $R_2$=H
or
$R_1$=H, $R_2$=aglycone
$R_3$=H, OH, $NH_2$, $NHR_{11}$, where $R_{11}$=formyl, acetyl, C=O(($CH_2$)$_n$$CH_3$) with n=1-6 and $R_4$=H
or
$R_4$=H, OH, $NH_2$, $NHR_{11}$, where $R_{11}$=formyl, acetyl, C=O(($CH_2$)$_n$$CH_3$) with n=1-6 and $R_3$=H
$R_5$=H, OH, $NH_2$ and $R_6$=H
or
$R_6$=H, OH, $NH_2$ and $R_5$=H
$R_7$=H, OH, $NH_2$ and $R_8$=H
or
$R_8$=H, OH, $NH_2$ and $R_7$=H
$R_9$=$CH_2OH$, $CH_2NH_2$ and $R_{10}$=H
or
$R_{10}$=$CH_2OH$, $CH_2NH_2$ and $R_{10}$=H
its salts and heavy atom derivatives thereof,
wherein the aglycone is as described above, and
with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

In certain embodiments of the MPS-IIIB reagents defined above, the carbohydrate portion is replaced by a hydrogen atom; in this case a hydrogen atom is added to the aglycone. These reagents are representative of MPS-IIIB enzyme products and internal standards.

In one embodiment, the sugar has the formula:

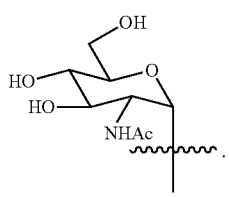

In the above formula, "NHAc" refers to "NH—C(=O)$CH_3$."

In certain embodiments, the compounds include amino groups (e.g., —$NH_2^+$), which depending on the pH environment can become charged groups (e.g., —$NH_3^+$). It will be appreciated that the compounds of the disclosure include their salts (e.g., metal salts).

The MPS-IIIB enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

Representative MPS-IIIB reagents include the following compounds.

In certain embodiments, MPS-IIIB substrates have the formula:

MPS-IIIB-S

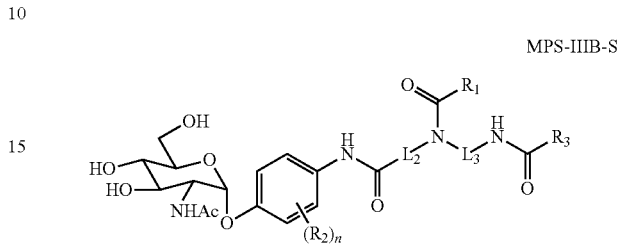

where $L_2$, $L_3$, $R_1$, $R_2$, $R_3$, and n are as described above for formula (III).

In certain embodiments, MPS-IIIB substrates have the formula:

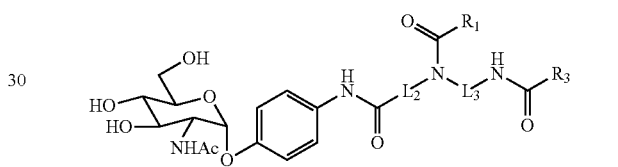

where $L_2$, $L_3$, $R_1$, and $R_3$ are as described above for formula (III).

A representative MPS-IIIB substrate has the formula:

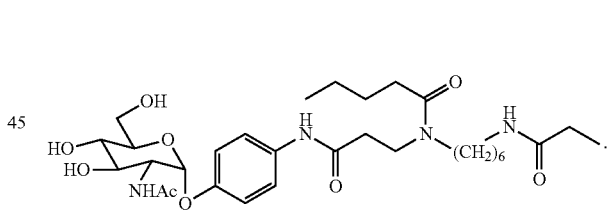

MPS-IIIB products formed from the above substrate (MPS-IIIB-S) have the formula:

MPS-IIIB-P

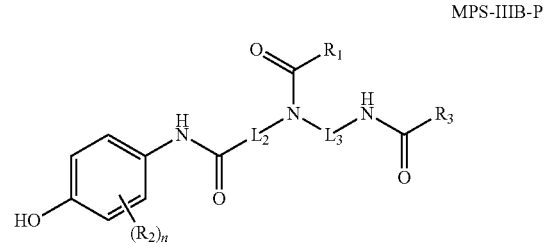

where $L_2$, $L_3$, $R_1$, $R_2$, $R_3$, and n are as described above for formula (III).

A representative MPS-IIIB product has the formula:

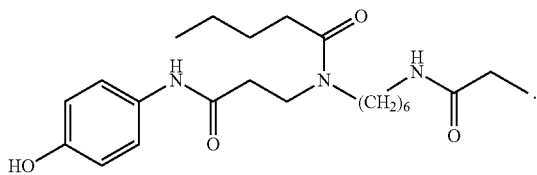

MPS-IIIB internal standards useful for assaying products formed from the above substrate (MPS-IIIB-S) have the formula:

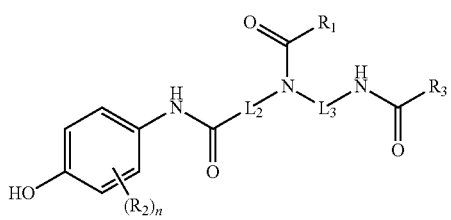

MPS-IIIB-IS where $L_2$, $L_3$, $R_1$, $R_2$, $R_3$, and n are as described above for formula (III), and where the mass of MPS-IIIB-IS differs from the mass of MPS-IIIB-P such that the two are distinguishable by mass spectrometry. As noted above, MPS-IIIB-IS can include one or more heavy atom isotopes (not shown in the structure above), or can have a structural variation (e.g., one or more of $L_2$, $L_3$, $R_1$, $R_2$, or $R_3$ for substrate differ from $L_2$, $L_3$, $R_1$, $R_2$, or $R_3$ for internal standard).

A representative MPS-IIIB internal standard has the formula:

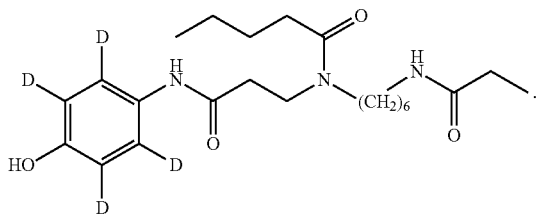

The representative MPS-IIIB product derived from the representative MPS-IIIB substrate can be assayed using the representative MPS-IIIB internal standard.

MPS-IVA Reagents

In another embodiment, the MPS-IVA reagents (S, P, and IS reagents) are defined by the following formula:

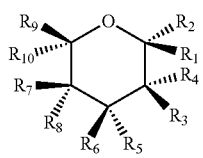

$R_1$=aglycone, $R_2$=H
or
$R_1$=H, $R_2$=aglycone $R_3$=H, OH, $NH_2$, $NHR_{11}$, where $R_{11}$=formyl, acetyl, $C\!=\!O((CH_2)_n CH_3)$ with n=1-6 and $R_4$=H
or
$R_4$=H, OH, $NH_2$, $NHR_{11}$, where $R_{11}$=formyl, acetyl, $C\!=\!O((CH_2)_n CH_3)$ with n=1-6 and $R_3$=H
$R_5$=H, OH, $NH_2$ and $R_6$=H
or
$R_6$=H, OH, $NH_2$ and $R_5$=H
$R_7$=H, OH, $NH_2$ and $R_8$=H
or
$R_8$=H, OH, $NH_2$ and $R_7$=H
$R_9$=$CH_2OH$, $CH_2OSO_3H$, $CH_2NH_2$, $CH_2NHSO_3H$ and $R_{10}$=H
or
$R_{10}$=$CH_2OH$, $CH_2OSO_3H$, $CH_2NH_2$, $CH_2NHSO_3H$ and $R_9$=H
its salts and heavy atom derivatives thereof,
wherein the aglycone is as described above, and
with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

In one embodiment, the sugar has the formula:

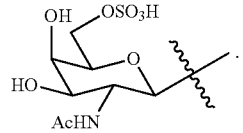

In certain embodiments, the compounds include amino groups (e.g., —$NH_2$) and sulfonic acid groups (e.g., —$OSO_3H$), which depending on the pH environment can become charged groups (e.g., —$NH_3^+$, —$OSO_3^-$). It will be appreciated that the compounds of the disclosure include their salts (e.g., metal salts).

The MPS-IVA enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

Representative MPS-IVA reagents include the following compounds.

In certain embodiments, MPS-IVA substrates have the formula:

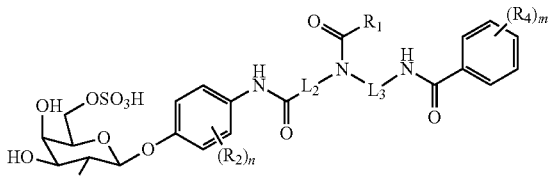

MPS-IVA-S1 where $L_2$, $L_3$, $R_1$, $R_2$, and n are as described above for formula (III). $R_4$ at each occurrence is independently selected from $C_1$-$C_6$ alkyl (e.g., methyl) and m is 0, 1, 2, 3, 4, or 5.

In other embodiments, MPS-IVA substrates have the formula:

MPS-IVA-S2

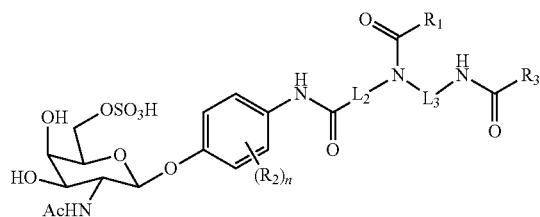

where $L_2$, $L_3$, $R_1$, $R_2$, $R_3$, and n are as described above for formula (III).

In certain embodiments, MPS-IVA substrates have the formula:

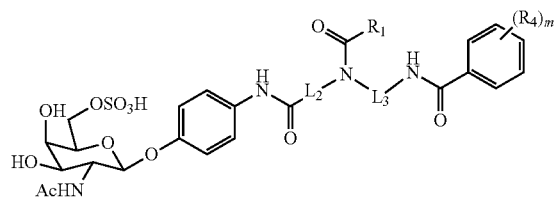

where $L_2$, $L_3$, $R_1$, $R_4$, and m are as described above for formula (IV).

In other embodiments, MPS-IVA substrates have the formula:

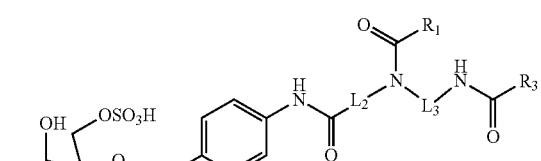

where $L_2$, $L_3$, $R_1$, and $R_3$ are as described above for formula (III).

A representative MPS-IVA substrate has the formula:

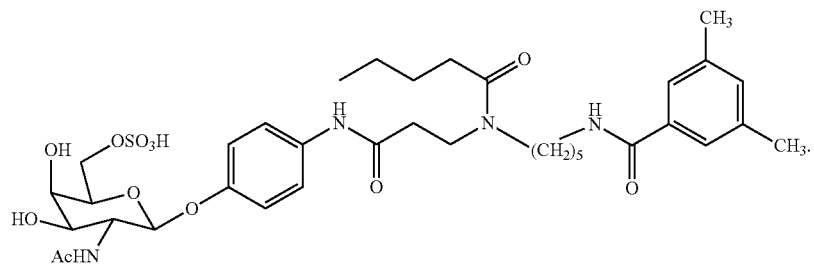

Another representative MPS-IVA substrate has the formula:

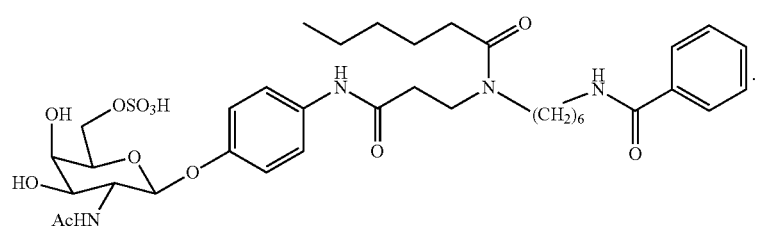

MPS-IVA products formed from the above substrate (MPS-IVA-S1) have the formula:

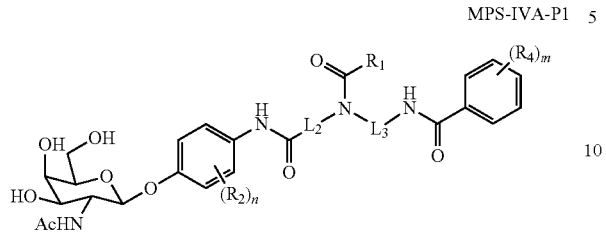
MPS-IVA-P1 where $L_2$, $L_3$, $R_1$, $R_2$, $R_4$, n, and m are as described above in formula (IV).

In another embodiment, MPS-IVA products formed from the above substrate (MPS-IVA-S2) have the formula:

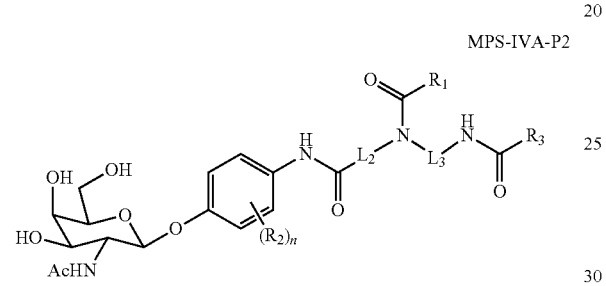
MPS-IVA-P2 where $L_2$, $L_3$, $R_1$, and $R_3$ are as described above for formula (III).

A representative MPS-IVA product has the formula:

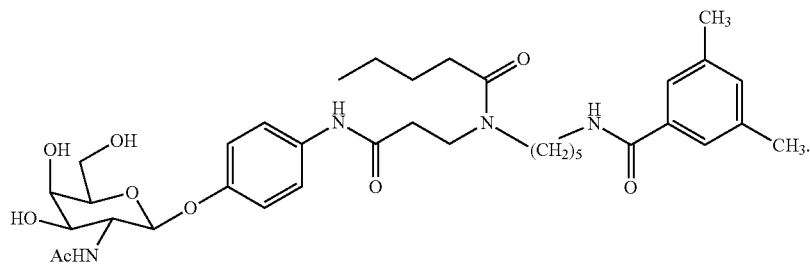

Another representative MPS-IVA product has the formula:

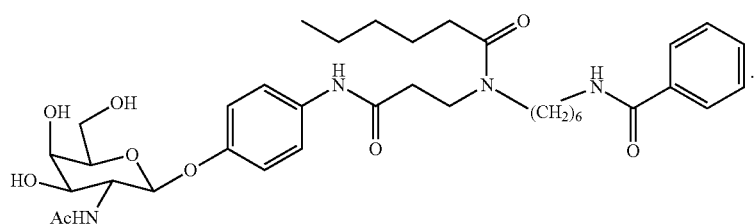

MPS-IVA internal standards useful for assaying products formed from the above substrates (MPS-IVA-S1 and MPS-IVA-S2) have the formulae:

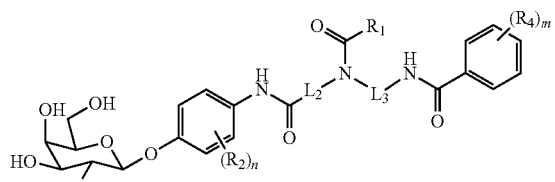
MPS-IVA-IS1 and

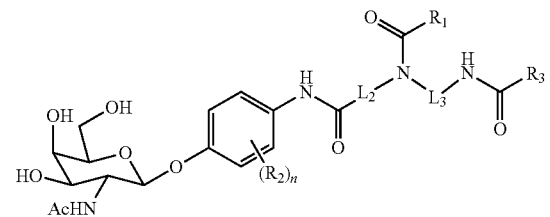
MPS-IVA-IS2 where $L_2$, $L_3$, $R_1$, $R_2$, $R_3$, $R_4$, n, and m are as described above, and the masses of MPS-IVA-IS1 and MPS-IVA-IS2 differ from the masses of MPS-IVA-P1 and MPS-IVA-P2, respectively, such that the two are distinguishable by mass spectrometry. As noted above, MPS-IVA-IS1 and MPS-IVA-IS2 can include one or more heavy atom isotopes (not shown in the structure above), or can have a structural variation (e.g., one or more of $L_2$, $L_3$, $R_1$, $R_2$, $R_3$, or $R_4$ for substrate differ from $L_2$, $L_3$, $R_1$, $R_2$, $R_3$, or $R_4$ for internal standard).

A representative MPS-IVA internal standard has the formula:

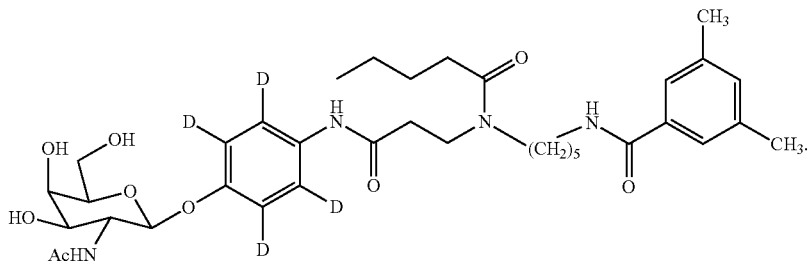

Another representative MPS-IVA internal standard has the formula:

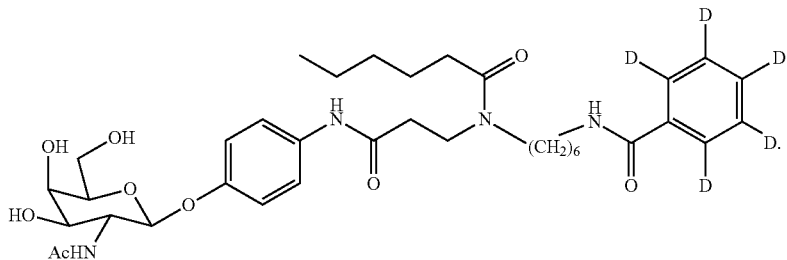

Representative MPS-IVA products derived from the representative MPS-IVA substrates can be assayed using the representative MPS-IVA internal standards.

A further representative set of MPS-IVA reagents is described below.

A further representative MPS-IVA substrate has the formula:

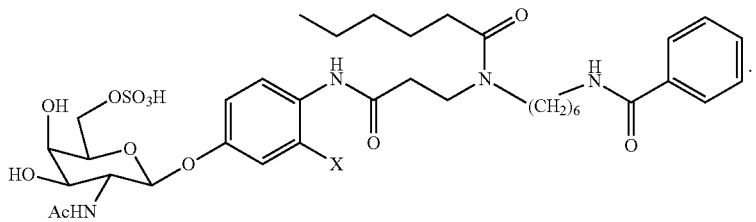

A further representative MPS-IVA product standard has the formula:

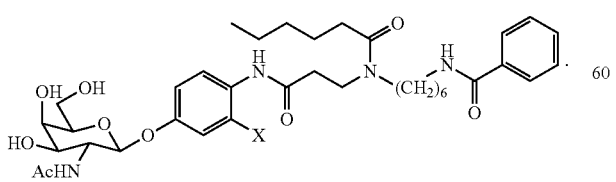

A further representative MPS-IVA internal standard has the formula:

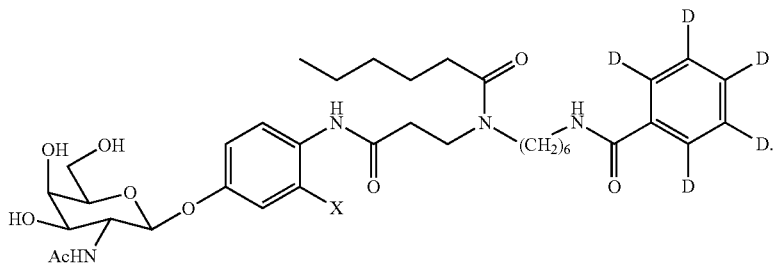

In the above formulas, X is selected from fluoro, methyl, and methoxy.

MPS-VI Reagents

In another embodiment, the MPS-VI reagents (S, P, and IS reagents) are defined by the following formula:

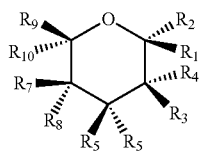

$R_1$=aglycone, $R_2$=H or $R_1$=H, $R_2$=aglycone $R_3$=H, OH, $NH_2$, $NHR_{11}$, where $R_{11}$=formyl, acetyl, $C=O((CH_2)_nCH_3)$ with n=1-6 and $R_4$=H or $R_4$=H, OH, $NH_2$, $NHR_{11}$, where $R_{11}$=formyl, acetyl, $C=O((CH_2)_nCH_3)$ with n=1-6 and $R_3$=H $R_5$=H, OH, $NH_2$ and $R_6$=H or $R_6$=H, OH, $NH_2$ and $R_5$=H $R_7$=$CH_2OH$, $CH_2OSO_3H$, $CH_2NH_2$, $CH_2NHSO_3H$ and $R_8$=H or $R_8$=$CH_2OH$, $CH_2OSO_3H$, $CH_2NH_2$, $CH_2NHSO_3H$ and $R_7$=H $R_9$=$CH_2OH$, $CH_2NH_2$ and $R_{10}$=H or $R_{10}$=$CH_2OH$, $CH_2NH_2$ and $R_9$=H its salts and heavy atom derivatives thereof, wherein the aglycone is as described above, and with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

In one embodiment, the sugar has the formula:

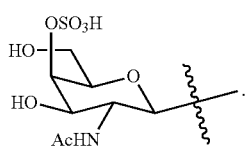

In another embodiment, the sugar has the formula:

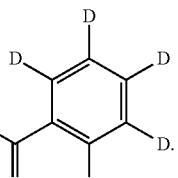

In the above formulas, "AcNH" refers to "$CH_3C(=O)NH$."

In certain embodiments, the compounds include amino groups (e.g., —$NH_2$) and sulfonic acid groups (e.g., —$OSO_3H$), which depending on the pH environment can become charged groups (e.g., —$NH_3^+$, —$OSO_3^-$). It will be appreciated that the compounds of the disclosure include their salts (e.g., metal salts).

The MPS-VI enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

Representative MPS-VI reagents include the following compounds.

In certain embodiments, MPS-VI substrates have the formula:

MPS-VI-S

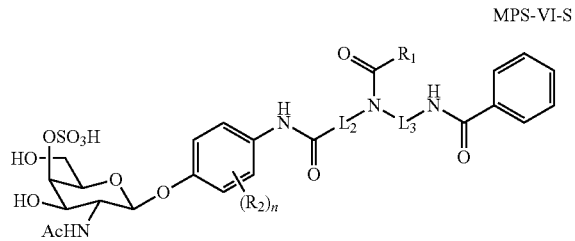

where $L_2$, $L_3$, $R_1$, $R_2$, and n are as described above for formula (III).

In certain embodiments, MPS-VI substrates have the formula:

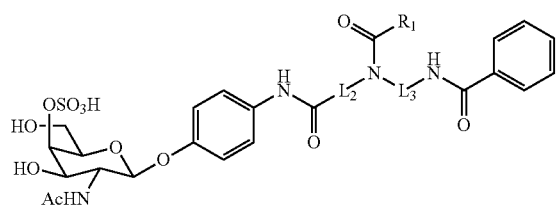

where $L_2$, $L_3$, and $R_1$ are as described above for formula (III).

A representative MPS-VI substrate has the formula:

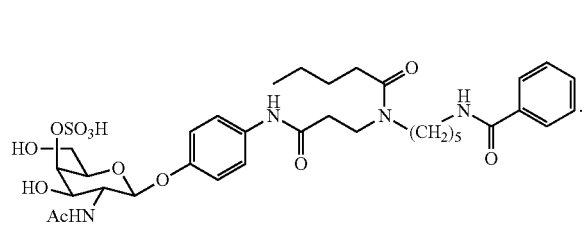

MPS-VI products formed from the above substrate (MPS-VI-S) have the formula:

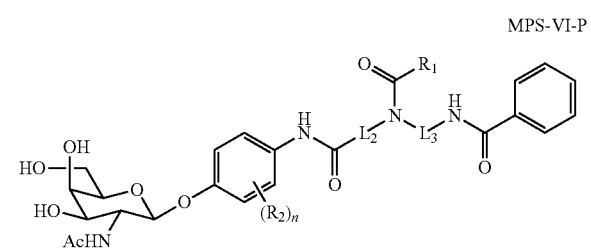

where $L_2$, $L_3$, $R_1$, $R_2$, and n are as described above for formula (III).

A representative MPS-VI product has the formula:

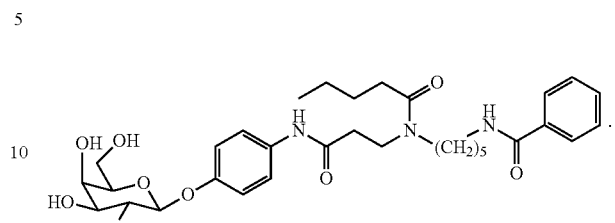

MPS-VI internal standards useful for assaying products formed from the above substrate (MPS-VI-S) have the formula:

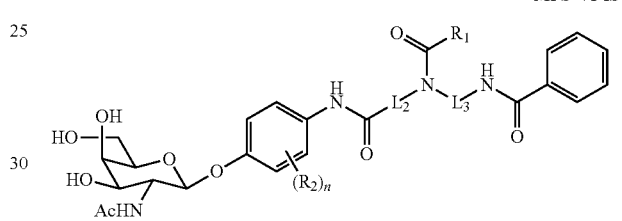

where $L_2$, $L_3$, $R_1$, $R_2$, and n are as described above for formula (III), and where the mass of MPS-VI-IS differs from the mass of MPS-VI-P such that the two are distinguishable by mass spectrometry. As noted above, MPS-VI-IS can include one or more heavy atom isotopes (not shown in the structure above), or can have a structural variation (e.g., one or more of $L_2$, $L_3$, $R_1$, or $R_2$ for substrate differ from $L_2$, $L_3$, $R_1$, or $R_2$ for internal standard).

A representative MPS-VI internal standard has the formula:

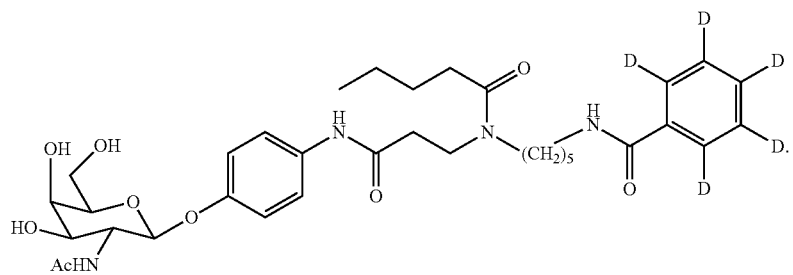

The representative MPS-VI product derived from the representative MPS-VI substrate can be assayed using the representative MPS-VI internal standard.

MPS-VII Reagents

In one embodiment, the MPS-VII reagents (S, P, and IS reagents) are defined by the following formula:

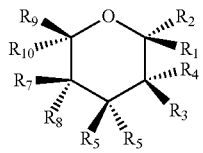

its salts and heavy atom derivatives thereof, wherein
$R_1$=aglycone, $R_2$=H
or
$R_1$=H, $R_2$=aglycone
$R_3$=H, OH, $NH_2$ and $R_4$=H
or
$R_4$=H, OH, $NH_2$ and $R_3$=H
$R_5$=H, OH, $NH_2$ and $R_6$=H
or
$R_6$=H, OH, $NH_2$ and $R_5$=H
$R_7$=H, OH, $NH_2$ and $R_8$=H
or
$R_8$=H, OH, $NH_2$ and $R_7$=H
$R_9$=COOH and $R_{10}$=H
or
$R_{10}$=COOH and $R_9$=H
with the proviso that only one of the pair of $R_3$ and $R_4$, $R_5$ and $R_6$, and $R_7$ and $R_8$ can have each R group as hydrogen (i.e., the carbohydrate ring can include only a single methylene group (—$CH_2$—) in the ring).

For the above compounds, the aglycone is as described above.

In certain embodiments of the MPS-VII reagents defined above, the carbohydrate portion is replaced by a hydrogen atom; in this case a hydrogen atom is added to the aglycone. These reagents are representative of MPS-VII enzyme products and internal standards.

In one embodiment, the sugar has the formula:

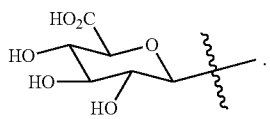

In certain embodiments, the compounds include amino groups (e.g., —$NH_2$) and carboxylic acid groups (—$CO_2H$), which depending on the pH environment can become charged groups (e.g., —$NH_3^+$ or —$CO_2^-$). It will be appreciated that the compounds of the disclosure include their salts (e.g., metal salts).

As noted above, the compounds of the disclosure include their heavy atom derivatives. The heavy atom derivatives are useful as internal standards. In certain embodiments, Type A and Type B aglycones have one or more (e.g., three or more) hydrogen atoms replaced with deuterium, or one or more (e.g., three or more) carbon atoms replaced with carbon-13 such that the mass of the aglycone is increased by one or more Daltons. The enzyme products and internal standards differ in mass and the difference in mass can be achieved through the use of additional atoms (e.g., changing the length of a portion of the compound by one or more methylenes) or through the incorporation of heavy atoms (e.g., deuterium for hydrogen, $^{13}C$ for carbon, $^{15}N$ for nitrogen).

In certain embodiments of the MPS-VII reagents defined above, the carbohydrate portion is replaced by a hydrogen atom; in this case a hydrogen atom is added to the aglycone. These reagents are representative of MPS-VII enzyme products and internal standards.

Representative MPS-VII reagents include the following compounds.

In certain embodiments, MPS-VII substrates have the formula:

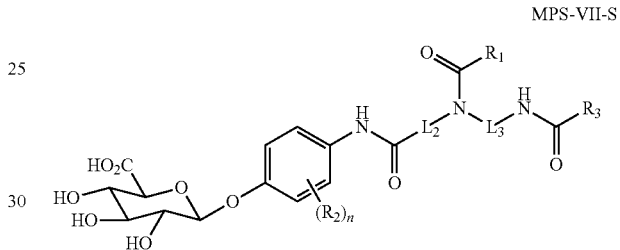

MPS-VII-S where $L_2$, $L_3$, $R_1$, $R_2$, $R_3$, and n are as described above for formula (III).

In certain embodiments, MPS-VII substrates have the formula:

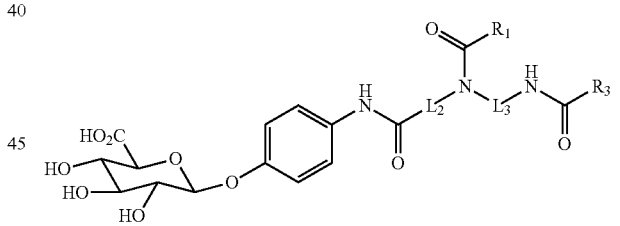

where $L_2$, $L_3$, $R_1$, and $R_3$ are as described above for formula (III).

A representative MPS-VII substrate has the formula:

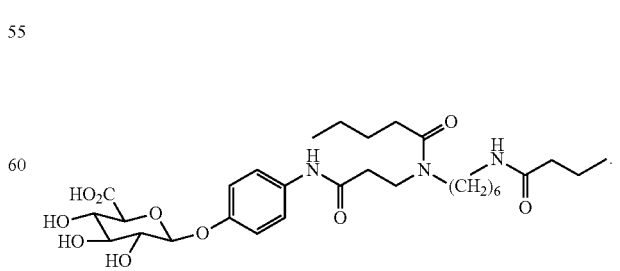

MPS-VII products formed from the above substrate (MPS-VII-S) have the formula:

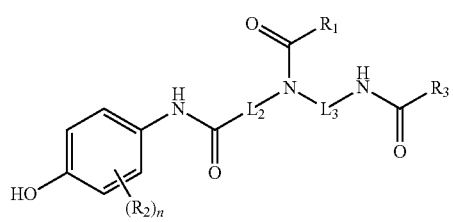

MPS-VII-P where $L_2$, $L_3$, $R_1$, $R_2$, $R_3$, and n are as described above for formula (III).

A representative MPS-VII product has the formula:

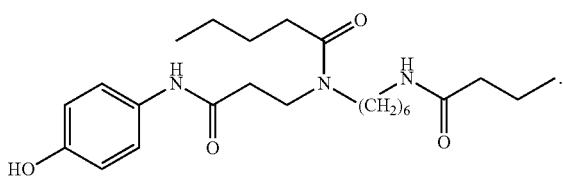

MPS-VII internal standards useful for assaying products formed from the above substrate (MPS-VII-S) have the formula:

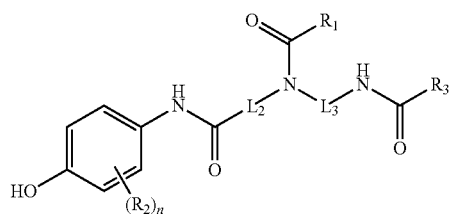

MPS-VII-IS where $L_2$, $L_3$, $R_1$, $R_2$, $R_3$, and n are as described above for formula (III), and where the mass of MPS-VII-IS differs from the mass of MPS-VII-P such that the two are distinguishable by mass spectrometry. As noted above, MPS-VII-IS can include one or more heavy atom isotopes (not shown in the structure above), or can have a structural variation (e.g., one or more of $L_2$, $L_3$, $R_1$, $R_2$, or $R_3$ for substrate differ from $L_2$, $L_3$, $R_1$, $R_2$, or $R_3$ for internal standard).

A representative MPS-VII internal standard has the formula:

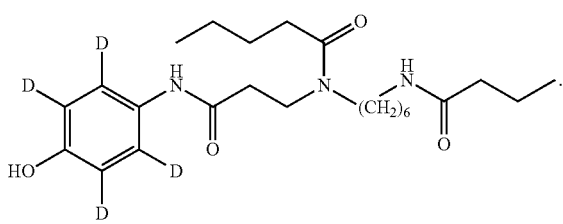

The representative MPS-VII product derived from the representative MPS-VII substrate can be assayed using the representative MPS-VII internal standard.

Salts.

In certain embodiments, the reagents include amino groups (e.g., —$NH_2$), carboxylic acid groups (—$CO_2H$), sulfonic acid groups (e.g., —$OSO_3H$), and amidosulfonic acid groups (e.g., —$NHSO_3H$), which depending on the pH environment can become charged groups (e.g., —$NH_3^+$, —$CO_2^-$, —$OSO_3^-$, —$NHSO_3^-$). It will be appreciated that the reagents of the disclosure include their salts (e.g., metal salts).

Reagent Kits

The reagents of the disclosure can be advantageously combined into kits to perform enzyme assays. Reagent kits for a particular assay include the appropriate enzyme substrate and internal standard pair (e.g., TTP1 substrate and TTP1 internal standard, PPT1 substrate and PPT1 internal standard, MPS-II-S and MPS-II-IS, etc). In certain embodiments, the kits include more than one substrate/internal standard pair and can be used to assay more than one enzyme (i.e., multiplex assay in which two, three, four, five, six, seven, eight, or nine enzymes can be assayed in a single screen). In other embodiments, the kits further include buffers for performing the assays. In other embodiments, the kits further include the enzymatic products, which can be used for tuning the mass spectrometer. In other embodiments, the kits further include quality control dried blood spots. Instructions for performing the assays can also be included in the kits.

Assay Methods

Representative methods for assaying the enzymes noted above are described in WO 2009/026252 (PCT/US2008/073516), WO 2010/081163 (PCT/US2010/020801), WO 2012/027612 (PCT/US2011/049224), and WO 2013/070953 (PCT/US2012/064205), each expressly incorporated herein by reference in its entirety. The reagents of the disclosure can be advantageously utilized in these methods.

The assays of the disclosure can include variations without departing from the disclosure. Several variations are described below.

In a first embodiment, substrate and internal standard are incubated in assay buffer with enzyme source, followed by quench (e.g., addition of acetonitrile) and then mass spectrometric analysis (e.g., LC/MSMS) and quantification of the enzyme product and internal standard.

In a second embodiment, the assay is as described in the first embodiment with the exception that the enzymatic reaction mixture is extracted (optionally without quench) with an organic solvent (e.g., ethyl acetate) suitable for extracting the product and internal standard, the extracted mixture concentrated to dryness and then taken up in a solvent suitable for flow injection mass spectrometric analysis (e.g., FIA/MSMS).

In a third embodiment, the assay is as described in the second embodiment with the exception that a suspension of anion exchange resin is added during the quench to trap the substrate.

In a fourth embodiment, when the assay includes a MPS screen, the assay is as described in the first embodiment with the exception that a second enzyme (e.g., a glycohydrolase, such as bacterial beta-N-acetylgalactoaminidase) suitable for cleaving the initial sulfatase product (sugar-aglycone with the sulfate removed) but not cleaving the substrate is added in the assay cocktail (substrate and internal standard). Following extraction, concentration, and resolubilization, mass spectrometric analysis (e.g., FIA/MSMS) is carried out leading to the quantification of the aglycone product and internal standard. In some cases there may be an enzyme that is endogenous in the dried blood spot sample that can act on the sulfated-sugar-aglycone substrate to cleave the glycosidic linkage (i.e. human hexosaminidase A). In this case an inhibitor of this endogenous enzyme may be added to block the action of the endogenous enzyme on the added substrate. This inhibitor is chosen so as to not block the action of the glycohydrolase added to the assay.

In a fifth embodiment, when the assay includes a MPS screen, the assay is as described in the second embodiment with the exception that a second enzyme (e.g., a glycohydrolase) suitable for cleaving selective sulfatase sugar-aglycone substrates is added in the assay cocktail (substrate and internal standard). Following quench, mass spectrometric analysis (e.g., LC/MSMS) is used to quantify the aglycone product and internal standard. In a modification of this embodiment, an inhibitor of an endogenous activity (e.g., human hexosaminidase A) is also added to the assay cocktail.

In a sixth embodiment, when the assay includes a MPS screen, substrate and internal standard are incubated in assay buffer with enzyme source, then a buffer is added to shift the pH (e.g., to pH 6) to optimize the activity of a second enzyme (e.g., a glycohydrolase), followed by addition of the glycohydrolase (e.g., bacterial beta-N-acetylgalactoaminidase) and incubation (e.g., 1-2 hrs). The sample is then quenched, and mass spectrometric analysis (e.g., LC/MSMS) is used to quantify the aglycone product and internal standard. In a modification of this embodiment, an inhibitor of an endogenous enzyme activity (e.g., human hexosaminidase A) is also added to the assay cocktail.

In a seventh embodiment, the assay is as described in the sixth embodiment with the exception that the enzymatic reaction mixture is extracted (optionally without quench) with an organic solvent (e.g., ethyl acetate) suitable for extracting the product and internal standard, the extracted mixture concentrated to dryness and then taken up in a solvent suitable for flow injection analysis (e.g., FIA/MSMS). In a modification of this embodiment, an inhibitor of an endogenous enzyme activity (e.g., human hexosaminidase A) is also added to the assay cocktail.

In an eighth embodiment, for the embodiments above that include a MPS screen, and that utilize extraction with an organic solvent to isolate product and internal standard, after removal of the solvent a solution of a suitable acylating agent (e.g. acetic anhydride) and suitable base (e.g., triethylamine) in a suitable solvent is added and the resulting combination incubated (1-2 hr) to provide acylated (e.g., acetylated) aglycone products and internal standards having increased sensitivity in MS analysis.

In a ninth embodiment, the assay is as described in the eighth embodiment with the exception that the acylating agent and base are included in the extraction (e.g., ethyl acetate) solvent to cause the aglycone and internal standard to become acylated (e.g., acetylated) during the extraction process or after the extract is allowed to incubate (e.g., for 1-2 hrs).

In a tenth embodiment, when the assay includes a MPS screen, substrate and second enzyme (glycohydrolase) are incubated in assay buffer with enzyme source, followed by quench, and then fluorescence analysis to quantitate fluorescent product. In a modification of this embodiment, an inhibitor of an endogenous enzyme activity (e.g., human hexosaminidase A) is also added to the assay cocktail. For this embodiment, substrates with Type A aglycone are used.

In an eleventh embodiment, when the assay includes a MPS screen, substrate is incubated in assay buffer with enzyme source, then a buffer is added to shift the pH (e.g., to pH 6) to optimize activity of a second enzyme (e.g., a glycohydrolase), followed by addition of the glycohydrolase (e.g., bacterial beta-N-acetylgalactoaminidase) and incubation (e.g., 1-2 hrs), then quench and fluorescence analysis quantification of the fluorescent product. In a modification of this embodiment, an inhibitor of an endogenous enzyme activity (e.g., human hexosaminidase A) is also added to the assay cocktail. For this embodiment, substrates with Type A aglycone are used.

In certain embodiments, additional assay options are also included within the methods of the disclosure, in particular for multiplex assays that include screens for MPS. Two options are described below.

Assay Option 1.

After the incubation of the desired set of substrates with enzyme source in a suitable buffer, the reaction is subjected to liquid-liquid extraction with a suitable solvent such as ethyl acetate. If MPS-II is assayed without use of the second enzyme (glycohydrolase) to generate the aglycone, the mixture should be acidified to pH about 2-3 with a suitable acid such as citric acid so that the carboxylate group of the MPS-II-P will be protonated and better extract into ethyl acetate. If the second enzyme is used in this assay to remove the sugar, the aglycone will extract well into the solvent without acidification because it does not have a carboxy group. The purpose of the liquid-liquid extraction step is 2-fold: (1) extraction leads to removal of most of the buffer salts, which would interfere with the ionization process in the mass spectrometer; and (2) extraction leads to extraction of most of the enzyme products with minimal extraction of the enzyme substrates. This is useful because the substrates can partially decompose by loss of sulfate in the ionization source of the mass spectrometer to form product, and it is only the product generated enzymatically that one desires to quantify. After liquid-liquid extraction, the ethyl acetate layer is transferred to a new container and solvent is removed by evaporation. The residue is taken up in a solvent suitable for injection into the mass spectrometer. An example solvent is aqueous ammonium formate/methanol mixtures. The products and internal standards are detected in multiple reaction monitoring mode in which the precursor ion is isolated in the first quadrupole and is then subjected to collision-induced dissociation to form one or more product ions. One such product ion is isolated in the third quadrupole and is detected by the ion detector (tandem mass spectrometry). Each fragmentation reaction, one for each product and internal standard, is monitored separately in a duty cycle fashion such that the full set of products and internal standards are quantified. To obtain the moles of product, the mass spectrometry signal (ion counts) for the product is divided by that for the internal standard, and this ratio is multiplied by the moles of internal standard added to the assay.

Assay Option 2.

A variation of the above assay makes use of a modified pre-mass spectrometry sample workup. After the incubation to allow products to be generated enzymatically from substrates, a small aliquot of a suitable anion exchange resin is added to the mixture. An example resin is DE52 from Whatmann. It is well known that anions bind by electrostatic interaction with cations on the anion exchange resin, in this case all anionic analytes will bind to the resin. The substrates MPS-I-S, MPS-II-S, MPS-IIIA-S, MPS-IVA-S, MPS-VI-S, and MPS-VII-S contain either a carboxylate (MPS-I-S and MPS-VII-S) or a sulfate ester and will thus bind to the resin. The MPS-I-P, MPS-I-IS, MPS-IVA-P, MPS-IVA-IS, MPS-VI-P, MPS-VI-IS, MPS-VII-P, and MPS-VII-IS lack charge or contain a positive charge (MPS-IIIA-P and MPS-IIIA-IS) and will thus not be bound to the resin. The MPS-IIIB-S, MPS-IIIB-P and MPS-IIIB-IS also lack negative charge and will not bind to the resin. The MPS-II-S, MPS-II-P and MPS-II-IS are all anionic and thus will all bind to the resin. In this assay option, the assay buffer contains recombinant alpha-L-iduronidase, which acts on MPS-II-P and MPS-II-IS, not on MPS-II-S, to remove the iduronic acid residue from the aglcyone thus leaving behind the free aglycone, which lacks charge. Thus the resulting analytes derived from MPS-II-P and MPS-II-IS will not bind to the anion exchange resin. If recombinant alpha-L-iduronidase is included, the assay cannot include MPS-I-S because the enzyme will act on MPS-I-S to make MPS-I-P. The use of alpha-L-iduronidase is not limited to those MPS-II assays where anion exchange resin is added. The addition of this enzyme can also be done for all other MPS-II assays where anion exchanger is not used.

After addition of anion exchange resin, the mixture is extracted with ethyl acetate as in Assay Option 1, and all analytes not bound to the resin will extract into ethyl acetate. The ethyl acetate layer is then processed as described in Assay Option 1 for analysis by tandem mass spectrometry.

Sulfatase Assays: MPS II, IIIA, IVA, and VI Screening

In some embodiments, lysosomal assays can also be used to detect of sulfatases (MPS II, IIIA, IVA, and VI) associated with lysosomal storage diseases for newborn screening. The assays utilize substrates of the general structure: sulfate-sugar-aglycone. These substrates are acted on by the lysosomal sulfatase to yield the product lacking sulfate: sugar-aglycone. In certain assays, the sugar-aglycone product was detected using tandem mass spectrometry.

The present disclosure provides an alternative to those sulfatase assays. In certain aspects of the MPS assays of the present disclosure, a second enzyme is added to the assay cocktail so as to effect remove of the sugar to provide the aglycone. Tandem mass spectrometry detection of the aglycone is more sensitive than detection of the sugar-aglycone. The second enzyme that removes the sugar does not act on the sulfated sugar (i.e., the second enzyme does not act on the substrate for the sulfatase). Thus, the present disclosure provides a method that includes an additional step of adding a suitable glycohydrolase or suitable lysase to the assay cocktail to produce the aglycone as the final enzyme product, which is then detected by tandem mass spectrometry.

As used herein, the term "glycohydrolase" refers to an enzyme that hydrolyzes glycosides. The term "lysase" refers to an enzyme that removes a proton from the sugar C2 and eliminates the glycosidic oxygen (e.g., aglycone leaving group) to provide an unsaturated sugar derivative.

Suitable second enzymes (e.g., glycohydrolases and lysases) are characterized in that they do cleave the sugar from the aglycone for the enzyme products described herein (e.g., they only cleave the sugar once the sulfate is removed), they do not act on the enzyme substrates themselves, and they are not inhibited by an inhibitor that is added in the MPS assays of the disclosure to block the action of endogenous enzymes present in the dried blood spot like hexosaminidase A, which can cleave the sulfated substrate to provide the aglycone.

Suitable second enzymes include glycohydrolases and lysases.

Representative glycohydrolases include human hexosaminidase A, bacterial N-acetylhexosaminidases, bacterial β-N-acetylgalactosaminidase (e.g., *Paenibacillus* sp. TS12), alpha-L-iduronidase, β-galactosidase (*aspergillus*), and α-glucosidase (yeast).

Representative lysases include heparin lysase (heparinase) and heparanase.

Assay Methods.

In one aspect, the disclosure provides methods for screening for MPS II, IIIA, IVA, and VI, in addition to TPP1 and PPT1. The methods assay specific enzymes, the deficiencies of which lead to the lysosomal storage disease conditions. The methods advantageously assay one or more of TPP1, PPT1, iduronate-2-sulfatase (MPS-II), heparan N-sulfatase (MPS-IIIA), N-acetylgalactosamine-6-sulfate-sulfatase (MPS-IVA), and N-acetylgalactosamine-4-sulfate-sulfatase (MPS-VI).

As noted above, in the MPS methods, a second enzyme is utilized to improve the sensitivity of the mass spectrometric assay embodiments and to generate the fluorophore in the fluorescent assay embodiments. In accordance with the methods, a suitable sulfatase substrate (i.e., sulfate-sugar-aglycone) is contacted with a sample to be assessed for sulfatase activity. When the sample includes a sulfatase, the substrate is enzymatically converted to an initial enzyme product (i.e., sugar-aglycone). In the MPS methods, a second enzyme (e.g., a glycohydrolase) acts on the initial enzyme product to provide a secondary enzyme product (i.e., aglycone). Analysis of the secondary enzyme product (i.e., the aglycone) by tandem mass spectrometry provides increased sensitivity compared to previous assays in which the second enzyme is not present and which rely on the analysis of the initially formed enzyme product, the sugar-aglycone. For substrates containing a type A aglycone, the second enzyme acts to release the fluorescent aglycone only after the sulfate is removed. This allows the sulfatase to be assayed by fluorescence analysis.

For fluorescent assays the quench can include a buffer to raise the pH to about 10 so that the phenolic hydroxy of the aglycone is deprotonated thus rendering the product (aglycone) highly fluorescent.

In the MPS assays, one or more substrates (S) are incubated in a suitable buffer with a suitable source of enzymes such as a dried blood spot from a newborn screening card or a urine sample for a sufficient time to form one or more products (P1) that are subsequently subjected to a second enzyme (i.e., a glycohydrolase) to provide secondary enzyme products (P2) that are detected by tandem mass spectrometry. The assay also makes used of an internal standard (IS), which in certain embodiments are chemically identical to the enzyme-formed product, but has a different mass (e.g., heavy isotope substituted such as deuterium and/or carbon-13 substitutions). In certain assays, the internal standard is also acted on by the second enzyme to form the final internal standard that is detected by tandem mass spectrometry. The incubation is done in a suitable buffer to allow the enzymatic reactions to proceed. A suitable buffer is for example 100 mM ammonium formate pH 4.5 containing 7.5 mM barium acetate and 5 mM cerium acetate.

MPS enzymes that are advantageously assayed with the reagents of the disclosure include the following:

(a) iduronate-2-sulfatase, which acts on the substrate of MPS-II to produce the MPS-II product, and the assay makes use of the MPS-II internal standard;

(b) heparan N-sulfatase, which acts on the substrate of MPS-IIIA to produce the MPS-IIIA product, and the assay makes use of the MPS-IIIA internal standard;

(c) N-acetylgalactosamine-6-sulfate-sulfatase, which acts on the substrate of MPS-IVA to produce the MPS-IVA product, and the assay makes use of the MPS-IVA internal standard; and (d) N-acetylgalactosamine-4-sulfate-sulfatase, which acts on the substrate of MPS-VI to produce the MPS-VI product, and the assay makes use of the MPS-VI internal standard.

In certain embodiments, additional assay options are also included within the methods of Assay options 1 and 2 noted above can be utilized in these assay methods.

Reagents.

Reagents for screening MPS II, IIIA, IVA, and VI include substrates (S), products (P), and internals standards (IS) for screening for MPS II, IIIA, IVA, and VI.

The reagents can be advantageously utilized to assay enzymes. The reagents include enzyme substrates (S), enzyme products (P), and assay internal standards (IS). In certain embodiments, one or more substrates (S) and their corresponding internal standards (IS) are incubated in a suitable buffer with a suitable source of enzymes such as a dried blood spot from a newborn screening card or a urine sample for a sufficient time to form one or more products (P) that are subsequently subject to a second enzyme (e.g., a glycohydrolase) to provide a second enzyme product that is detected by tandem mass spectrometry. In certain embodiments, the internal standard (IS) is chemically identical to the enzyme-formed product except the standard has a different mass (e.g., heavy isotope substituted such as deuterium and/or carbon-13 substitutions).

Reagents useful in the assay of these sulfatases include substrates (S), products (P), and internals standards (IS) for MPS-II, MPS-IIIA, MPS IVA, and MPS-VI, including those described herein.

Representative Assays for MPS IVA and VI Screening

As described above, glycohydrolase and lysase enzymes are used to improve the sensitivity of assaying sulfatases using mass spectrometry and to provide fluorescent aglycone products for fluorescent assays. In a related aspect, a method is provided that further includes the step of adding an inhibitor to block endogenous glycohydrolase activity.

Suitable inhibitors block endogenous glycohydrolase activity, but do not significantly inhibit the activity of the added glycohydrolase. Dried blood spots contain, for example, hexosaminidase A, which can act on the sulfated substrate to form the aglycone in one step. In this case it is optimal to add an inhibitor of the hexosaminidase when the aglycone is measured by tandem mass spectrometry or fluorimetry in order to quantify the sulfatase enzyme. The added inhibitor should not significantly inhibit the second enzyme, which is added to the assay to convert the initial sulfatase product to the aglycone.

Suitable inhibitors block the hexosaminidase(s) in the biological sample, but do not fully block the second enzyme. The inhibitor may partially block the latter, but not so completely that the latter can convert most if not all of the initial sulfatase product to its aglycone. Suitable inhibitors inhibit human hexosaminidinase A, human hexosaminidinase B, and/or human hexosaminidase X.

Representative inhibitors include (Z)—O-(2-acetamido-2-deoxy-D-glucopyranosylidene)-amino N-phenylcarbamate (Z-PUG-NAc), 1-deoxynojirmycin, castanospermine, swainsonine, calystegine $B_2$, isofagamine, Tamiflu, gluconohydroximolactone, glucuronic acid and its lactones and lactams, Relenza, miglitol, phenethyl substituted gluco- and galacto-imidazoles, N-hydroxyethyl dehydronojirimycin, GalNAc thiazoline, and GlcNAc thiazoline.

The following examples are included for the purpose of illustrating, not limiting, the described embodiments.

Example 1 describes the synthesis of examples of TPP1 and PPT1 substrates and internal standards, as well as the simplex and duplex assays using these substrates and internal standards. The PPT1 assays in Example 1 detect the cleaved peptide portion when the substrate is subjected to the PPT1 enzyme. Example 2 describes a PPT1 assay that detects the fatty acyl portion when an example PPT1 substrate is subjected to the PPT1 enzyme. Example 3 describes a multiplex assay of TPP1 and MPS.

EXAMPLES

Example 1

Simplex and Duplex TPP1 and PPT1 Assays

Materials

All water used was purified by a Millipore Milli-Q 18 MΩ System. N-acetylated heptapeptides ALLPFGC and AAAP-FGC, and Fmoc-protected AAF were purchased from Lifetein (Hillsborough, N.J.). Palmitoyl chloride (98% pure), Fmoc-4-aminomethylbenzoic acid, N-(3-dimethylaminopropyl)-N'-ethylcarbodiimide hydrochloride, and tris-(2-carboxyethyl) phosphine hydrochloride were purchased from Sigma-Aldrich (St Louis, Mo.). All solvents used were technical grade as supplied by Sigma-Aldrich. Triton X-100 purchased from ACROS (NJ, USA). Solid phase extraction C18 Omix pipette tips were supplied by Agilent (Santa Clara, Calif.). All experiments and sample handling were conducted in compliance with Institutional Review Board guidelines. All infantile CLN1 and CLN2 affected patients had been diagnosed previously with established clinical and biochemical procedures. DBS were stored at −20° C. in zip-lock plastic bags (one bag sealed inside a second bag). Zip-lock bags were kept in a sealed plastic box containing desiccant (anhydrous $CaSO_4$ granules). Details of the substrate synthesis are given below.

Mass Spectrometry

Figure 1B:
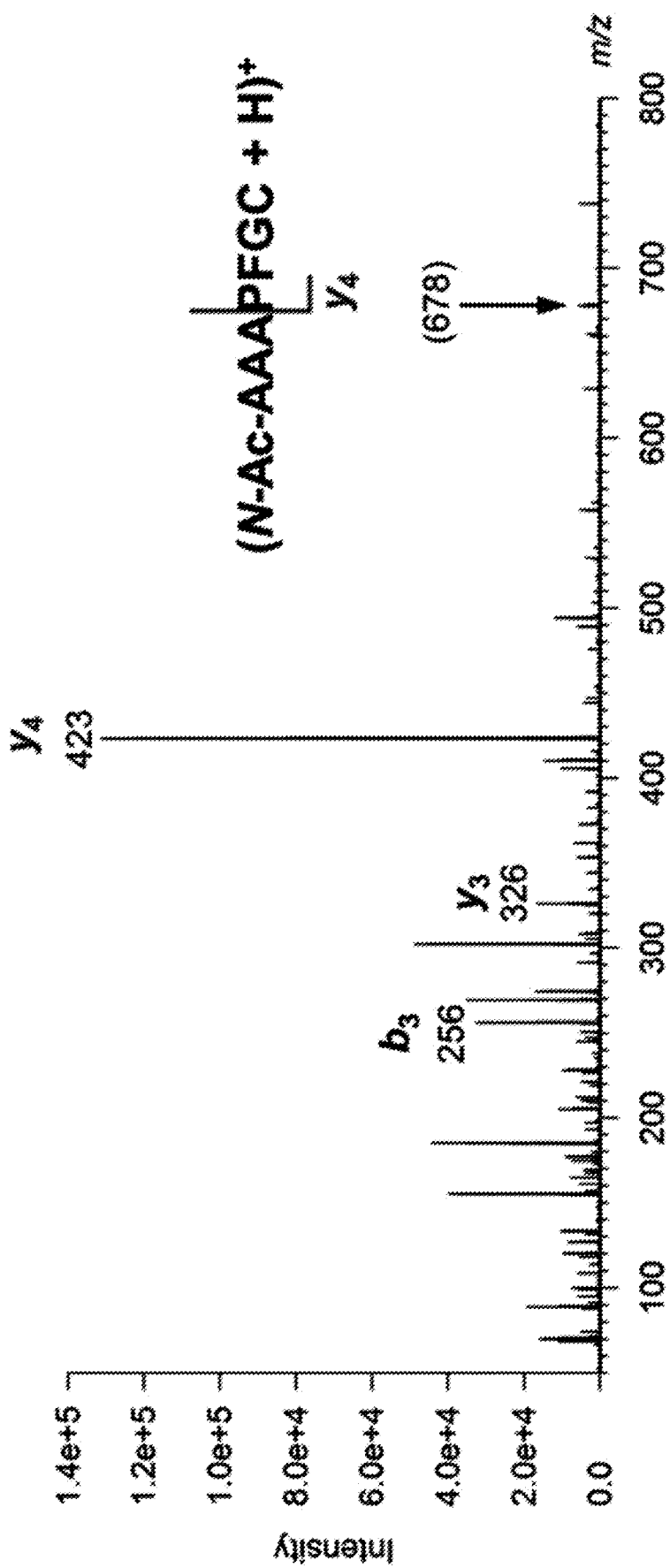
FIG. 1B is a tandem mass spectrum of (N-Ac-AAAP-FGC+H)$^+$ ion at m/z 678, both obtained at 25 eV laboratory ion collision energy.
Figure 2:
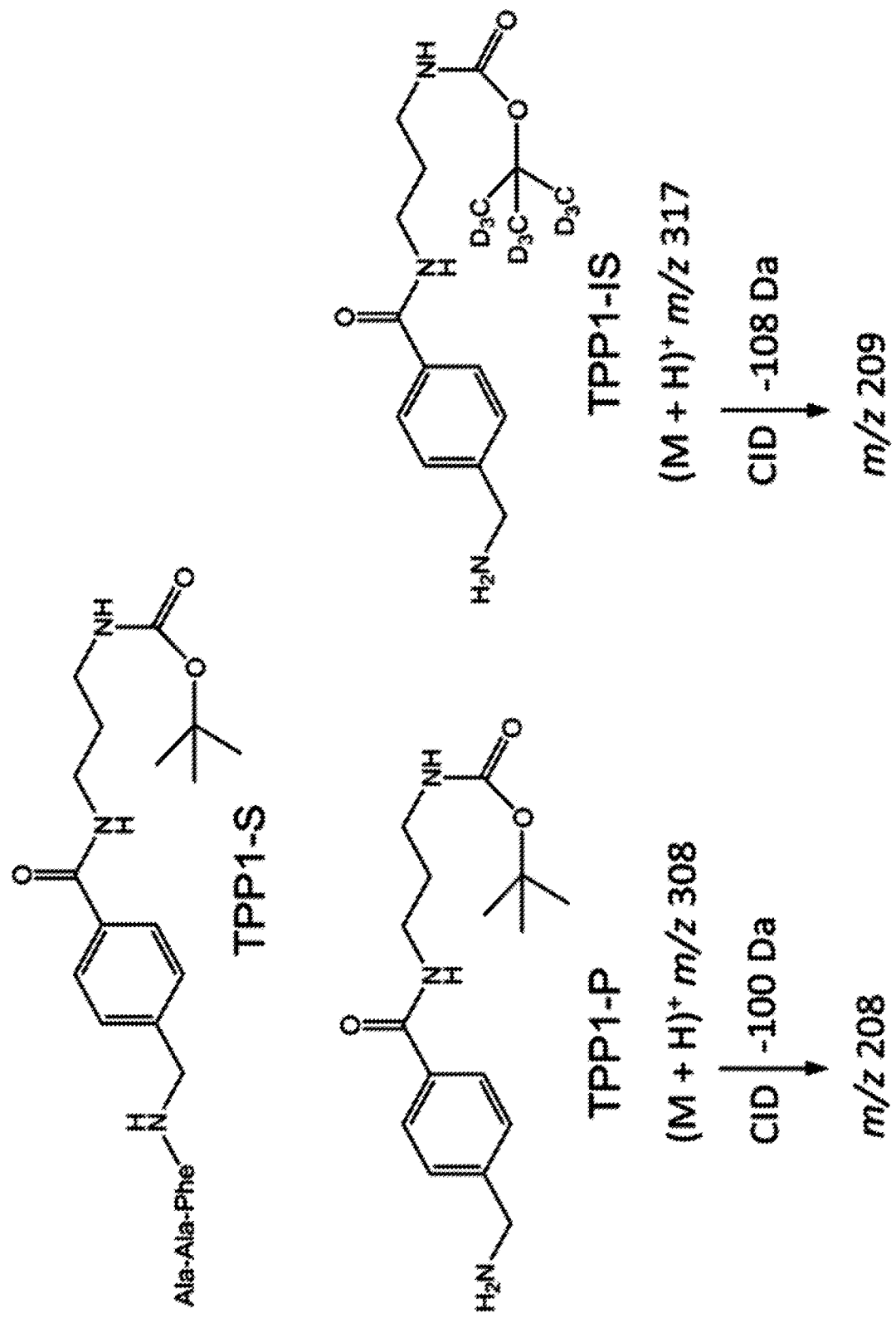
FIG. 2 is an illustration of structures of an embodiment of a TPP1 substrate (TPP1-S), an embodiment of a TPP1 enzyme product (TPP1-P), an embodiment of an internal standard (TPP1-IS), and the pertinent selected reaction monitoring (SRM) transitions.

Electrospray-MS/MS was carried out on a Waters Quattro Micro tandem quadrupole (quadrupole-hexapole-quadrupole) instrument using a positive ionization mode and selected reaction monitoring (SRM). Samples (10 μL) were flow-injected with an autosampler in an acetonitrile/water (v/v=80:20) solution containing 0.1% formic at a flow rate of 0.2 mL/min. The mass spectrometer settings were as follows: Capillary voltage 3.5 kV; cone 35 V; extractor 2.0 V; RF lens, 0.2 V; source temperature, 120° C.; desolvation temperature, 250° C.; cone gas flow, 50 L/h; desolvation gas flow, 500 L/h; LM 1 resolution, 14.8; HM 1 resolution, 14.8; ion energy 1, 0.2 eV; entrance, 2 V; collision, 25 eV; exit, 15 V; LM 2 resolution, 14.8; HM 2 resolution, 14.8; ion energy 2, 1.0 eV; multiplier, 650 V; gas cell Pirani pressure, $2.21×10^{-3}$ mbar; dwell time 100 ms. Shorter dwell times (10 ms) were also investigated on the Quattro Micro instrument but led to increased coefficients of variation (CV) for intra-assay measurements from 1.5% at 100 ms to 4% at 10 ms, all for triplicate injections. The precursor ion-fragment ion SRM transitions for the PPT1 assays were monitored at m/z 762.5→m/z 423.5 and m/z 678.4→m/z 423.4 for PPT1-P and PPT1-IS, respectively, corresponding to the formation of the abundant $y_4$ fragment ion of the peptide (FIGS. 1A and 1B). The SRM transitions for the TPP1 assays were monitored at m/z 308.3→m/z 208.3 and m/z 317.3→m/z 209.3 for TPP1-P and TPP1-IS, respectively, as shown in FIG. 2.

Assay Protocols

PPT1 Assay.

A 3-mm punch of a dried blood spot was placed in a 1.5 mL polypropylene tube (Eppendorf) and 100 μL of 100 mM phosphate buffer solution (pH 7) containing 46 nmol of PPT1 substrate (PPT1-S, FIG. 5 (left)) and 2.6 nmol of PPT1 internal standard (PPT1-IS) and 0.08% v/v Triton X-100 (ACROS, Cat #21568) was added. The solution was then vortexed briefly and incubated for 10 h at 37° C. in a thermostated air shaker at 250 rpm. After the incubation period was over, the sample was placed in an ice bath and the reaction was quenched by addition of 300 μL of ethyl acetate and 100 μL of deionized water. The tubes were vortexed and centrifuged, and the ethyl acetate layer containing Triton X-100 was separated and discarded. The assay product (PPT1-P) and internal standard (PPT1-IS) were isolated and desalted by solid phase extraction on C18 pipette tips (Omix Tips, Agilent Cat # A57003100) followed by elution with 200 μL of a 50:50 acetonitrile:water 1% acetic acid. Prior to injection into the mass spectrometer, the samples were treated with 800 μM tris(2-carboxyethyl) phosphine hydrochloride, TCEP (Sigma-Aldrich, cat # C4706) and incubated for 30 minutes a 37° C. to reduce disulfide bonds formed by cysteine oxidation during the assay.

TPP1 Assay.

TPP1 substrate solution was prepared by dissolving 5 mg TPP1 substrate (FIG. 5 (right)) in 1.5 mL of dimethyl sulfoxide (DMSO). 1 mg TPP1 IS was dissolved in 1.5 mL of assay buffer, which contained 0.15 M NaCl and 0.1 M sodium acetate buffer at pH 4.0. This concentrated TPP1 IS solution was further diluted with stock assay buffer to make a 300 μM IS solution. The assay cocktail was a 100 μL mixture composed of 7.2 μL of substrate solution (40 nmol), 5 μL of 300 μM IS solution (1.5 nmol) and additional 87.8 μL of stock assay buffer. A 3-mm punch of a dried blood spot (DBS) was placed in a 1.5 mL polypropylene Eppendorf tube containing 100 μL of assay cocktail. The solution was then vortexed briefly and incubated for 10 h at 37° C. in a thermostated air shaker at 250 rpm. After incubation, 10 μL of 15% aqueous trifluoroacetic acid was added to quench the assay, followed by 200 μL of 1 M NaOH, and then 800 μL ethyl acetate. The mixture was vortexed, centrifuged, and 750 μL of the top ethyl acetate layer were collected to dry down. Then the dried residue was reconstituted in 200 μL of acetonitrile/water (v/v=50:50) with 1% acetic acid for analysis by MS.

Design and Synthesis of Substrates and Internal Standards

The PPT1 substrate is a cysteine terminated heptapeptide carrying an S-palmitoyl group, N-Ac-Ala-Leu-Leu-Pro-Phe-Gly-Cys-S—$COC_{11}H_{23}$. Acetylation of the N-terminus protects the substrate and the PPT1 product from being attacked by serum exopeptidases that are present and may be active in rehydrated DBS. The internal standard, N-Ac-Ala-Ala-Ala-Pro-Phe-Gly-Cys, is homologous with the depalmitylated enzyme product, N-Ac-Ala-Leu-Leu-Pro-Phe-Gly-Cys. The amino acid residues in the substrate, product, and internal standard were designed with two features in mind. One was to produce peptides that would be sufficiently lipophilic to be readily extracted on the C18 solid-phase support. The other feature was to promote residue-selective ion fragmentation upon collisional activation that would focus most of the fragment ion signal into a single dominant dissociation channel. This was accomplished by incorporating in the peptides the proline residue that directs the backbone fragmentation to form a dominant $y_4$ ion at m/z 423, which is common for the enzyme product and the internal standard (FIGS. 1A and 1B). The PPT1 substrate was prepared by a single step palmitoylation of a readily available peptide precursor according to Scheme 1.

Figure 6A:
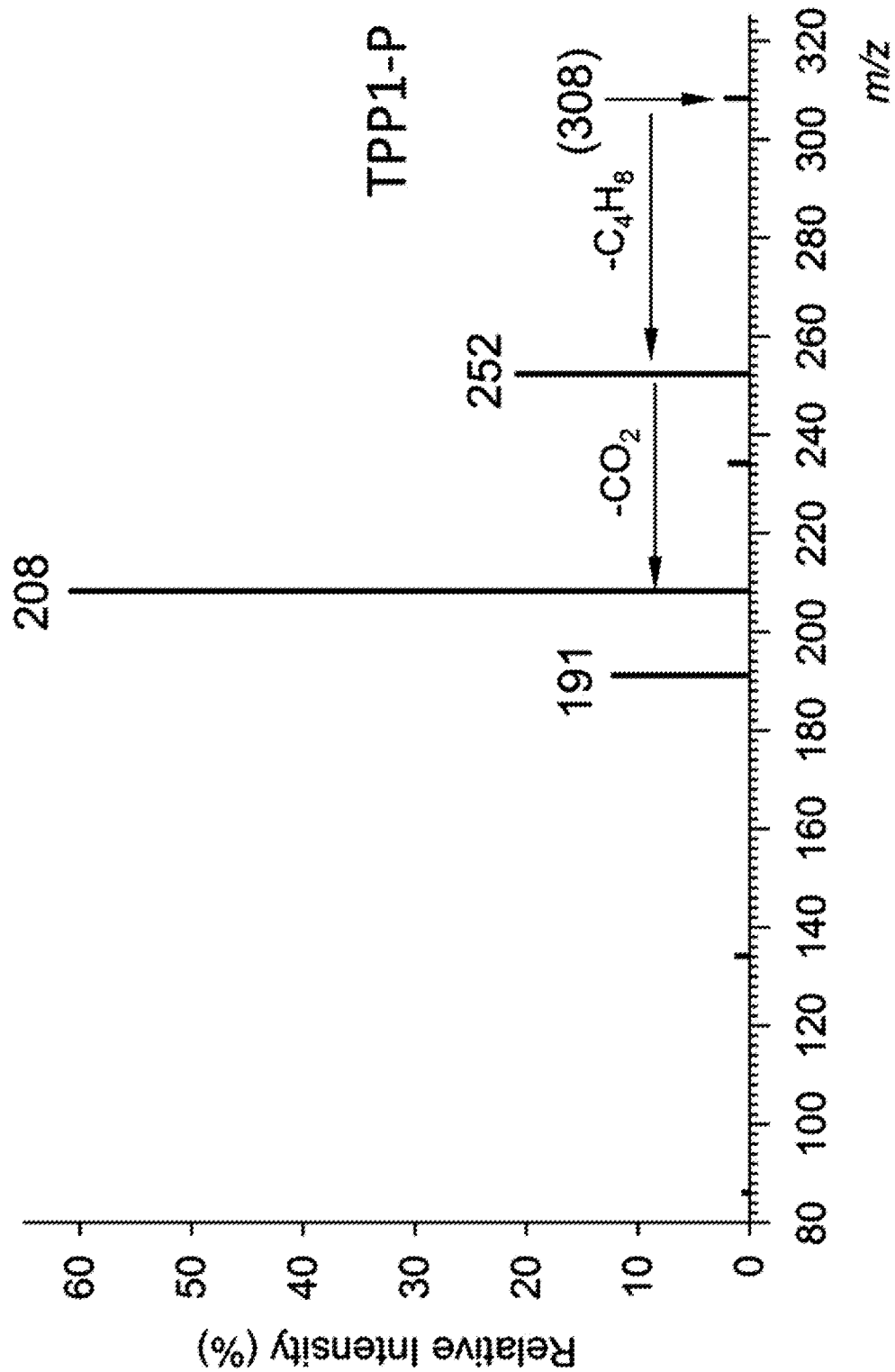
FIG. 6A is a CID-MS/MS spectrum of a (M+H)$^+$ ion m/z 308 from TPP1-P.
Figure 6B:
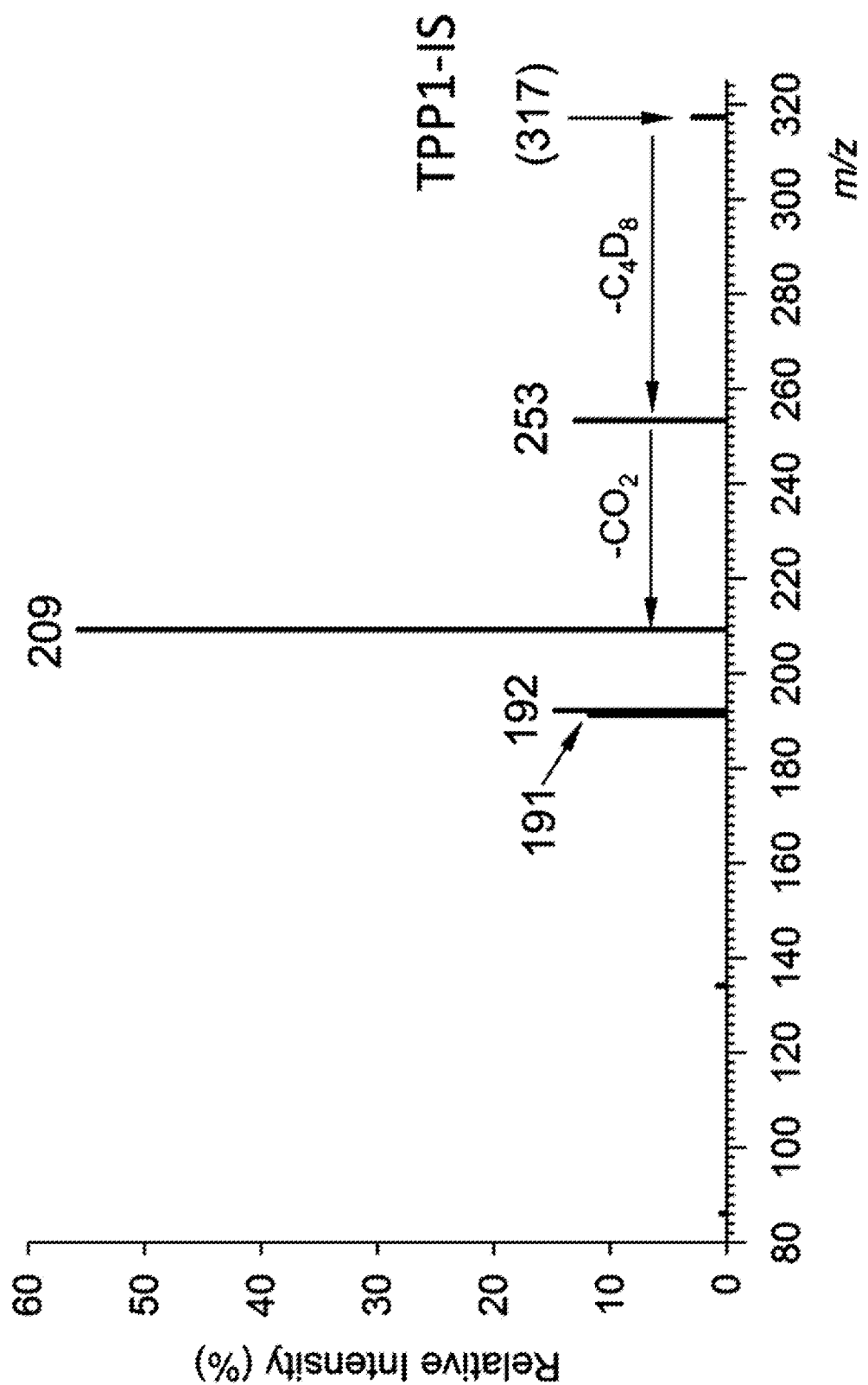
FIG. 6B is a CID-MS/MS spectrum of a (M+H)$^+$ ion m/z 308 from TPP1-IS.

The substrate for TPP1 (TPP1-S, FIG. 2) is a conjugate containing the Ala-Ala-Phe triad, which is preferentially cleaved by the enzyme, that is linked by an amide bond to a non-peptidic moiety. The latter consists of an 4-aminobenzylcarboxamide, a 1,3-propanediamine and a t-butyloxycarbamate group (t-BOC). The product (TPP1-P) and internal standard (TPP1-IS) retain the hydrophobic benzyl, propylene, and t-BOC linkers to be readily extracted in ethyl acetate or on C18 solid-phase support. The t-BOC group allows for an introduction of deuterium label in the IS. Upon collisional activation, ions containing the t-BOC group readily dissociate by consecutive loss of $C_4H_8$ and $CO_2$ which provides suitable channels for selected reaction monitoring. The ion transitions of the PPT1 product and IS, m/z 308→m/z 208 and m/z 317→m/z 209, respectively (FIGS. 6A and 6B), overlap with none of the other products and internal standards in the LSD assay cassette, thus allowing multiplex quantitation by SRM. The TPP1 substrate was synthesized from the components by standard coupling reactions in five steps (Scheme 2). The product and $d_9$-internal standard were prepared in four steps (Scheme 3).

Assay Evaluation and Optimization.

Both assays were evaluated and optimized regarding the incubation conditions affecting the enzyme activity, work-up procedures affecting the product and IS recovery, and mass spectrometric analysis affecting the ionization efficiency and collision induced dissociation. Results of the relevant measurements are summarized in FIGS. 7A to 15.

Figure 7B:
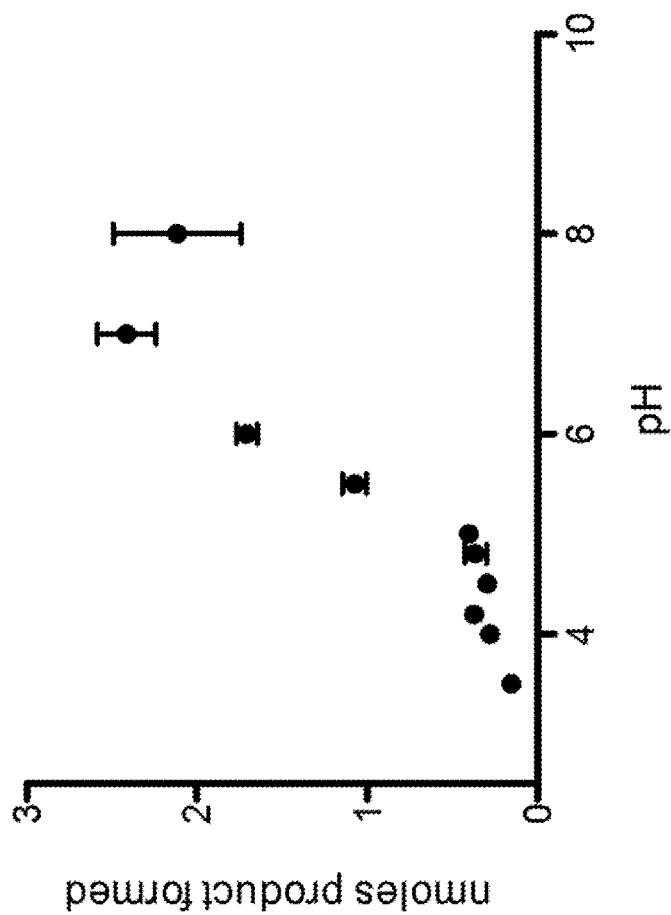
FIG. 7B is a graph showing the amount of PPT1 enzymatic product formed after correction for blank.
Figure 7A:
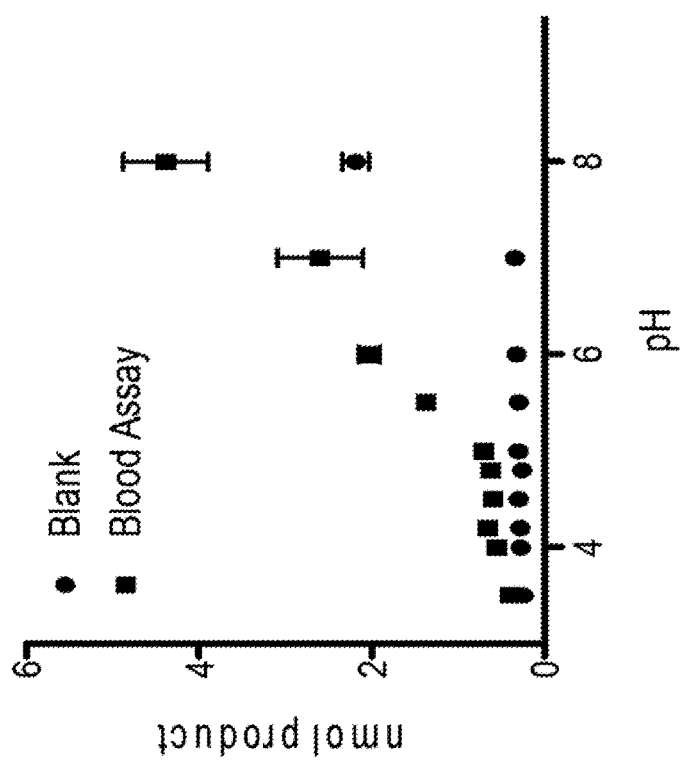
FIG. 7A is a graph showing the dependence on pH of PPT1 product formation, where the total product formed in the presence of DBS is shown as squares and product formed in the absence of DBS is shown as circles.
Figure 8:
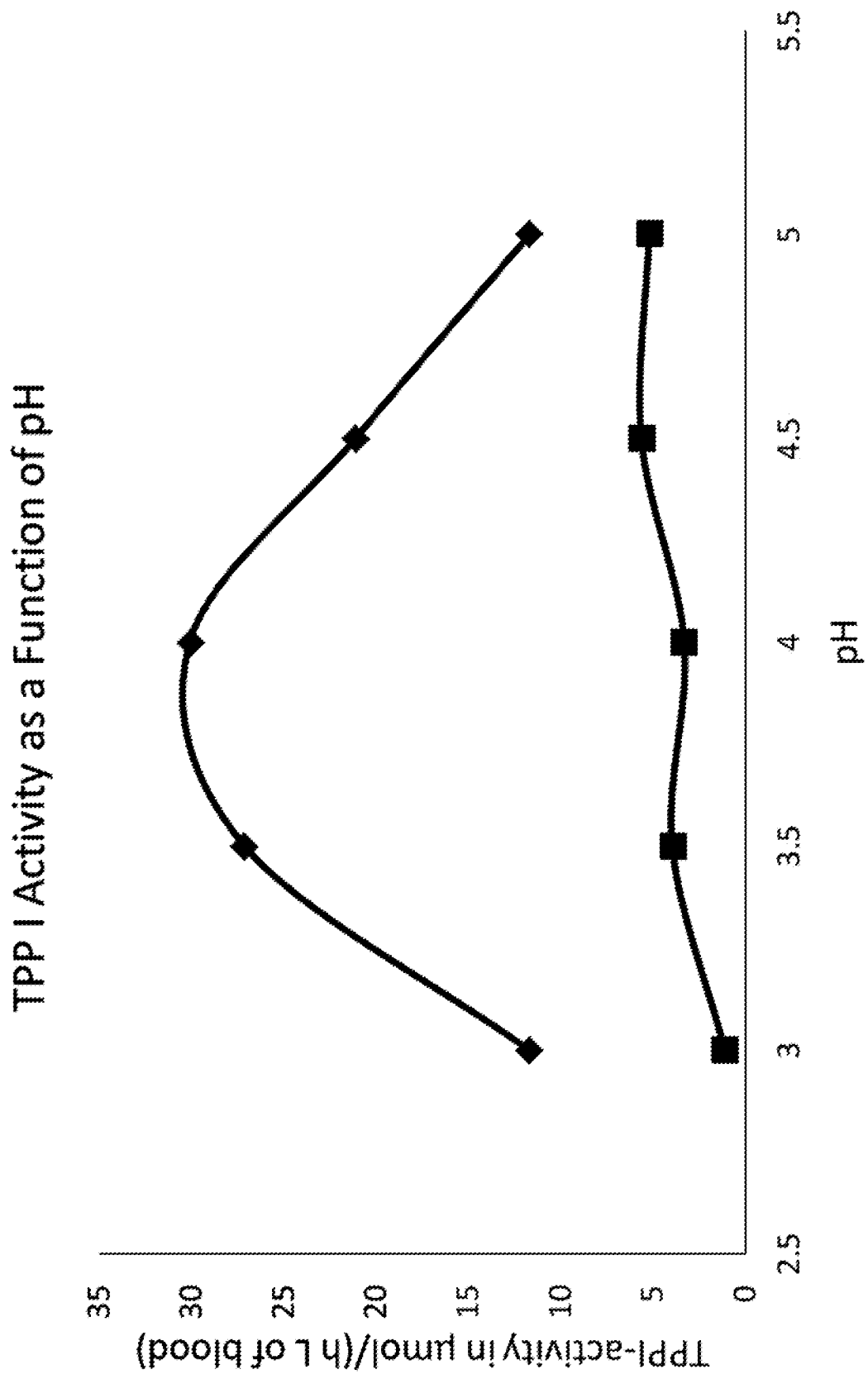
FIG. 8 is a graph showing the dependence of TPP1 activity on pH.

The PPT1 activity is known to have an optimum activity at pH 7 when acting on the natural substrate. The PPT1 activity in DBS with respect to the synthetic PPT1 substrate showed a similar pH dependence, increasing from pH 4 to pH 8 (FIG. 7A). However, non-enzymatic hydrolysis of the thioester bond in the PPT1 substrate substantially increased between pH 7 and 8. Therefore, the assay pH was adjusted to pH 7, which showed a maximum activity after a blank correction (FIG. 7B). The TPP1 activity towards TPP1-S showed a pH dependence profile which was more typical of a lysosomal enzyme, peaking at pH 4 (FIG. 8). The production of TPP-P by non-enzymatic hydrolysis in the blank sample at pH 4 was ca. 15 fold lower than that due to TPP1 activity in the DBS.

Figure 9:
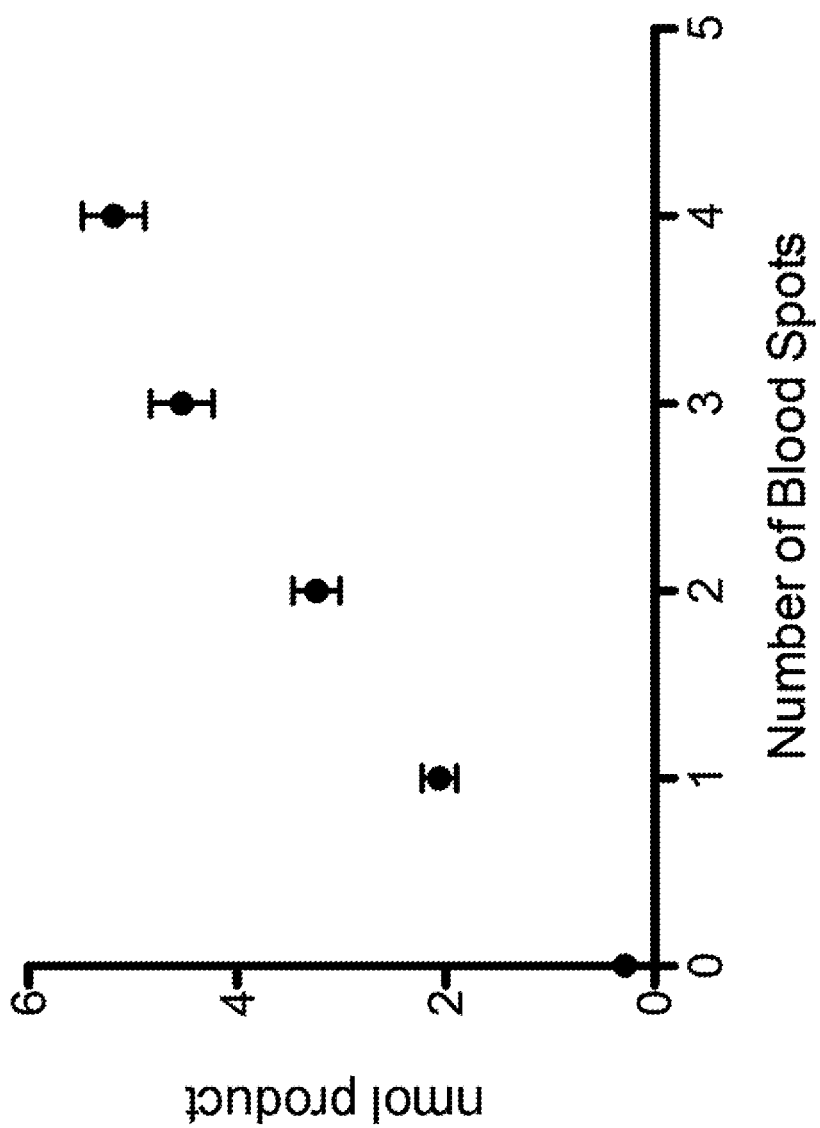
FIG. 9 is a graph showing PPT1 activity as a function of the number of DBS.

The PPT1 activity as a function of the amount of enzyme was established by conducting the assays with an increasing number of DBS punches from a single donor. FIG. 9 shows that the PPT1 activity increased approximately linearly with the number of DBS used for the assay. The amount of product obtained from a single DBS punch (2 nmol) was sufficient for activity enzyme measurements in the assays.

Figure 10:
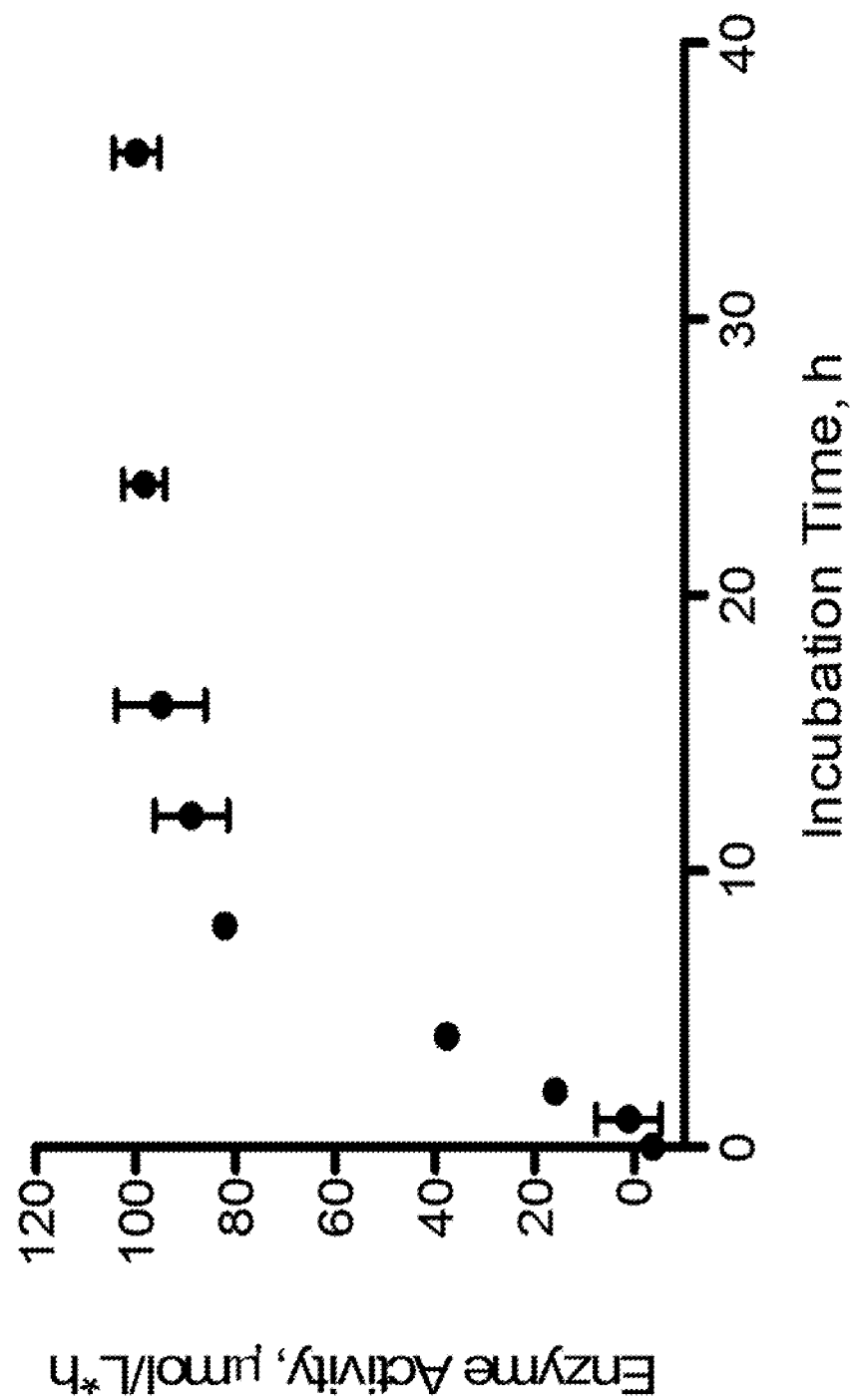
FIG. 10 is a graph of PPT1 product formation as a function of incubation time.
Figure 11:
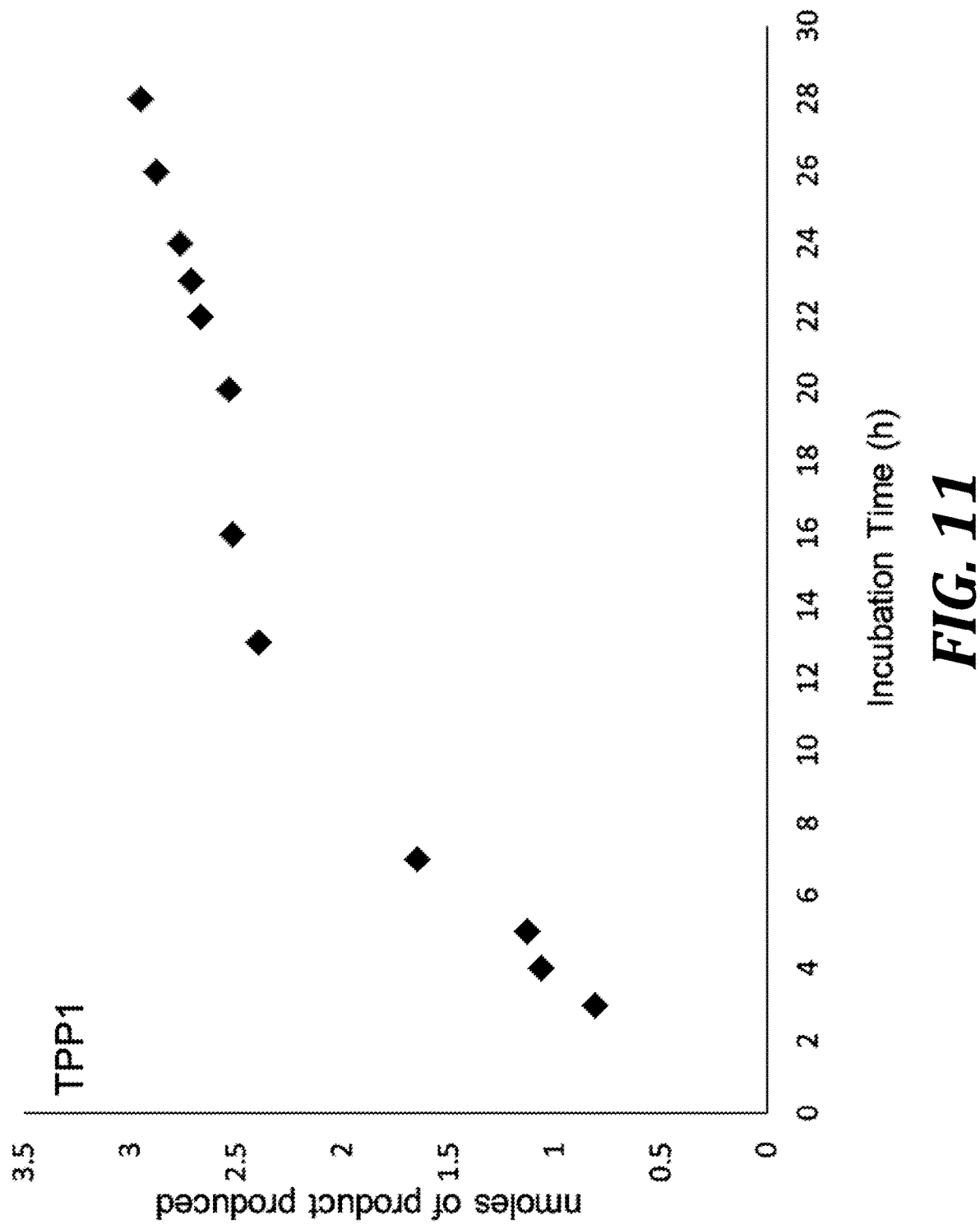
FIG. 11 is a graph of TPP1 product formation as a function of incubation time.

The PPT1 activity showed a pseudolinear increase with incubation time from 1-10 h and then it leveled off at longer incubation times (FIG. 10). The leveling-off effect can be in part due to enzymatic digestion of PPT1-P by proteolytic enzymes in rehydrated DBS. This was checked by incubating synthetic PPT1-P in the assay buffer with DBS for 18 h. The incubation resulted in 25-27% decrease of PPT1-P compared to a control sample. Since PPT1-P and PPT1-IS are similar hydrophobic peptides, it is safe to presume that their depletion will occur at similar rates and will not affect their molar ratio. The TPP1 activity showed a gradual increase with incubation time with a pseudolinear portion of the curve between 3 and 13 h (FIG. 11). Based on these measurements, the incubation time for both PPT1 and TPP1 was set at 10 h. The enzyme kinetics with respect to the synthetic substrates was established through Michaelis-Menten plots which were fitted to obtain the $K_m$ and $V_{max}$ values (FIGS. 12A and 12B). Each Michaelis-Menten curve was obtained from triplicate activity measurements over an appropriate substrate concentration range (0-500 μM and 0-300 μM). The PPT1 substrate showed $K_m$=0.23 mM and $V_{max}$=217.0 μmol $L^{-1}$ $h^{-1}$. The TPP1 substrate showed $K_m$=53.3 μM and $V_{max}$=46.0 μmol $L^{-1}$ $h^{-1}$. The measured $K_m$ were used to adjust the initial substrate concentrations in the assays to ≥2 $K_m$ value, e.g. 0.46 and 0.40 mM for PPT1-S and TPP1-S, respectively.

Assay and Sample Work-Up Conditions.

Figure 13:
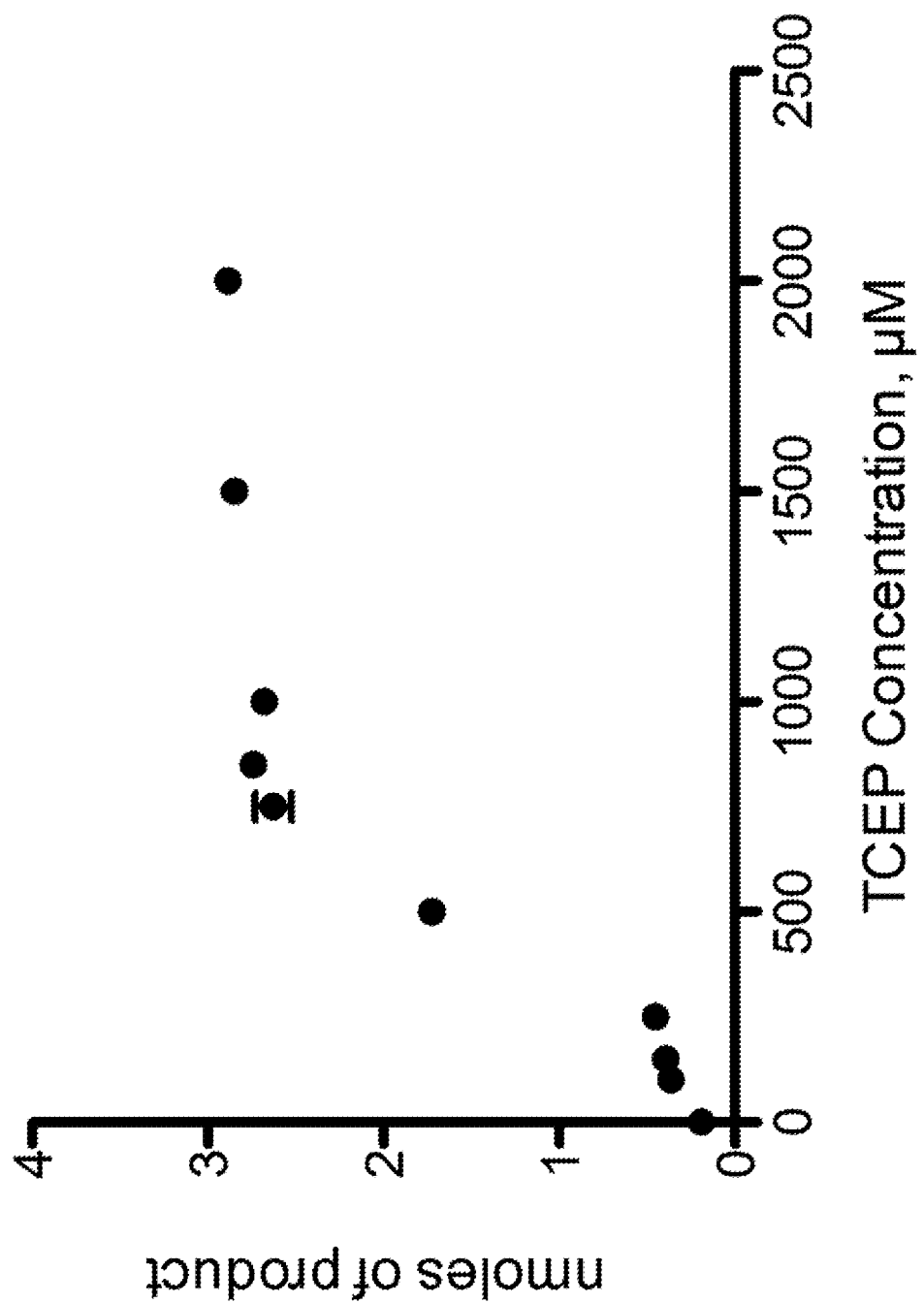
FIG. 13 is a graph showing PPT1 product amount detected by SRM as a function of the concentration of tris-(2-carboxyethy)phosphine reducing reagent.

ESI-MS/MS analysis of the assays requires that the samples be dissolved in a compatible solvent free of nonvolatile salts and detergents. The presence of a surfactant in the PPT1 assay buffer further accentuates the need for matrix removal. Liquid-liquid extraction is a well-established method of assay sample purification and it was investigated for PPT1-P and IS using different organic solvents. However, ethyl acetate, n-butanol, and 8:1:1 ethyl acetate-n-butanol-n-hexanol mixture were found to be ineffective in extracting the product and internal standard. In addition, the nonionic detergent (Triton X-100) was also extracted into the organic layer and interfered with mass spectrometric analysis. Therefore, liquid-liquid extraction with ethyl acetate was utilized to first remove Triton X-100 from the samples, while recovery of PPT1-P and IS was achieved by subsequent solid phase extraction (SPE). Standard C18 SPE pipette tips (Omix Tips) were found to selectively extract PPT1-P and IS from the aqueous phase of the assay while buffer salts can be washed away. The peptides were released by elution with a 50:50 mixture of acetonitrile-water which achieved recoveries of 52 and 50% (both ±2%) for PPT1-P and IS, respectively. This acetonitrile-water mixture does not elute the substantially more lipophilic PPT1-S from the solid phase, so the substrate does not interfere with mass spectrometric analysis. Prior to injecting the samples in the mass spectrometer, disulfide bonds spuriously formed by cysteine oxidation under the assay conditions must be reduced. TCEP was selected as the reducing agent, and the optimal concentration required for quantitative reduction was determined to be 800 mM. (FIG. 13).

Liquid-liquid extraction into ethyl acetate of TPP1-P and IS performed with 76±2% recovery in a single step. These compounds are chemically identical except for the presence of deuterium isotopes in TPP1-IS and can be expected to have similar partition coefficients for extraction into ethyl acetate. The different incubation and work up conditions for PPT1 and TPP1 assays precluded co-incubation in a single duplex assay or sample combination prior to work up. However, duplex mass spectrometric quantitation was possible, as described below.

Mass Spectrometric Response

Figure 14:
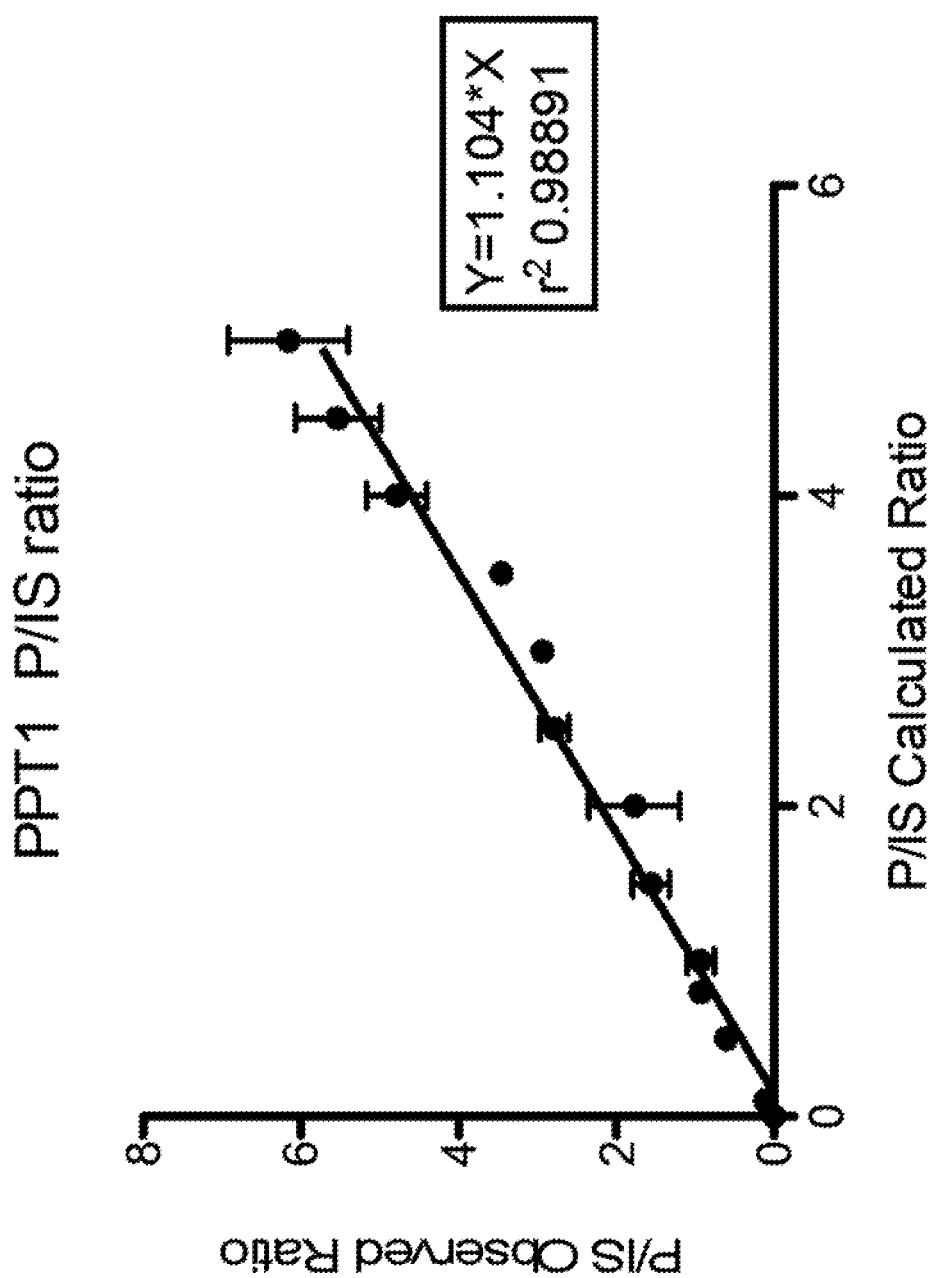
FIG. 14 is a response plot of observed SRM signal (peak areas) ratio for product and internal standard versus the theoretical concentration ratio for PPT1.
Figure 15:
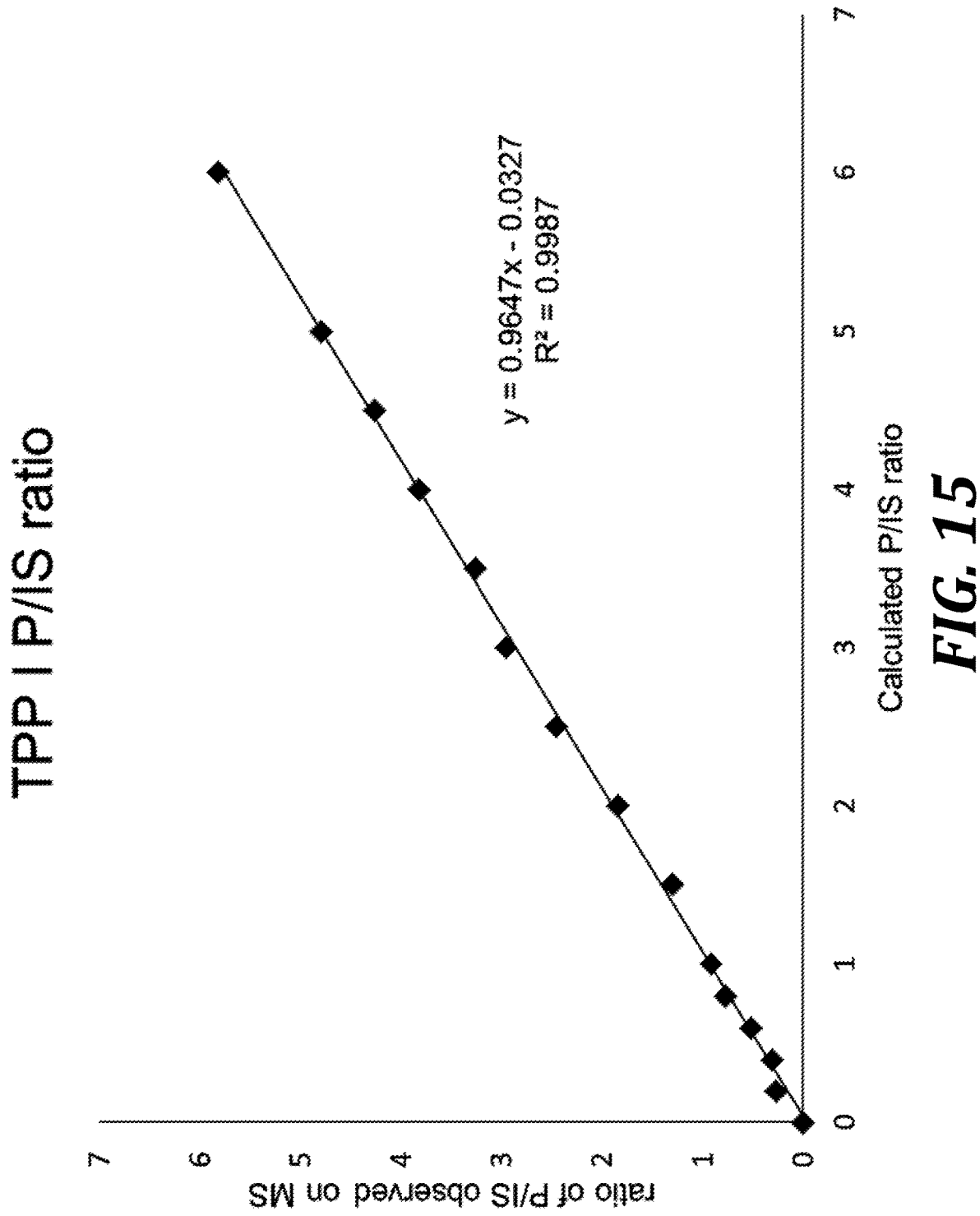
FIG. 15 is a response plot of observed SRM signal (peak areas) ratio for product and internal standard versus the theoretical concentration ratio for TPP1.

The work-up procedures for TPP1 and PPT1 products and internal standards resulted in very similar recoveries, indicating practically no bias in the concentrations of the P and IS in the samples subjected for mass spectrometric analysis. The responses in SRM for TPP1 and PPT1 products and internal standards were determined to ensure accurate quantitation of the product formation in enzyme assays. FIGS. 14 and 15 show the observed relative responses (P/IS reporter ion intensity ratios) plotted against the calculated concentration ratios. Both response curves show a satisfactory linearity ($r^2 \approx 0.99$) and slopes close to 1. SRM of PPT1-P shows about 10% higher response than PPT1-IS. The nature of this difference has not been determined, although slightly different ionization efficiencies of the N-Ac-Ala-Ala-Ala-Pro-Phe-Gly-Cys (PPT1-P) and N-Ac-Ala-Leu-Leu-Pro-Phe-Gly-Cys (PPT1-IS) peptides in electrospray as well as different ion fragmentation efficiencies for the reporter $y_4$ ion formation are not unexpected. The slope for the TPP1-P/IS response, 0.9995±0.003, $r^2=0.998$, indicated a nearly identical response to the product and internal standard.

Clinical Sample Analysis

Figure 3:
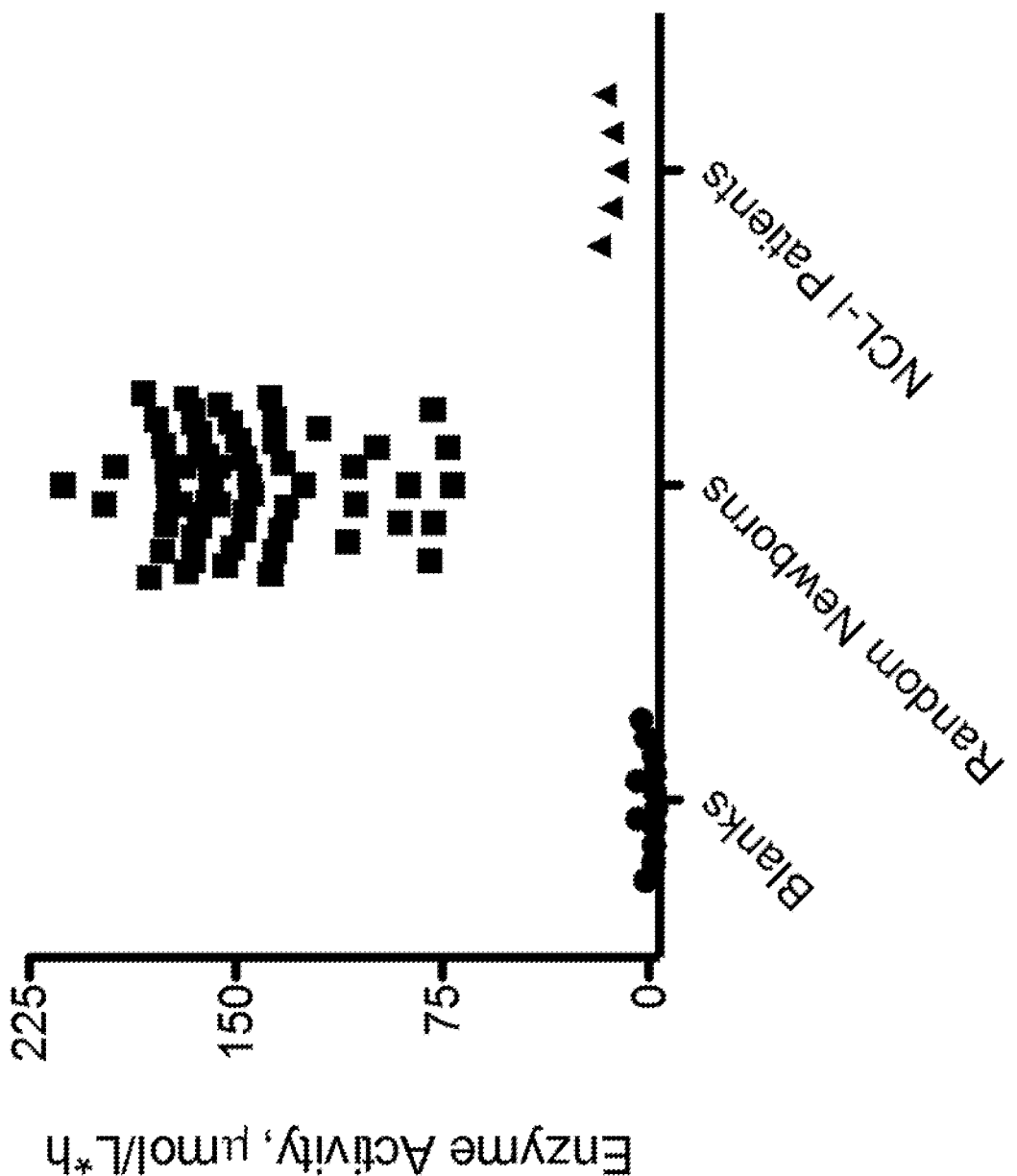
FIG. 3 is a graphical representation of PPT1 activities in DBS from simplex assays.

PPT1 assays were performed with 62 random newborn samples that were obtained from the Washington State Newborn Screening Laboratory under Institutional Review Board guidelines, and five previously diagnosed infantile NCL patients (FIG. 3). The amount of product formed was calculated using the SRM intensity ratios of the product to the internal standard, the known concentration of the internal standard, and the response ratio (P/IS=1.104, FIG. 14). The data are compiled in Table 1. A small amount of PPT1-P is formed by non-enzymatic hydrolysis of the substrate at pH 7.0, giving a mean assay/blank ratio of 16.3. Therefore, all assay data were subjected to blank correction. Enzymatic activity was calculated as µmol h$^{-1}$ (L of blood)$^{-}$ from the amount of product formed, incubation time, and volume of blood. The blood volume in the DBS was estimated at 3.2 µL, based on the estimated volume of a blood spot (10 µL) and the punch/DBS area ratio.

TABLE 1

Tandem Mass spectrometry Data for Simplex Assay of PPT1 in DBS.

| | Ion counts Product | Internal Std | Enzyme Activity (µmol/h*L) | Blank Corrected | Blank Mean |
|---|---|---|---|---|---|
| Blank | 4.65E+02 | 3.38E+03 | 10.2 | | 9.0 |
| Blank | 2.10E+02 | 1.50E+03 | 10.3 | | Blank St. Dev. |
| Blank | 4.46E+02 | 2.50E+03 | 13.1 | | 2.6 |
| Blank | 4.88E+02 | 5.05E+03 | 7.1 | | |
| Blank | 4.82E+02 | 2.63E+03 | 13.4 | | |
| Blank | 4.72E+02 | 4.86E+03 | 7.1 | | |
| Blank | 4.09E+02 | 4.62E+03 | 6.5 | | |
| Blank | 5.26E+02 | 5.41E+03 | 7.1 | | |
| Blank | 2.59E+02 | 1.63E+03 | 11.7 | | |
| Blank | 5.65E+02 | 5.71E+03 | 7.3 | | |
| Blank | 5.80E+02 | 6.09E+03 | 7.0 | | |
| Blank | 3.61E+02 | 3.56E+03 | 7.4 | | |
| Random newborn 1 | 5.23E+03 | 1.96E+03 | 187.8 | 178.7 | Random Mean |
| Random newborn 2 | 5.27E+03 | 2.08E+03 | 177.7 | 168.7 | 146.7 |
| Random newborn 3 | 4.51E+03 | 1.99E+03 | 158.2 | 149.1 | |
| Random newborn 4 | 4.08E+03 | 1.98E+03 | 142.1 | 133.1 | Random Max. |
| Random newborn 5 | 3.91E+03 | 1.77E+03 | 153.4 | 144.4 | 212.9 |
| Random newborn 6 | 4.58E+0 | 1.75E+03 | 183.8 | 174.8 | |
| Random newborn 7 | 3.29E+0 | 1.46E+03 | 156.4 | 147.4 | Random Min. |
| Random newborn 8 | 3.45E+03 | 1.38E+03 | 174.6 | 165.6 | 71.4 |
| Random newborn 9 | 3.70E+03 | 1.75E+03 | 146.7 | 137.7 | |
| Random newborn 10 | 3.56E+03 | 1.43E+03 | 174.4 | 165.4 | |
| Random newborn 11 | 2.74E+03 | 1.24E+03 | 153.9 | 144.9 | |
| Random newborn 12 | 3.57E+03 | 1.45E+03 | 172.4 | 163.3 | |
| Random newborn 13 | 3.14E+03 | 1.51E+03 | 144.8 | 135.7 | |
| Random newborn 14 | 2.46E+03 | 1.17E+03 | 146.6 | 137.6 | |
| Random newborn 15 | 3.18E+03 | 1.24E+03 | 179.1 | 170.1 | |
| Random newborn 16 | 3.48E+03 | 1.41E+03 | 172.2 | 163.2 | |
| Random newborn 17 | 3.61E+03 | 1.49E+03 | 169.7 | 160.7 | |
| Random newborn 18 | 3.15E+03 | 1.37E+03 | 160.2 | 151.2 | |
| Random newborn 19 | 3.76E+03 | 1.49E+03 | 177.0 | 168.0 | |

TABLE 1-continued

Tandem Mass spectrometry Data for Simplex Assay of PPT1 in DBS.

| | Ion counts Product | Internal Std | Enzyme Activity (µmol/h*L) | Blank Corrected | Blank Mean |
|---|---|---|---|---|---|
| Random newborn 20 | 3.83E+03 | 1.46E+03 | 184.0 | 175.0 | |
| Random newborn 21 | 3.25E+03 | 1.37E+03 | 165.6 | 156.6 | |
| Random newborn 22 | 2.75E+03 | 1.23E+03 | 156.0 | 147.0 | |
| Random newborn 23 | 4.02E+03 | 1.66E+03 | 169.4 | 160.4 | |
| Random newborn 24 | 3.69E+03 | 1.36E+03 | 190.6 | 181.5 | |
| Random newborn 25 | 2.65E+03 | 1.15E+03 | 161.3 | 152.3 | |
| Random newborn 26 | 2.60E+03 | 1.06E+03 | 172.2 | 163.2 | |
| Random newborn 27 | 3.06E+03 | 1.48E+03 | 142.9 | 133.8 | |
| Random newborn 28 | 2.52E+03 | 1.05E+03 | 168.1 | 159.1 | |
| Random newborn 29 | 3.74E+03 | 1.41E+03 | 185.5 | 176.4 | |
| Random newborn 30 | 3.23E+03 | 1.22E+03 | 185.8 | 176.8 | |
| Random newborn 31 | 3.54E+03 | 1.58E+03 | 155.6 | 146.6 | |
| Random newborn 32 | 3.59E+03 | 1.49E+03 | 168.5 | 159.5 | |
| Random newborn 33 | 3.38E+03 | 1.36E+03 | 174.6 | 165.6 | |
| Random newborn 34 | 3.71E+0 | 1.18E+03 | 221.9 | 212.9 | |
| Random newborn 35 | 2.56E+03 | 1.08E+03 | 165.7 | 156.7 | |
| Random newborn 36 | 2.93E+03 | 1.24E+03 | 165.1 | 156.1 | |
| Random newborn 37 | 3.64E+03 | 1.33E+03 | 192.8 | 183.8 | |
| Random newborn 38 | 2.57E+03 | 1.03E+03 | 174.6 | 165.6 | |
| Random newborn 39 | 5.70E+03 | 2.25E+03 | 177.2 | 168.2 | |
| Random newborn 40 | 3.88E+03 | 2.24E+03 | 118.4 | 109.4 | |
| Random newborn 41 | 3.41E+03 | 1.75E+03 | 134.7 | 125.7 | |
| Random newborn 42 | 5.22E+03 | 1.78E+03 | 207.1 | 198.0 | |
| Random newborn 43 | 3.48E+03 | 1.86E+03 | 128.8 | 119.8 | |
| Random newborn 44 | 3.70E+03 | 2.18E+03 | 116.2 | 107.2 | |
| Random newborn 45 | 3.64E+03 | 1.46E+03 | 174.6 | 165.6 | |
| Random newborn 46 | 3.43E+03 | 1.64E+03 | 145.1 | 136.1 | |
| Random newborn 47 | 2.66E+03 | 1.27E+03 | 145.0 | 136.0 | |
| Random newborn 48 | 2.79E+03 | 1.13E+03 | 172.2 | 163.1 | |
| Random newborn 49 | 2.66E+03 | 1.10E+03 | 168.2 | 159.1 | |
| Random newborn 50 | 1.79E+03 | 1.21E+03 | 99.3 | 90.3 | |
| Random newborn 51 | 1.80E+03 | 1.06E+03 | 115.6 | 106.6 | |
| Random newborn 52 | 3.17E+03 | 1.10E+03 | 202.7 | 193.7 | |
| Random newborn 53 | 1.57E+03 | 1.20E+03 | 87.4 | 78.4 | |
| Random newborn 54 | 1.23E+03 | 1.01E+03 | 80.5 | 71.4 | |
| Random newborn 55 | 1.86E+03 | 1.30E+03 | 96.3 | 87.3 | |
| Random newborn 56 | 2.17E+03 | 1.36E+03 | 107.9 | 98.9 | |
| Random newborn 57 | 1.49E+03 | 1.13E+03 | 87.6 | 78.5 | |
| Random newborn 58 | 2.45E+03 | 1.05E+03 | 163.0 | 153.9 | |
| Random newborn 59 | 2.11E+03 | 1.59E+03 | 88.5 | 79.4 | |
| Random newborn 60 | 7.28E+03 | 3.58E+03 | 140.8 | 131.7 | |
| Random newborn 61 | 1.91E+03 | 1.54E+03 | 82.3 | 73.3 | |
| Random newborn 62 | 4.56E+03 | 1.73E+03 | 184.5 | 175.5 | |
| NCL1 Patient 1 | 8.19E+02 | 1.99E+03 | 21.2 | 12.2 | NCL1 Mean |
| NCL1 Patient 2 | 1.52E+03 | 3.53E+03 | 22.8 | 13.8 | 14.9 |
| NCL1 Patient 3 | 5.95E+02 | 1.36E+03 | 23.0 | 14.0 | |
| NCL1 Patient 4 | 1.18E+03 | 2.53E+03 | 25.3 | 16.2 | |
| NCL1 Patient 5 | 7.08E+02 | 1.43E+03 | 27.3 | 18.3 | |

Unaffected newborns showed a range of PPT1 activities from 71 to 213 µmol h$^{-1}$ L$^{-1}$ with a mean at 147 µmol h$^{-1}$ L$^{-1}$. Patients affected with infantile NCL (PPT1 deficiency) displayed a range of activities between 12 and 18 µmol h$^{-1}$ L$^{-1}$ with a mean value of 15 µmol h$^{-1}$ L$^{-1}$. Blanks combining all the components of the assay but replacing the DBS punch with a filter paper punch were analyzed, and the activities were in the range of 6.5 to 13.4 µmol h$^{-1}$ L$^{-1}$ with a mean value of 9.0 µmol h$^{-1}$ L$^{-1}$. Assay precision was calculated using DBS from a healthy adult control sample. The intra-assay coefficient of variation (CV) was 3.2% (n=5), calculated from five injections of the sample from the incubation of a single DBS. The inter-assay CV was 15% that involved 10 injections from different DBS punches while avoiding the blood spot perimeter.

Figure 4:
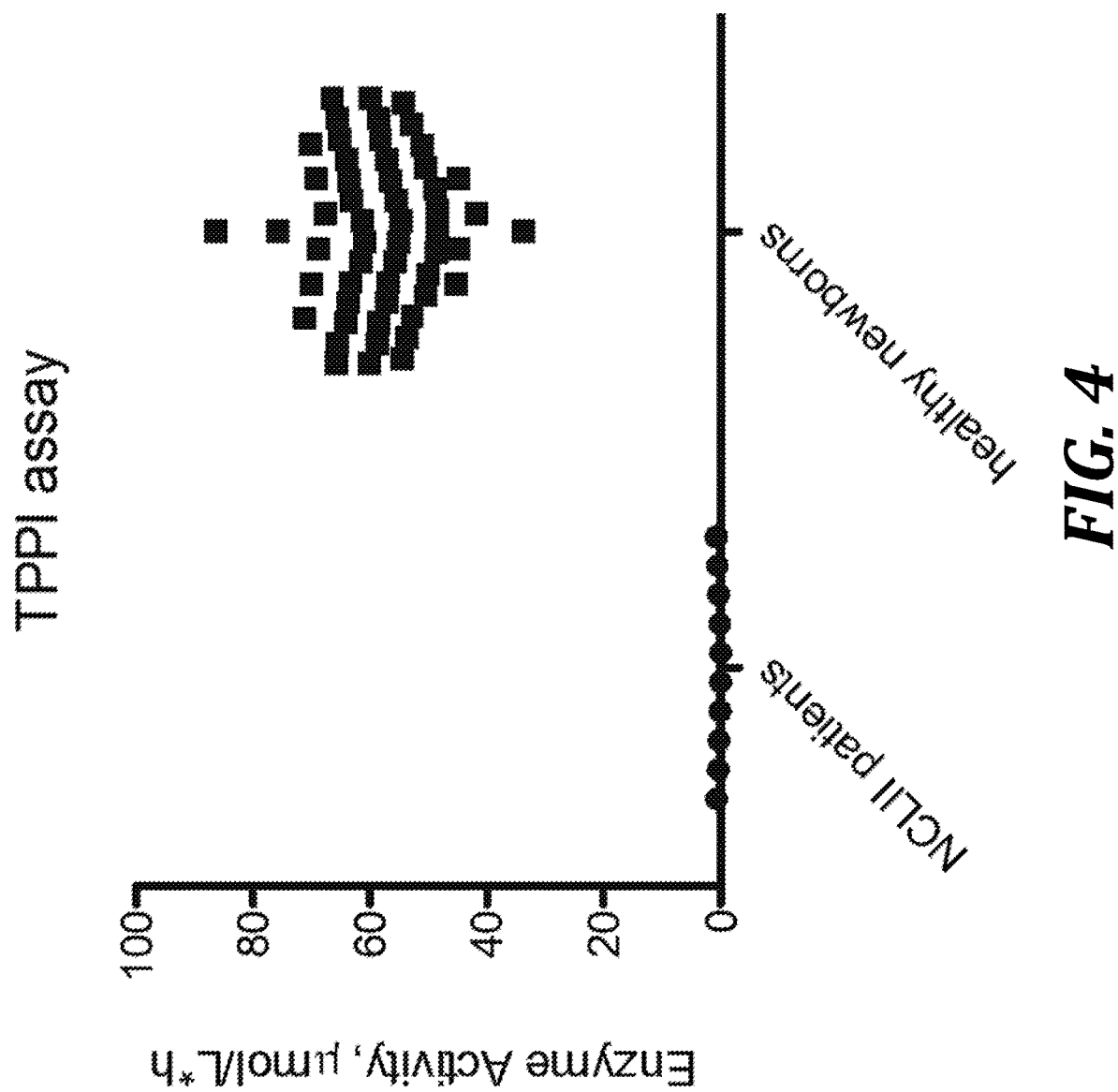
FIG. 4 is a graphical representation of TPP1 activities in DBS from simplex assays.

TPP1 assays were performed with DBS samples from 54 random newborns (Table 2), obtained with IRB approval from the Washington State Newborn Screening Laboratory, and 10 previously diagnosed NCL II patients (FIG. 4). Unaffected newborns showed a range of activities from 34 to 87 µmol h$^{-1}$ L$^{-1}$ with an average of 58 µmol h$^{-1}$ L$^{-1}$. NCL II patients (TPP1 deficiency) displayed a range between 0.02 to 0.8 µmol h$^{-1}$ L$^{1}$ and an average of 0.3 µmol h$^{-1}$ L$^{-1}$, all for blank corrected data. Blanks were carried out by combining all the components of the assay but replacing the DBS with a filter paper punch. The sample mean/blank ratios were >60 and the blanks showed 14% CV. The assays showed a clear distinction between NCL II affected patients and healthy newborns. TPP I assay precision was calculated using a DBS from a control sample. The intra-assay CV was 1.4% (n=5) involving five injections of the sample from the incubation of a single blood spot. The inter-assay CV was 8.7% when based on 15 injections from different blood spots from the same individual.

TABLE 2

Tandem Mass spectrometry Data for Simplex Assay of TPP1 in DBS.

| | peak area Product | Internal Std | Enzyme Activity ($\mu$mol/h*L) | Blank Corrected | Blank Mean |
|---|---|---|---|---|---|
| Blank | 3.36E+02 | 5.28E+04 | 2.1 | | 2.0 |
| Blank | 3.31E+02 | 5.29E+04 | 1.9 | | Blank St. Dev. |
| Blank | 3.48E+02 | 4.96E+04 | 2.0 | | 0.1 |
| Blank | 3.19E+02 | 4.89E+04 | 2.0 | | |
| Blank | 3.42E+02 | 4.86E+04 | 2.1 | | |
| Blank | 3.25E+02 | 5.27E+04 | 1.9 | | |
| Random newborn 1 | 1.17E+04 | 5.09E+04 | 67.19 | 65.2 | Random Mean |
| Random newborn 2 | 1.09E+04 | 5.35E+04 | 59.09 | 57.1 | 58.4 |
| Random newborn 3 | 1.31E+04 | 5.39E+04 | 70.89 | 68.9 | |
| Random newborn 4 | 1.04E+04 | 4.80E+04 | 63.09 | 61.1 | Random Max. |
| Random newborn 5 | 1.02E+04 | 5.18E+04 | 57.29 | 55.3 | 87.5 |
| Random newborn 6 | 1.07E+04 | 5.45E+04 | 56.89 | 54.9 | Random Min. |
| Random newborn 7 | 1.03E+04 | 5.19E+04 | 57.79 | 55.8 | 34.4 |
| Random newborn 8 | 1.30E+04 | 5.48E+04 | 69.19 | 67.2 | |
| Random newborn 9 | 1.09E+04 | 5.37E+04 | 59.19 | 57.2 | |
| Random newborn 10 | 1.10E+04 | 5.24E+04 | 60.99 | 59 | |
| Random newborn 11 | 1.25E+04 | 5.56E+04 | 65.69 | 63.7 | |
| Random newborn 12 | 1.13E+04 | 4.96E+04 | 66.09 | 64.1 | |
| Random newborn 13 | 1.16E+04 | 4.89E+04 | 68.79 | 66.8 | |
| Random newborn 14 | 1.22E+04 | 4.86E+04 | 73.19 | 71.2 | |
| Random newborn 15 | 6.74E+03 | 5.28E+04 | 36.39 | 34.4 | |
| Random newborn 16 | 1.43E+04 | 5.31E+04 | 79.09 | 77.1 | |
| Random newborn 17 | 1.04E+04 | 5.27E+04 | 57.19 | 55.2 | |
| Random newborn 18 | 9.50E+03 | 5.29E+04 | 51.99 | 50 | |
| Random newborn 19 | 1.25E+04 | 5.60E+04 | 64.89 | 62.9 | |
| Random newborn 20 | 1.00E+04 | 5.66E+04 | 51.29 | 49.3 | |
| Random newborn 21 | 1.14E+04 | 5.63E+04 | 58.99 | 57 | |
| Random newborn 22 | 1.10E+04 | 5.18E+04 | 61.79 | 59.8 | |
| Random newborn 23 | 7.75E+03 | 5.18E+04 | 42.99 | 41 | |
| Random newborn 24 | 1.31E+04 | 5.35E+04 | 71.49 | 69.5 | |
| Random newborn 25 | 1.12E+04 | 5.49E+04 | 59.29 | 57.3 | |
| Random newborn 26 | 1.08E+04 | 5.32E+04 | 58.99 | 57 | |
| Random newborn 27 | 9.48E+03 | 5.39E+04 | 50.89 | 48.9 | |
| Random newborn 28 | 1.19E+04 | 4.84E+04 | 71.59 | 69.6 | |
| Random newborn 29 | 1.20E+04 | 4.79E+04 | 73.19 | 71.2 | |
| Random newborn 30 | 1.02E+04 | 4.77E+04 | 61.99 | 60 | |
| Random newborn 31 | 1.12E+04 | 5.17E+04 | 62.89 | 60.9 | |
| Random newborn 32 | 1.59E+04 | 5.21E+04 | 89.49 | 87.5 | |
| Random newborn 33 | 1.09E+04 | 5.18E+04 | 61.29 | 59.3 | |
| Random newborn 34 | 1.30E+04 | 5.27E+04 | 71.99 | 70 | |
| Random newborn 35 | 1.19E+04 | 5.26E+04 | 66.09 | 64.1 | |
| Random newborn 36 | 8.38E+03 | 5.19E+04 | 46.49 | 44.5 | |
| Random newborn 37 | 9.10E+03 | 5.24E+04 | 50.19 | 48.2 | |
| Random newborn 38 | 9.90E+03 | 5.49E+04 | 52.29 | 50.3 | |
| Random newborn 39 | 1.30E+04 | 5.63E+04 | 67.69 | 65.7 | |
| Random newborn 40 | 8.95E+03 | 5.55E+04 | 46.59 | 44.6 | |
| Random newborn 41 | 9.22E+03 | 5.32E+04 | 50.09 | 48.1 | |
| Random newborn 42 | 9.29E+03 | 5.17E+04 | 51.99 | 50 | |
| Random newborn 43 | 9.70E+03 | 5.18E+04 | 54.29 | 52.3 | |
| Random newborn 44 | 1.13E+04 | 4.77E+04 | 68.69 | 66.7 | |
| Random newborn 45 | 1.28E+04 | 5.66E+04 | 66.19 | 64.2 | |
| Random newborn 46 | 1.14E+04 | 5.24E+04 | 63.09 | 61.1 | |
| Random newborn 47 | 1.03E+04 | 5.33E+04 | 55.89 | 53.9 | |
| Random newborn 48 | 1.06E+04 | 5.10E+04 | 60.09 | 58.1 | |
| Random newborn 49 | 1.12E+04 | 5.43E+04 | 59.79 | 57.8 | |
| Random newborn 50 | 8.71E+03 | 5.00E+04 | 50.29 | 48.3 | |
| Random newborn 51 | 9.45E+03 | 5.05E+04 | 54.19 | 52.2 | |
| Random newborn 52 | 9.99E+03 | 5.19E+04 | 55.79 | 53.8 | |
| Random newborn 53 | 9.61E+03 | 5.20E+04 | 53.49 | 51.5 | |
| Random newborn 54 | 9.44E+03 | 5.18E+04 | 52.69 | 50.7 | |
| NCL2 Patient 1 | 6.86E+02 | 5.17E+04 | 2.04 | 0.05 | NCL2 Mean |
| NCL2 Patient 2 | 6.95E+02 | 5.18E+04 | 2.09 | 0.1 | 0.33 |
| NCL2 Patient 3 | 7.30E+02 | 5.18E+04 | 2.29 | 0.3 | |
| NCL2 Patient 4 | 7.54E+02 | 5.27E+04 | 2.39 | 0.4 | |
| NCL2 Patient 5 | 8.33E+02 | 5.36E+04 | 2.79 | 0.8 | |

Duplex Analysis

Figure 16:
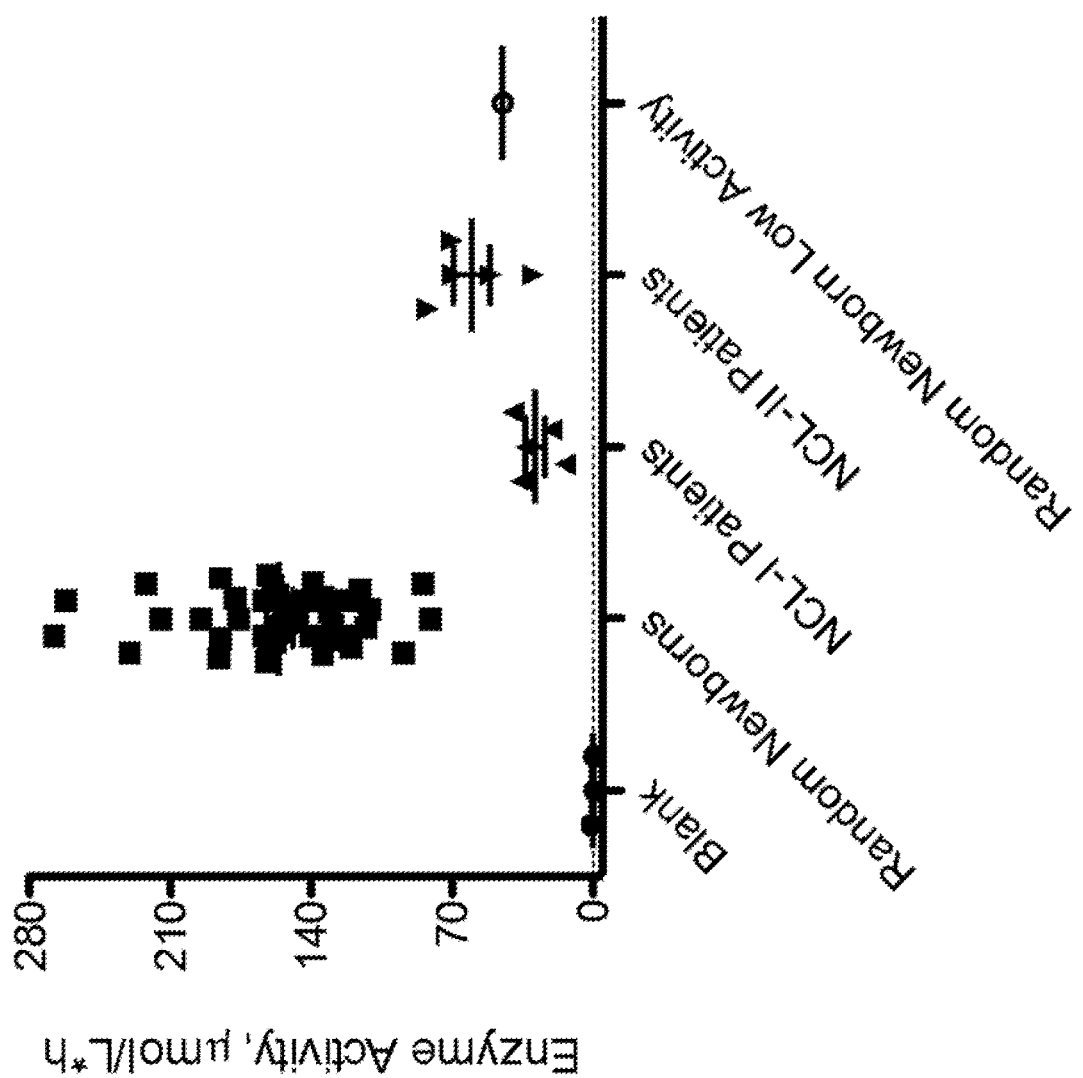
FIG. 16 is a graphical representation of PPT1 and TPP1 activities in DBS from duplex assays.

The PPT1 and TPP1 assays were combined in a single injection for tandem mass spectrometry SRM analysis with the goal of speeding up data acquisition and increasing sample throughput. Due to different assay pH conditions and work-up procedures, the assays could not be run as single DBS incubations, but rather samples from each assay were combined after workup. The results of this duplex assay of 40 random samples are presented in FIG. 16 and the data are compiled in Table 3 In the duplex format, random samples showed PPT1 activities in the range of 81 to 268 $\mu$mol h$^{-1}$ L$^{-1}$ with a mean activity of 156 $\mu$mol h$^{-1}$ L$^{-1}$. These results were comparable to the data from the above-described simplex PPT1 assay. The five infantile NCL-affected newborns had a range of activity of 14-40 $\mu$mol h$^{-1}$ L$^{-1}$, with a mean at 29 $\mu$mol h$^{-1}$ L$^{-1}$. The PPT1 activity of the five late infantile NCL II affected newborns (TPP1 deficiency) ranged between 30 and 82 $\mu$mol h$^{-1}$ L$^{-1}$, with an average activity of 61 mmol $h^{-1}$ $L^{-1}$. This was lower than the mean activity for random TPP1 samples, but within the normal range. Blanks were evaluated for the duplex assay to produce PPT1 activities of 13 to 15 mmol $h^{-1}$ $L^{-1}$ with a mean of 14 mmol $h^{-1}$ $L^{-1}$.

TABLE 3

Tandem Mass spectrometry Data for Duplex Assay of PPT1 in DBS.

|  | Ion Counts Product | Int Std | Enzyme Activity | Blank Corrected | Blank Mean |
|---|---|---|---|---|---|
| Blank | 4.47E+02 | 2.44E+03 | 13.5 |  | 13.9 |
| Blank | 3.94E+02 | 1.95E+03 | 14.9 |  | Blank St. Dev. |
| Blank | 4.60E+02 | 2.55E+03 | 13.3 |  | 0.9 |
| Random newborn 1 | 4.42E+03 | 2.00E+03 | 148.4 | 134.5 |  |
| Random newborn 2 | 4.20E+03 | 2.22E+03 | 125.2 | 111.3 |  |
| Random newborn 3 | 4.80E+03 | 2.19E+03 | 147.7 | 133.8 | Random Mean |
| Random newborn 4 | 4.23E+03 | 2.16E+03 | 130.1 | 116.2 | 156.2 |
| Random newborn 5 | 4.49E+03 | 1.73E+03 | 177.5 | 163.6 |  |
| Random newborn 6 | 3.28E+03 | 1.27E+03 | 176.6 | 162.7 | Random Max. |
| Random newborn 7 | 4.20E+03 | 1.69E+03 | 169.5 | 155.6 | 267.9 |
| Random newborn 8 | 4.47E+03 | 2.09E+03 | 143.2 | 129.3 |  |
| Random newborn 9 | 6.28E+03 | 2.61E+03 | 163.0 | 149.1 | Random Min. |
| Random newborn 10 | 4.54E+03 | 1.99E+03 | 154.2 | 140.3 | 81.1 |
| Random newborn 11 | 5.32E+03 | 1.52E+03 | 244.4 | 230.5 |  |
| Random newborn 12 | 5.20E+03 | 2.25E+03 | 156.2 | 142.3 |  |
| Random newborn 13 | 3.84E+03 | 2.32E+03 | 108.1 | 94.2 |  |
| Random newborn 14 | 4.13E+03 | 2.05E+03 | 134.5 | 120.6 |  |
| Random newborn 15 | 3.35E+03 | 2.27E+03 | 95.0 | 81.1 |  |
| Random newborn 16 | 5.27E+03 | 2.32E+03 | 153.2 | 139.2 |  |
| Random newborn 17 | 4.75E+03 | 1.92E+03 | 168.2 | 154.3 |  |
| Random newborn 18 | 5.70E+03 | 2.64E+03 | 145.0 | 131.1 |  |
| Random newborn 19 | 5.52E+03 | 1.99E+03 | 190.5 | 176.6 |  |
| Random newborn 20 | 6.14E+03 | 2.41E+03 | 173.3 | 159.4 |  |
| Random newborn 21 | 4.68E+03 | 1.61E+03 | 199.7 | 185.8 |  |
| Random newborn 22 | 4.62E+03 | 2.14E+03 | 145.0 | 131.1 |  |
| Random newborn 23 | 6.23E+03 | 2.15E+03 | 199.2 | 185.2 |  |
| Random newborn 24 | 6.50E+03 | 2.52E+03 | 175.6 | 161.7 |  |
| Random newborn 25 | 6.36E+03 | 2.67E+03 | 161.1 | 147.2 |  |
| Random newborn 26 | 5.14E+03 | 3.36E+03 | 98.5 | 84.6 |  |
| Random newborn 27 | 6.31E+03 | 1.91E+03 | 228.9 | 215.0 |  |
| Random newborn 28 | 6.17E+03 | 3.23E+03 | 126.8 | 112.8 |  |
| Random newborn 29 | 3.65E+03 | 1.78E+03 | 136.7 | 122.8 |  |
| Random newborn 30 | 4.87E+03 | 1.93E+03 | 172.2 | 158.3 |  |
| Random newborn 31 | 4.82E+03 | 1.85E+03 | 177.4 | 163.5 |  |

TABLE 3-continued

Tandem Mass spectrometry Data for Duplex Assay of PPT1 in DBS.

|  | Ion Counts Product | Int Std | Enzyme Activity | Blank Corrected | Blank Mean |
|---|---|---|---|---|---|
| Random newborn 32 | 5.09E+03 | 1.76E+03 | 199.3 | 185.4 |  |
| Random newborn 33 | 5.24E+03 | 2.09E+03 | 170.9 | 157.0 |  |
| Random newborn 34 | 5.34E+03 | 2.60E+03 | 137.4 | 123.5 |  |
| Random newborn 35 | 5.91E+03 | 1.74E+03 | 236.2 | 222.3 |  |
| Random newborn 36 | 3.94E+03 | 1.30E+03 | 208.9 | 195.0 |  |
| Random newborn 37 | 3.31E+03 | 1.18E+03 | 192.2 | 178.3 |  |
| Random newborn 38 | 7.31E+03 | 1.82E+03 | 281.8 | 267.9 |  |
| Random newborn 39 | 7.17E+03 | 1.82E+03 | 276.3 | 262.4 |  |
| Random newborn 40 | 4.46E+03 | 1.73E+03 | 176.0 | 162.1 |  |
| random newborn low activity | 1.68E+03 | 2.09E+03 | 45.3 |  |  |
| NCL1 Patient 1 | 1.36E+03 | 1.63E+03 | 47.4 | 33.5 | NCL1 Mean |
| NCL1 Patient 2 | 9.12E+02 | 1.59E+03 | 28.3 | 14.4 | 29.1 |
| NCL1 Patient 3 | 1.45E+03 | 1.57E+03 | 53.9 | 40.0 | NCL1 St. Dev. |
| NCL1 Patient 4 | 1.22E+03 | 1.41E+03 | 49.9 | 36.0 | 10.8 |
| NCL1 Patient 5 | 8.89E+02 | 1.33E+03 | 35.2 | 21.3 |  |
| NCL2 Patient 1 | 1.52E+03 | 1.93E+03 | 43.8 | 29.9 | NCL2 Mean |
| NCL2 Patient 2 | 1.62E+03 | 1.23E+03 | 83.4 | 69.5 | 60.6 |
| NCL2 Patient 3 | 1.89E+03 | 1.42E+03 | 84.3 | 70.4 |  |
| NCL2 Patient 4 | 1.96E+03 | 1.31E+03 | 96.1 | 82.2 |  |
| NCL2 Patient 5 | 9.94E+02 | 9.31E+02 | 64.8 | 50.9 |  |

Figure 17:
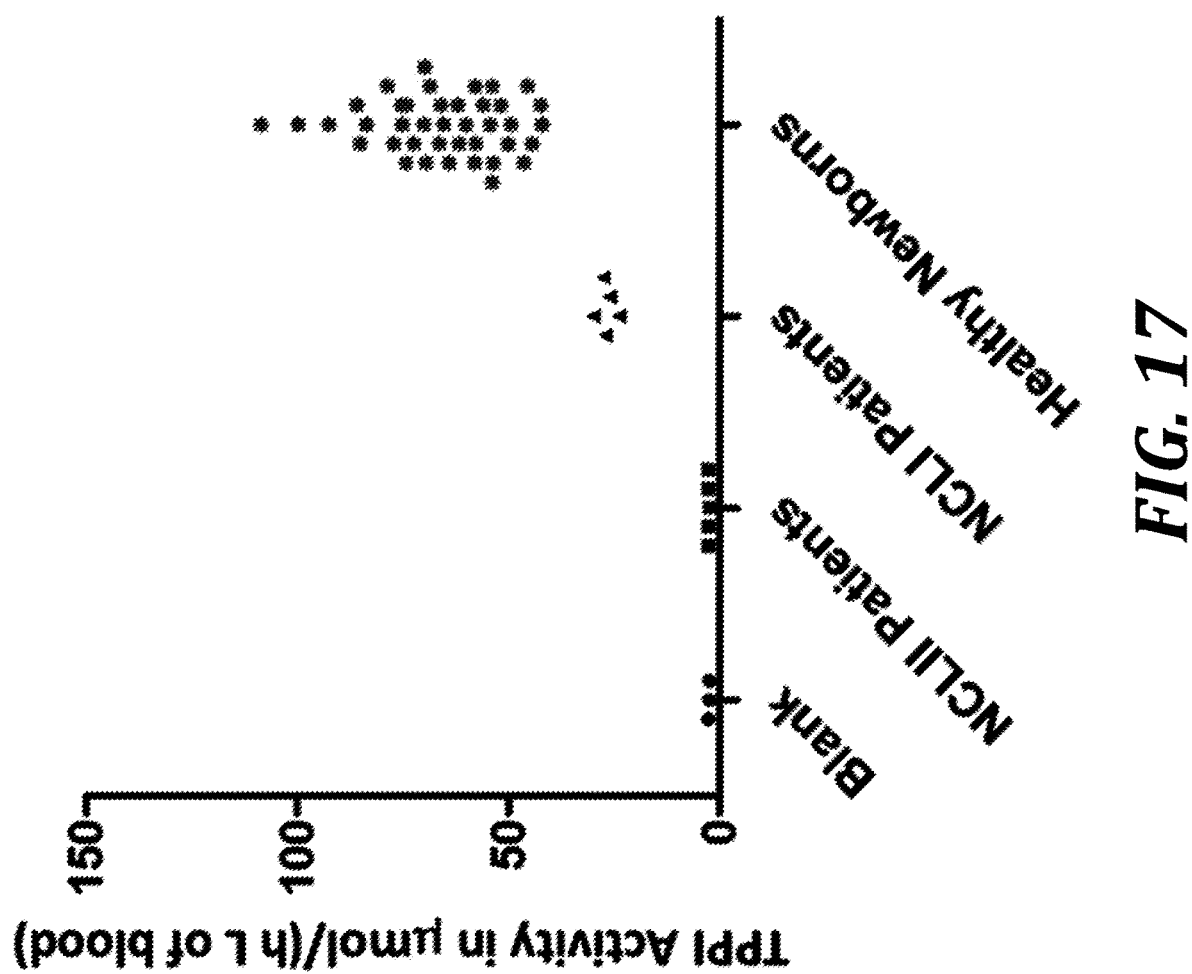
FIG. 17 is a graphical representation of TPP1 and PPT1 activities in DBS from duplex assays.

Duplex data from incubation of TPP1 activity in forty random samples gave a range of activities 40 to 106 µmol $h^{-1}$ $L^{-1}$ with a mean activity of 63 µmol $h^{-1}$ $L^{-1}$ (FIG. 17, Table 4) These values are comparable to those from simplex assay measurements with a different set of 54 random samples (see above). TPP1 activity of five NCL II (TPP1 deficiency) affected newborns ranged between 2.6 and 2.8 µmol $h^{-1}$ $L^{-1}$ with an average activity of 2.7 µmol $h^{-1}$ $L^{-1}$, which dropped to 0.2 µmol $h^{-1}$ $L^{-1}$ after blank correction. The TPP1 activity for the affected individuals from the duplex assay were very similar to those from the simplex assay. The TPP1 activities of the five infantile NCL1 affected newborns with diagnosed PPT1 deficiency had a mean of 27 µmol $h^{-1}$ $L^{-1}$, which was at the low end but still within the normal range for random samples.

TABLE 4

Tandem Mass spectrometry Data for Duplex Assay of TPP1 in DBS.

|  | Peak area | | Enzyme | Blank | Blank Mean |
|---|---|---|---|---|---|
|  | Product | Int Std | Activity | Corrected | 2.51 |
| Blank | 5.67E+02 | 3.90E+04 | 2.4 |  | Blank St. Dev. |
| Blank | 5.34E+02 | 3.79E+04 | 2.4 |  | 0.2 |

TABLE 4-continued

Tandem Mass spectrometry Data for Duplex Assay of TPP1 in DBS.

| | Peak area | | Enzyme | Blank | Blank Mean |
|---|---|---|---|---|---|
| | Product | Int Std | Activity | Corrected | 2.51 |
| Blank | 6.99E+02 | 3.45E+04 | 2.7 | | |
| Random newborn 1 | 3.83E+04 | 3.70E+04 | 52.0 | 49.5 | Random Mean |
| Random newborn 2 | 4.33E+04 | 3.74E+04 | 58.0 | 55.5 | 63.2 |
| Random newborn 3 | 3.07E+04 | 3.33E+04 | 46.5 | 44.0 | Random Max. |
| Random newborn 4 | 3.64E+04 | 3.70E+04 | 49.6 | 47.0 | 106.3 |
| Random newborn 5 | 5.97E+04 | 3.19E+04 | 92.6 | 90.1 | Random Min. |
| Random newborn 6 | 5.19E+04 | 2.99E+04 | 86.0 | 83.5 | 39.7 |
| Random newborn 7 | 3.85E+04 | 3.58E+04 | 53.9 | 51.4 | |
| Random newborn 8 | 3.48E+04 | 3.24E+04 | 53.7 | 51.2 | |
| Random newborn 9 | 4.32E+04 | 3.24E+04 | 66.4 | 63.9 | |
| Random newborn 10 | 4.75E+04 | 3.44E+04 | 68.7 | 66.2 | |
| Random newborn 11 | 4.37E+04 | 3.40E+04 | 64.2 | 61.7 | |
| Random newborn 12 | 4.60E+04 | 3.46E+04 | 66.1 | 63.6 | |
| Random newborn 13 | 2.14E+04 | 2.56E+04 | 42.2 | 39.7 | |
| Random newborn 14 | 3.98E+04 | 2.84E+04 | 69.8 | 67.3 | |
| Random newborn 15 | 3.18E+04 | 2.92E+04 | 54.5 | 52.0 | |
| Random newborn 16 | 3.81E+04 | 3.30E+04 | 57.8 | 55.3 | |
| Random newborn 17 | 3.87E+04 | 3.13E+04 | 61.8 | 59.2 | |
| Random newborn 18 | 3.54E+04 | 2.52E+04 | 70.1 | 67.6 | |
| Random newborn 19 | 4.19E+04 | 2.81E+04 | 74.2 | 71.6 | |
| Random newborn 20 | 3.15E+04 | 3.57E+04 | 44.6 | 42.0 | |
| Random newborn 21 | 3.19E+04 | 2.96E+04 | 53.9 | 51.4 | |
| Random newborn 22 | 3.88E+04 | 3.12E+04 | 62.0 | 59.5 | |
| Random newborn 23 | 2.64E+04 | 2.93E+04 | 45.6 | 43.1 | |
| Random newborn 24 | 4.55E+04 | 2.92E+04 | 77.2 | 74.7 | |
| Random newborn 25 | 4.15E+04 | 2.74E+04 | 75.1 | 72.6 | |
| Random newborn 26 | 3.83E+04 | 2.92E+04 | 65.4 | 62.9 | |
| Random newborn 27 | 4.76E+04 | 2.77E+04 | 85.2 | 82.7 | |
| Random newborn 28 | 2.71E+04 | 2.42E+04 | 56.1 | 53.6 | |
| Random newborn 29 | 2.69E+04 | 2.70E+04 | 50.2 | 47.7 | |
| Random newborn 30 | 3.98E+04 | 2.84E+04 | 69.6 | 67.1 | |
| Random newborn 31 | 4.15E+04 | 2.74E+04 | 75.4 | 72.9 | |
| Random newborn 32 | 4.61E+04 | 2.73E+04 | 83.7 | 81.2 | |
| Random newborn 33 | 3.40E+04 | 2.27E+04 | 74.3 | 71.8 | |
| Random newborn 34 | 4.01E+04 | 2.76E+04 | 72.4 | 69.9 | |
| Random newborn 35 | 1.61E+04 | 7.97E+03 | 99.8 | 97.3 | |
| Random newborn 36 | 1.70E+04 | 7.68E+03 | 108.8 | 106.3 | |
| Random newborn 37 | 7.56E+03 | 6.27E+03 | 60.2 | 57.7 | |
| Random newborn 38 | 4.09E+04 | 2.58E+04 | 78.7 | 76.2 | |
| Random newborn 39 | 3.97E+04 | 3.42E+04 | 58.1 | 55.6 | |
| Random newborn 40 | 2.25E+04 | 2.68E+04 | 42.5 | 40.0 | |
| random newborn low activity | 2.12E+04 | 2.60E+04 | 41.3 | | |
| NCL1 Patient 1 | 1.62E+04 | 3.25E+04 | 26.0 | 23.5 | Mean NCL1 |
| NCL1 Patient 2 | 1.53E+04 | 3.42E+04 | 23.6 | 21.1 | 26.8 |
| NCL1 Patient 3 | 1.42E+04 | 2.70E+04 | 27.4 | 24.9 | |
| NCL1 Patient 4 | 1.59E+04 | 2.74E+04 | 29.8 | 27.3 | |
| NCL1 Patient 5 | 1.22E+04 | 2.35E+04 | 26.9 | 24.4 | |
| NCL2 Patient 1 | 6.02E+02 | 3.02E+04 | 2.7 | 0.2 | Mean NCL2 |
| NCL2 Patient 2 | 6.65E+02 | 2.85E+04 | 2.9 | 0.3 | 0.2 |
| NCL2 Patient 3 | 4.85E+02 | 2.42E+04 | 2.7 | 0.2 | |
| NCL2 Patient 4 | 4.43E+02 | 2.46E+04 | 2.6 | 0.1 | |
| NCL2 Patient 5 | 5.58E+02 | 2.55E+04 | 2.8 | 0.3 | |

The new substrates showed robust performance in PPT1 and TPP1 assays based on tandem mass spectrometric activity measurements. Compared to fluorometric assays, the new protocols do not require enzyme extraction from the DBS nor chloroform extraction of the PPT1 substrate, which may be problematic in a clinical laboratory. Enzymatic product formation from the new substrates was several times higher that in the fluorometric assays. For example, a 46 h incubation of the fluorometric PPT1 substrate was reported to produce on average 0.82 nmol of product per a DBS. Our new PPT1 substrate was shown to produce on average 4.7 nmol of product per one DBS after 10 h incubation. The fluorometric TPP1 substrate was reported to produce on average 0.27 nmol of product per a DBS after 46 h incubation. This is to be compared with 1.7 nmol/DBS produced from our new substrate after 10 h incubation. These product quantities, when combined with efficient liquid-liquid or solid-phase extraction procedures, provide high ion counts in the mass spectrometric analysis by SRM.

The lower activities measured in samples from the cross-affected children are most likely due to partial deterioration of the enzymes in the DBS. Whereas the DBS from random newborns were less than 6 months old and were stored at low temperature, the much rarer samples from the affected children had been collected over several years and were stored at room temperature. A 15% decrease of TPP1 activity was observed in a 6-month old DBS that was stored for additional 12 months at 4° C. A more systematic study of DBS aging carried out with multiple samples would be necessary to address this issue before the PPT1 and TPP1 activity assays are used for large-scale screening.

The results reported here illustrate the power of tandem mass spectrometry in performing enzyme assays in dried blood spots from human subjects using synthetic compounds that closely mimic natural substrates. Using this approach it is possible to increase enzymatic product formation in the DBS to facilitate accurate quantitation of enzyme activity. Through careful design of enzyme substrates and internal standards for human palmitoyl protein thioesterase and tripeptidyl peptidase, the analytical procedures for the detection of neuronal ceroid lipofuscinoses can be multiplexed with each other as well as with the previously developed methods of detecting lysosomal enzyme deficiencies.

Substrate Synthesis

PPT1 Substrate Synthesis

The substrate for PPT1 was prepared by S-acylation of peptide ALLPFGC following a procedure reported by Rijkers et al. and summarized in Scheme 1. N-Acetylated peptide ALLPFGC (20 mg, 26.3 µmol, Lifetein, Hillsborough, N.J.) was dissolved in a 3:1 mixture of dichloromethane/dimethylformamide and mixed with triethylamine (73 µL, 523 µmol). After stirring for 5 minutes, 0.1 M solution of palmitoyl chloride (162 µL, 525 µmol) in dichloromethane was added slowly. The mixture was allowed to react for 15 hours at room temperature. Upon reaction completion the solvent was removed under reduced pressure. The product was redissolved in acetonitrile and filtered. The filtered solution was purified by column chromatography on silica gel, elution with a 5:1 dichloromethane/methanol mixture containing 0.5% acetic acid ($R_f$ 0.76). The substrate was isolated as a white solid in 69% yield (18.1 mg, 18.1 µmol). Mass spectrometry data confirmed the identity of the substrate.

Scheme 1. Synthesis of the palmitoylated substrate for PPT1. See, e.g., Rijkers, D., Kruijtzer, J., Killian, J. A., Liskamp, R. M. J. A convenient solid phase synthesis of S-palmitoyl transmembrane peptides. *Tetrahedron Lett.* 2005, 46, 3341-3345.

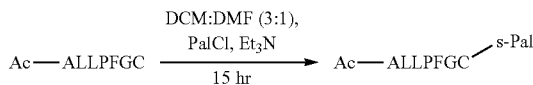

TPP1 Substrate Synthesis

The synthetic steps are shown in Scheme 2 and described below.

Step 1:

tert-Butyl phenyl carbonate (9.7 mL, 50 mmol) was added to a solution of 1,3-diaminopropane (3.7 mL, 50 mmol) in 35 mL ethanol in a 200-mL, single-necked, round-bottomed flask equipped with a stirring bar and a reflux condenser.[s2] The reaction mixture was heated gently to reflux overnight ensuring that the temperature was in the range of 80-85° C., resulting in a yellow solution. The reaction mixture was cooled to room temperature and the solution was concentrated to approximately 7-8 mL using a rotary evaporator, which left a yellow solution. Water (50 mL) was added and pH was adjusted to approximately pH 3 by careful addition of aqueous HCl, followed by extraction with $CH_2Cl_2$ (3×80 mL). The aqueous layer was adjusted to pH 13 by the addition of 2M NaOH and extracted with $CH_2Cl_2$ (5×100 mL). The combined organic extracts were concentrated using a rotary evaporator to afford 2.8 g of a yellow oil which crystallized within ~1 h. Yield: 33% MW: 174.2 MS: m/z 175.0 $[M+H]^+$ Scheme 2.

Step 1

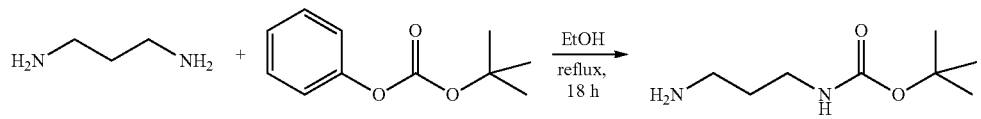

Step 2

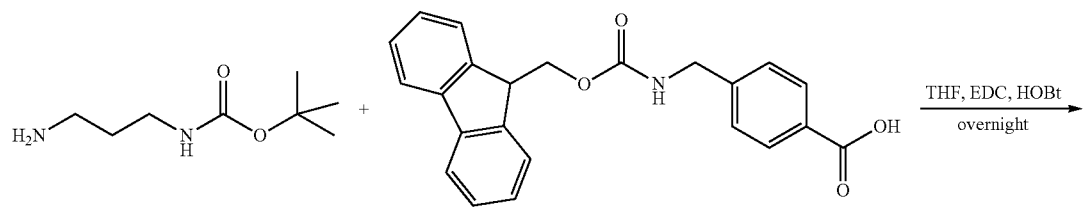

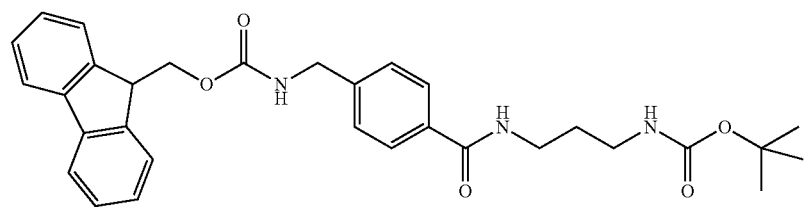

-continued
Step 3
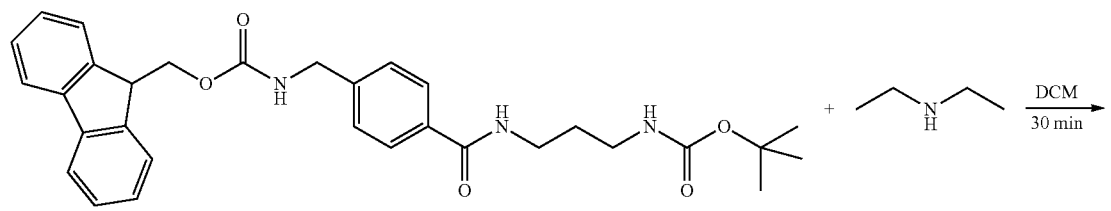
Step 4
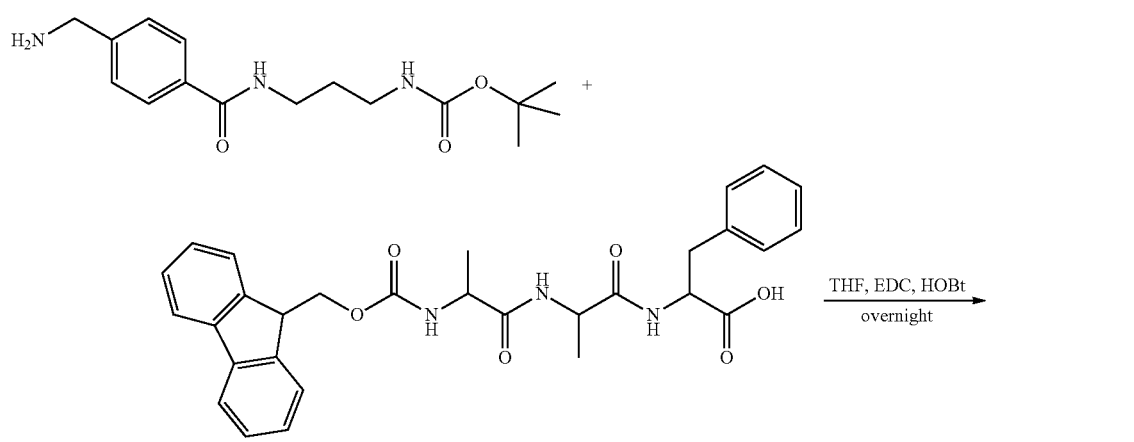
Step 5
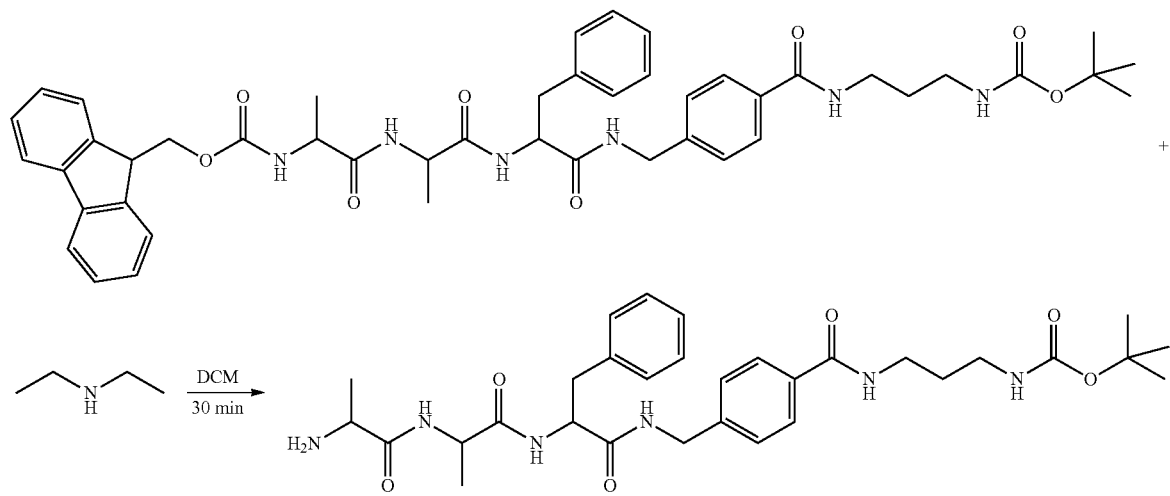

Step 2:

A solution of Fmoc-4-aminomethylbenzoic acid (74.7 mg, 0.2 mmol, 1 eq) in 10 mL of anhydrous tetrahydrofuran was cooled to 0° C. on ice. N-(3-Dimethylaminopropyl)-N'-ethylcarbodiimide hydrochloride (42.2 mg, 0.22 mmol, 1.1 eq) and 1-hydroxybenzotriazole (27.1 mg, 0.22 mmol, 1.1 eq) were added, and the suspension was stirred for 30 min at 0° C. A solution of N-Boc-1,3-diaminopropane (34.8 mg, 0.2 mmol, 1 eq) in 2 mL of N,N-dimethylformamide was added dropwise to the suspension. The reaction mixture was allowed to warm to room temperature and then was stirred overnight. The reaction mixture was concentrated using a rotary evaporator. The residue was taken up in ethyl acetate (100 mL), and then washed with 1M HCl (80 mL) and water (3×80 mL). The organic solvent was evaporated using a rotary evaporator. The solid product was purified by crystallization from isopropyl alcohol to give the pure compound. MW=529.4 MS: m/z 552.4 [M+Na]$^+$.

Step 3:

A mixture of the Fmoc-protected product synthesized in Step 2 (80 mg, 0.15 mmol) was dissolved in 6 mL of a diethylamine (DEA)/dichloromethane mixture (v/v=1:1). The mixture was magnetically stirred until the white colored solution turned yellow (approximately 30 min). The organic solvent was evaporated using a rotary evaporator and the residual mass (yellow oil) was purified by column chromatography (SiO$_2$, particle size 40-63 μm) using stepped gradient of ethyl acetate:methanol (100→80:20), 1% triethylamine. The 80:20 fraction was evaporated on a rotary evaporator. The sample was left in a desiccator for a day or two to afford crystals that had a yellow tint. Yield: 82% MW: 307.3 MS: m/z 308.3 [M+H]$^+$; m/z 615.3 [2M+H]$^+$;

$^1$H-NMR (CDCl$_3$): 1.38 (s, 9H), 1.65 (m, 2H), 3.06 (t, 2H), 3.25 (t, 2H), 4.07 (s, 2H), 7.58 (d, 2H), 7.89 (d, 2H).

Step 4:

A solution of Fmoc-AAF (4 mg, 0.008 mmol, 1 eq) in 2 mL of anhydrous tetrahydrofuran was cooled to 0° C. on ice. N-(3-Dimethylaminopropyl)-N'-ethylcarbodiimide hydrochloride (1.6 mg, 0.0085 mmol, 1.1 eq) and 1-hydroxybenzotriazole (1.15 mg, 0.0085 mmol, 1.1 eq) were added, and the suspension was stirred for 30 min at 0° C. A solution of the product from step 3 (2.5 mg, 0.008 mmol, 1 eq) in 200 μL of N,N-dimethylformamide was added drop-wise to the suspension. The reaction mixture was allowed to warm to room temperature and then stirred overnight. Then it was concentrated using a rotary evaporator. The residue was taken up in ethyl acetate (5 mL) and washed with 1M HCl (5 mL), then water (3×5 mL). The organic solvent was evaporated using a rotary evaporator. The solid product was washed with hot 2-propanol, filtered, and dried. The product was a white solid. Yield: 65% MW: 818.9 Step 5:

A mixture of Fmoc-protected product synthesized in Step 4 (4.1 mg, 0.005 mmol) was dissolved in 1 mL of diethylamine (DEA)/dichloromethane (v/v=1:1) mixture. The mixture was magnetically stirred until the white colored solution turned yellow (approximately 30 min). The organic solvent was evaporated using rotary evaporator and the residual mass (yellow oil) was purified by column chromatography (SiO$_2$, particle size 40-63 μm) using dichloromethane:ethyl acetate (v/v=1:1), with 1% triethylamine followed by dichloromethane:ethyl acetate:methanol (v/v/v=1:1:0.5) with 1% triethylamine to elute the substrate. Yield: 79% MW: 596.6. MS: m/z 597.7 (M+H$^+$).

TPP1 Internal Standard Synthesis

Scheme 3.

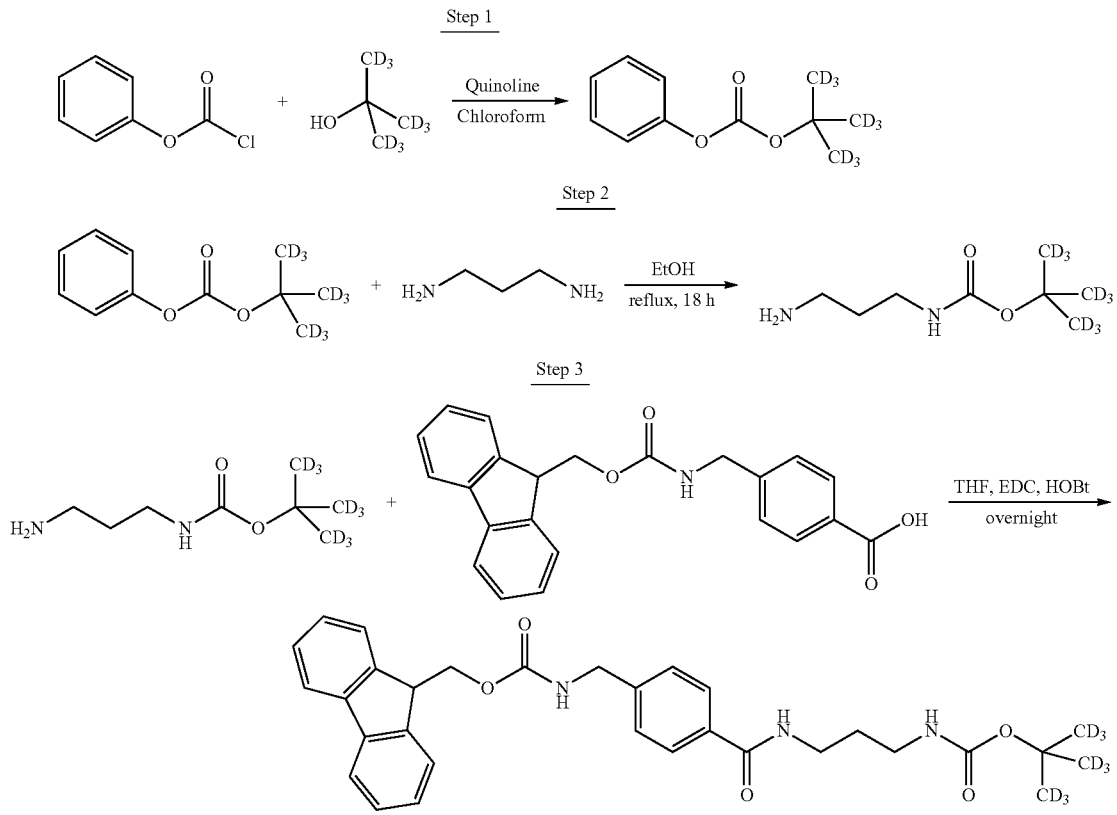

-continued

Step 4

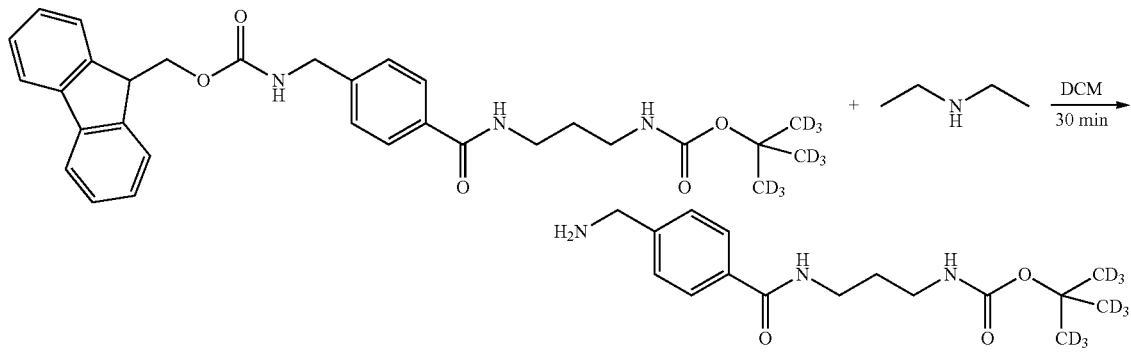

Step 1:

tert-Butyl-d9 alcohol (0.128 mL, 1.20 mmol, 1 eq) and quinoline (0.141 mL, 1.20 mmol, 1 eq) were combined in a dry screw-cap vial with 1 mL of anhydrous dichloromethane. Phenyl chloroformate (0.155 mL, 1.2 mmol, 1 eq) was then added drop-wise. The reaction was allowed to proceed overnight. The resulting d9-tert-butyl phenyl carbonate was purified on silica using a hexane/ethyl acetate gradient up to hexane:ethyl acetate (V:V=1:1). $^1$H NMR 400 MHz (CDCl$_3$) δ 1.54 (9H, s), 6.97-7.50 (5H, m) MS m/z 226.1 (M+Na)$^+$.

Step 2:

The compound synthesized in the previous step 1 (9.3 mL, 50 mmol) was added to a solution of 1,3-diaminopropane (3.7 mL, 50 mmol) in 35 mL EtOH in a 200-mL, single-necked, round-bottomed flask equipped with a stirring bar and a reflux condenser. The reaction mixture was heated gently to reflux overnight ensuring that the temperature was in the range of 80-85° C., resulting in a yellow solution. The reaction mixture was cooled to room temperature and the solution was concentrated to approximately 7-8 mL using a rotary evaporator, which left a yellow solution. Water (50 mL) was added and pH was adjusted to approximately pH 3 by careful addition of aqueous HCl followed by extraction with CH$_2$Cl$_2$ (3×80 mL). The aqueous layer was adjusted to pH 13 by the addition of 2M NaOH and extracted with CH$_2$Cl$_2$ (5×100 mL). The combined organic extracts were concentrated using a rotary evaporator to afford 2.8 g of a yellow oil which crystallized within ~1 h. Yield: 33% MW: 183.2 MS: m/z 184.1 (M+H)$^+$ Step 3:

A solution of Fmoc-4-aminomethyl benzoic acid (0.1494 g, 0.4 mmol, 1 eq) in a 20 mL of anhydrous tetrahydrofuran was cooled to 0° C. on ice. N-(3-Dimethylaminopropyl)-N'-ethylcarbodiimide hydrochloride (0.0844 g, 0.44 mmol, 1.1 eq) and 1-hydroxybenzotiazole (0.0542 g, 0.44 mmol, 1.1 eq) were added, and the suspension was stirred for 30 min at 0° C. A solution of N-d9-Boc-1,3-diaminopropane (0.0732 g, 0.4 mmol, 1 eq) in 4 mL of N,N-dimethylformamide was added drop-wise to the suspension. The reaction mixture was allowed to warm to room temperature and stirred overnight. Then, it was concentrated using a rotary evaporator. The residue was taken up in 200 mL of ethyl acetate and washed with 1M HCl (160 mL), then water (3×160 mL). The organic solvent was evaporated using a rotary evaporator. The solid product was purified by crystallization from isopropyl alcohol to give 0.1513 g compound. Yield: 70% MW=538.3.

Step 4:

A mixture of the Fmoc-protected compound synthesized in Step 3 (0.0807 g, 0.15 mmol) was dissolved in 6 mL of diethylamine (DEA)/dichloromethane mixture (v/v=1:1). The mixture was magnetically stirred until the white colored solution turned yellow (approximately 30 min). The organic solvent was evaporated using a rotary evaporator and the residual mass (yellow oil) was purified by column chromatography (SiO$_2$, particle size 40-63 µm) using stepped gradient of ethyl acetate:methanol (100→80:20), 1% triethylamine. The pertinent fraction was evaporated nn the rotary evaporator to give 0.0250 g of the internal standard. Yield: 53% MW: 316.3. MS: m/z 317.3 (M+H)$^+$; $^1$H-NMR (CDCl$_3$): 1.62 (m, 2H), 3.00 (t, 2H), 3.26 (t, 2H), 3.83 (s, 2H), 7.45 (d, 2H), 7.81 (d, 2H).

Example 2

Simplex PPT1 Assay

C$_{12}$ PPT1 Substrates and Internal Standards

Substrate: N-Acetyl-dodecanoic-thioester of N-Acetyl-ALLPFGC having the structure below:

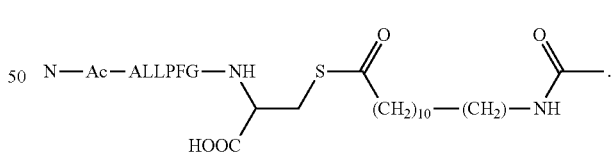

Internal Standard: d3-N-acetyl-dodecanoic acid, [M+H]$^+$ m/z=261.2 having the structure below:

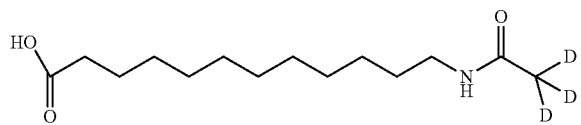 [SMILES: [2H]C([2H])([2H])C(=O)NCCCCCCCCCCCC(=O)O]

Enzymatic product (to be detected in tandem mass spectrometry), [M+H]$^+$ m/z=258.2

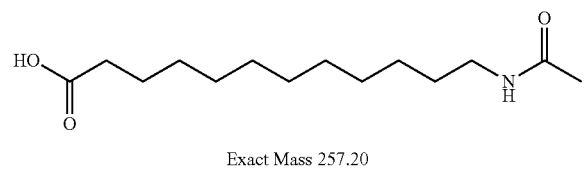 [SMILES: CC(=O)NCCCCCCCCCCCC(=O)O]

Exact Mass 257.20

As shown above, the substrate is N-Acetyl-dodecanoic acid conjugated to an N-acetylated-heptapeptide (N-Ac-ALLPFGC). When cleaved by PPT1, the enzymatic products are the N-acetylated heptapeptide and the N-acetyl-dodecanoic acid, the latter of which is detected in the assay. The internal standard is a heavy atom-labeled N-acetyl-dodecanoic acid, which includes 3 deuterium atoms on the acetyl group.

Assay Protocol

Assay cocktail: a substrate and internal standard stock solution (methanol solution) were pipetted into a vial and dried using a speed vacuum. After all the solvent is removed, the residue was diluted with assay buffer (0.1M phosphate citrate buffer, 0.08% Triton X-100 (or sodium taurocholate), 0.1 mM EDTA (or no EDTA) at pH=6.75) to a final concentration of 0.6 mM (substrate), 30 μM (Internal Standard), and mixed by vortexing.

A 3.2 mm dried blood spot punch was placed into a sample Eppendorf vial. For the blank control, a 3.2 mm filter paper punch was placed in a vial. 30 μL of assay cocktail was added to each vial, which either includes dried blood spot (or filter paper blanks). The Eppendorf vial is shaken at 37° C. for 16 hrs using an orbital shaker (250 rpm)/incubator.

After the incubation, the assay is quenched with 100 μL of methanol/ethyl acetate=50/50 mixture, and then 400 μL of ethyl acetate, then 200 μL of 0.5M NaCl(aq), pipette up and down 10× times to mix well.

The sample tubes were then centrifuged at 3000 rpm for 5 minutes. 200 μL of upper layer solution (organic layer) was removed, and transferred to a new shallow plate. The solvent was evaporated under nitrogen gas flow, the remaining solid was reconstituted with 100 μL LC-MS solvent (55/45 water/acetonitrile with 0.1% formic acid). The solution was mixed up and down about 10 times with a pipettor.

The plate was placed on the autosampler of the LC-MS/MS for isocratic LC-MS/MS. The plate was wrapped with aluminum foil, and the autosampler was held at 8° C. to minimize solvent evaporation.

LC-MS/MS Method

Two LC methods were applicable to this assay.

A. UPLC gradient elution method:

Mobile phase A: water+0.1% formic acid

Mobile phase B: acetonitrile/methanol=50/50+0.1% formic acid

Strong needle wash: acetonitrile+0.1% formic acid

Weak needle wash: water/acetonitrile=90/10+0.1% formic acid

Analytical column and a guard column (Acquity CSH C18; 2.1*50 mm, 1.7 μm; Acquity UPLC CSH C18 VanGuard precolumn; 2.1*5 mm, 1.7 μm; Waters).

Gradient elution: 0 min 60% A, 1.8 min 0% A, 1.88 min 0% A, 1.9 min 60% A, total run time about 2.2 min.

Flow rate: 0.5 mL/min.

Injection volume: 5 μL.

B. HPLC isocratic elution method (same as the 6-plex LC-method)

Mobile phase: 55/45 water/acetonitrile with 0.1% formic acid

Strong needle wash: acetonitrile+0.1% formic acid

Weak needle wash: water/acetonitrile=90/10+0.1% formic acid

The flow rate is 0.4 mL/min.

The LC column was a XSelect CSH C18 (Waters, 130 Å, 3.5 m, 2.1 mm×50 mm, 1/pkg [cat. #186005255]) with a XSelect CSH C18 Sentry Guard cartridge, 130 Å, 3.5 μm, 2.1 mm×10 mm, 2/pkg [186005252] and 2.1×10 mm holder kit for cartridges and guard columns [WAT097958]).

Selective Reaction Monitoring Parameters

Table 5 provides selective reaction monitoring parameters used on a Waters Xevo TQ instrument.

TABLE 5

Selective reaction monitoring parameters.

| Compound name | Parent (m/z) | Daughter (m/z) | Cone voltage | Collision energy |
|---|---|---|---|---|
| PPT1-P N-Ac-C$_{12}$ acid | 258.2 | 198.3 | 15 | 15 |
| PPT1-IS d3-N-Ac-C$_{12}$ acid | 261.2 | 199.4 | 15 | 15 |
| PPT1-Substrate thioester | 1001.5 | 662.3 | 25 | 20 |

LC-MS Data

A representative set of data obtained on a Waters Xevo TQ MS/MS is provided in Table 6.

TABLE 6

Representative data for PPT1 assay.

| Sample name | P Area | IS Area | response | activity (μmol/Lh) |
|---|---|---|---|---|
| Filter paper blank punch | 17897.93 | 231754.5 | 0.077228 | 2.172037 |
| Adult blood punch | 728694.1 | 157080.6 | 4.638982 | 130.4714 |

Activity was calculated as mol product formation per Liter of blood, per hour. The adult blood/nonblood ratio was 65.

The assay was also carried out with recombinant palmitoyl protein thioesterase (Table 7).

TABLE 7

Representative data for recombinant PPT1 assay.

| Sample name | P Area | IS Area | response | activity (μmol/Lh) |
|---|---|---|---|---|
| Assay with 2 μL PBS blank control | 14648.85 | 212972.2 | 0.068783 | 2.063488 |
| Assay with 2 μL recombinant PPT1 enzyme | 253505.2 | 187929.1 | 1.34894 | 40.4682 |

Example 3

TPP1 and MPS Multiplex Assay

Assay buffer: 50 mM ammonium acetate, 5 mM cerium (III) acetate, pH 5.0

Assay cocktail: an assay cocktail was made by adding stock solutions of substrates, internal standards, and NAG-Thiazoline, in methanol, to an Eppendorf (polypropylene) tube or glass vial. The solvent was removed with a stream of oil-free nitrogen or in a centrifugal concentrator under vacuum. The assay buffer was then added and the mixture was mixed on a vortex mixer until the solution becomes clear. The final assay cocktail has 0.2 mM TPP-1 substrate, 1 mM MPS-II substrate, 0.5 mM MPS-IIIB substrate, 1 mM MPS-IVA substrate, 1 mM MPS-VI substrate, and 0.5 mM MPS-VII substrate, 15 µM TPP-1 internal standard, 10 µM MPS-II internal standard, 10 µM MPS-IIIB internal standard, 7.5 µM MPS-IVA internal standard, 10 µM MPS-VI internal standard, and 10 µM MPS-VII internal standard, 100 µM NAG-thiazoline.

Assay Procedure

To each well in a 96-well assay plate containing a single 3 mm DBS punch was added 30 uL of assay cocktail. The plate was sealed with adhesive sealing film and incubated by shaking at 37° C. for 16 hrs.

After incubation, the assay was quenched by adding 100 µL of 50:50 methanol:ethyl acetate, mixed up and down 4-5 times with a pipettor.

400 µL of ethyl acetate was added. Then 200 µL of 0.5 M NaCl in water was added. The mixture was mixed up and down about 10 times with a pipettor. The mixture was then covered with a silicone mat or an adhesive film. The mixture was centrifuged for about 5 min at 3000 RPM at room temperature to separate the solvent layers.

200 µL of top layer (ethyl acetate layer) was removed to a new shallow well plate using a pipettor. The solvent was removed under oil-free nitrogen or air at room temperature. 100 µL of LC solvent (55/45 water/acetonitrile with 0.1% formic acid) was then added and the mixture was mixed up and down about 10 times with a pipettor. The plate was placed on the autosampler of the LC-MS/MS for isocratic LC-MS/MS.

LC-MS

LC: The LC column was an XSelect CSH C18 (Waters, 130 Å, 3.5 µm, 2.1 mm×50 mm, 1/pkg [cat. #186005255]) with an XSelect CSH C18 Sentry Guard Cartridge, 130 Å, 3.5 µm, 2.1 mm×10 mm. The mobile phase was 55/45 water/acetonitrile with 0.1% formic acid, at a flow rate 0.4 mL/min. The weak needle wash was $H_2O$/acetonitrile 90:10 with 0.1% formic acid, and the strong needle wash was 100% acetonitrile with 0.1% formic acid.

Selective Reaction Monitoring Transitions

The selective reaction monitoring transitions for the TPP1 and MPS products, and the TPP1 and MPS internal standards (int. std.) are provided below.

TABLE 8

Selective reactive monitoring transitions.

| Analytes | SRM transitions (precursor m/z > product m/z) | |
|---|---|---|
| MPS-II product | 644.32 | 359.23 |
| MPS-II int. std. | 649.35 | 364.26 |
| MPS-IIIB product | 420.20 | 311.20 |
| MPS-IIIB int. std. | 423.20 | 314.20 |
| MPS-IVA product | 685.38 | 373.25 |
| MPS-IVA int. std. | 690.41 | 378.28 |
| MPS-VI product | 657.35 | 345.21 |
| MPS-VI int. std. | 662.38 | 350.25 |
| MPS-VII product | 434.35 | 325.30 |
| MPS-VII int. std. | 441.35 | 332.20 |
| TPP 1 product | 350.25 | 250.25 |
| TPP 1 int. std. | 359.30 | 251.20 |

Representative data obtained on a Waters Xevo TQ MS/MS are provided in Table 9.

TABLE 9

Representative data for multiplex assay.

| Sample | LSD | Product Peak Area | Int. Std. Peak Area | P/IS ratio | Activity (µmol/Lh) | Analytical Range[1] |
|---|---|---|---|---|---|---|
| filter paper punch | MPS II | 58 | 11894 | 0.005 | 0.029 | 837.7 |
| Blood punch | MPS II | 198100 | 48383 | 4.107 | 24.066 | |
| filter paper punch | MPS IIIB | 195 | 169230 | 0.001 | 0.007 | 1002.4 |
| Blood punch | MPS IIIB | 187159 | 162908 | 1.151 | 6.745 | |
| filter paper punch | MPS IVA | 71 | 192835 | 0.000 | 0.002 | 3448.4 |
| Blood punch | MPS IVA | 304702 | 239735 | 1.270 | 5.582 | |
| filter paper punch | MPS VI | 38 | 80158 | 0.000 | 0.003 | 6659.9 |
| Blood punch | MPS VI | 286072 | 91599 | 3.119 | 18.276 | |
| filter paper punch | TPP 1 | 1064 | 247337 | 0.004 | 0.038 | 494.8 |
| Blood punch | TPP 1 | 615777 | 288861 | 2.131 | 18.729 | |
| filter paper punch | MPS VII | 13491 | 1430771 | 0.009 | 0.053 | 848.6 |
| Blood punch | MPS VII | 8704512 | 1133911 | 7.678 | 44.988 | |

[1]The analytical range is the P/IS ratio observed with the blood punch sample divided by the P/IS observed with the filter paper blank (no blood).

While illustrative embodiments have been illustrated and described, it will be appreciated that various changes can be made therein without departing from the spirit and scope of the disclosure.

The invention claimed is:

1. A method for assaying for a lysosomal enzyme associated with a lysosomal storage disease, comprising:
   (a) contacting a sample with an aqueous solution to provide a solution comprising one or more lysosomal enzymes;
   (b) contacting the one or more lysosomal enzymes in solution with one or more lysosomal enzyme substrates, and incubating the substrates with the lysosomal enzymes for a time sufficient to provide a solution comprising one or more enzyme products for the one or more lysosomal enzymes present in the sample, wherein the enzyme substrate comprises a compound of Formula (TPP1-S1) and/or Formula (PPT1-S1):

$$P_3\text{—}P_2\text{—}P_1\text{—}NH\text{—}G_1\text{—}X_A\text{—}G_2\text{—}X_B\text{—}Prot, \quad \text{(TPP1-S1)}$$

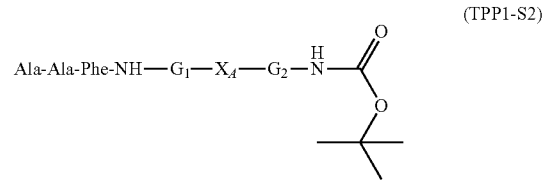

(PPT1-S1)

wherein in the compound of Formula (TPP1-S1),
$P_3$ is an achiral amino acid residue, a D-amino acid residue, or a L-amino acid residue;
$P_2$ is an amino acid residue selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, L-Lys, D-Asn, L-Asn, D-Asp, L-Asp, D-Arg, L-Arg, D-His, and L-His;
$P_1$ is an amino acid residue selected from D-Phe, L-Phe, D-Leu, L-Leu, D-Nle, L-Nle, D-Tyr, L-Tyr, D-Glu, L-Glu, D-Trp, L-Trp, D-Asp, L-Asp, D-Gln, L-Gln, D-Ala, L-Ala, D-Ser, L-Ser, D-Lys, L-Lys, D-Arg, L-Arg, D-Asn, L-Asn, D-His, L-His, D-Val, L-Val, D-Ile, L-Ile, D-Thr, L-Thr, Gly, D-Pro, and L-Pro;
wherein $P_3$ is located at a N-terminus of the $P_3$-$P_2$-$P_1$ moiety, $P_1$ is located at a C-terminus of the $P_3$-$P_2$-$P_1$ moiety;
$G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;
$X_A$ is a first linking functionality linking $G_1$ to $G_2$ selected from a bond, amide, thioamide, sulfonamide, ether, sulfide, ureido, thioureido, and ester;
$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen; and
$X_B$ is a second linking functionality linking $G_2$ to Prot selected from a bond, NH, amide, thioamide, sulfonamide, ether, sulfide, ureido, thioureido, and ester; and
Prot is a protecting group that is capable of fragmenting by one dominant pathway at an efficiency of greater than 5% to provide a residual enzyme product fragment that is detectable by mass spectrometry; and
wherein in the compound of Formula (PPT1-S1),
$R_4$ is selected from a peptide, a polymer, a polysaccharide, an aromatic hydrocarbon group, and an aliphatic hydrocarbon group;
W is selected from H and NHCO—$C_1$-$C_6$ alkyl; and
Y is a $C_2$-$C_{19}$ alkylene; and
(c) determining the quantities of the one or more enzyme products.

2. The method of claim 1, wherein $X_A$ is an amide.

3. The method of claim 1, wherein $X_B$ is selected from NH and an amide.

4. The method of claim 1, wherein $P_3$ is selected from D-Ala, L-Ala, D-Arg, L-Arg, D-Asn, L-Asn, D-Asp, L-Asp, D-Cys, L-Cys, D-Glu, L-Glu, D-Gln, L-Gln, Gly, D-His, L-His, D-Ile, L-Ile, D-Leu, L-Leu, D-Lys, L-Lys, D-Met, L-Met, D-Phe, L-Phe, D-Pro, L-Pro, D-Ser, L-Ser, D-Thr, L-Thr, D-Trp, L-Trp, D-Tyr, L-Tyr, D-Val, and L-Val.

5. The method of claim 1, wherein $P_2$ is selected from D-Nle, L-Nle, D-Pro, L-Pro, D-Ala, L-Ala, D-Phe, L-Phe, D-Tyr, L-Tyr, D-Trp, L-Trp, D-Ile, L-Ile, D-Val, L-Val, D-Thr, L-Thr, D-Glu, L-Glu, D-Ser, L-Ser, D-Leu, L-Leu, Gly, D-Gln, L-Gln, D-Lys, and L-Lys.

6. The method of claim 1, wherein $P_1$ is selected from D-Phe, L-Phe, D-Leu, L-Leu, D-Nle, L-Nle, D-Tyr, L-Tyr, D-Glu, L-Glu, D-Trp, L-Trp, D-Asp, L-Asp, D-Gln, L-Gln, D-Ala, L-Ala, D-Ser, L-Ser, D-Lys, and L-Lys.

7. The method of claim 1, wherein
$P_3$ is an amino acid residue selected from L-Ala, L-Arg, L-Asn, L-Asp, L-Cys, L-Glu, L-Gln, Gly, L-His, L-Ile, L-Leu, L-Lys, L-Met, L-Phe, L-Pro, L-Ser, L-Thr, L-Trp, L-Tyr, and L-Val;
$P_2$ is an amino acid residue selected from L-Nle, L-Pro, L-Ala, L-Phe, and L-Tyr;
$P_1$ is an amino acid residue selected from L-Phe, L-Leu, L-Nle, and L-Tyr;
$G_1$ is $(CH_2)_q$—Ar,
wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, amino; and
q is an integer from 0 to 4;
$X_A$ is amide;
$G_2$ is $(CH_2)_p$,
wherein p is an integer from 3 to 20;
$X_B$ is selected from NH and amide; and
Prot is selected from C(O)O$C_1$-$C_6$ alkyl, $C_1$-$C_6$ alkoxy, $C_1$-$C_6$ alkyl, di-$C_1$-$C_6$ alkylamino, and $C_1$-$C_6$ alkylamino.

8. The method of claim 1, wherein
(a) the substrate of Formula (TPP1-S1) is a compound of Formula (TPP1-S2):

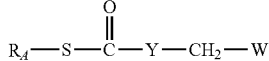

(TPP1-S2)

wherein
$G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;
$X_A$ is a first linking functionality linking $G_1$ to $G_2$ selected from a bond, amide, thioamide, sulfonamide, ether, sulfide, ureido, thioureido, and ester; and
$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen, or (b) wherein the substrate of Formula (TPP1-S1) is a compound of Formula (TPP1-S3):

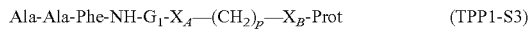

Ala-Ala-Phe-NH-$G_1$-$X_A$—$(CH_2)_p$—$X_B$-Prot          (TPP1-S3)

$G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $(CH_2)_p$ selected from a bond, amide, thioamide, sulfonamide, ether, sulfide, ureido, thioureido, and ester;

$X_B$ is a second linking functionality linking $(CH_2)_p$ to Prot selected from a bond, NH, amide, thioamide, sulfonamide, ether, sulfide, ureido, thioureido, and ester;

Prot is a protecting group that is capable of fragmenting by one dominant pathway at an efficiency of greater than 5% to provide a residual enzyme product fragment that is detectable by mass spectrometry; and p is an integer from 3 to 20, or (c) wherein the substrate of Formula (TPP1-S1) is a compound of Formula (TPP1-S4):

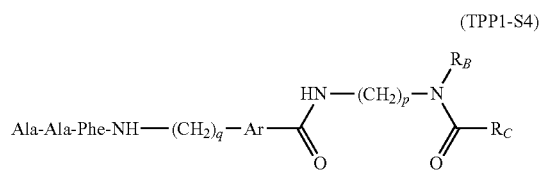

(TPP1-S4)

wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, amino;

$R_B$ is selected from H, $C_1$-$C_6$ alkyl, and $C_1$-$C_6$ haloalkyl;

$R_C$ is selected from $C_1$-$C_6$ alkoxy, $C_1$-$C_6$ alkyl, di-$C_1$-$C_6$ alkylamino, and $C_1$-$C_6$ alkylamino;

p is an integer from 3 to 6; and q is an integer from 0 to 4, or (d) wherein the substrate of Formula (TPP1-S1) is a compound of Formula (TPP1-S5):

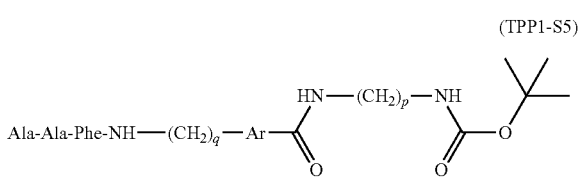

(TPP1-S5)

wherein Ar is selected from a $C_5$-$C_6$ arylene and a $C_2$-$C_6$ heteroarylene, each optionally substituted with 1, 2, 3, or 4 substituents each independently selected from $C_1$-$C_6$ alkyl, $C_1$-$C_6$ haloalkyl, halo, and amino;

p is an integer from 3 to 6; and q is an integer from 0 to 4.

9. The method of claim 1, wherein $R_A$ is N-acetyl-Ala-Ala-Ala-Pro-Phe-Gly-Cys, and S in Formula (PPT1-S1) is a sulfur on the Cys side chain.

10. The method of claim 1, wherein W is NHCO—$C_1$-$C_6$ alkyl.

11. The method of claim 1, wherein Y is a $C_3$-$C_{11}$ alkylene.

12. The method of claim 1, wherein the one or more of the enzyme products comprise a compound of Formula (TPP1-P1) and/or (PPT1-P1),

$NH_2$—$G_1$—$X_A$—$G_2$—$X_B$—Prot,          (TPP1-P1)

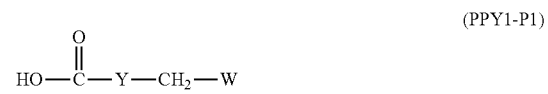

(PPY1-P1)

$$HO-\overset{O}{\underset{\|}{C}}-Y-CH_2-W$$

wherein in the compound of Formula (TPP1-P1), $G_1$ is a first linker comprising 2-20 carbon atoms in which one or more carbon atoms may be replaced with a heteroatom selected from N, O, and S, and/or one or more of carbon atoms may be substituted with a $C_1$-$C_6$ alkyl group, $C_1$-$C_6$ haloalkyl, halo, or amino;

$X_A$ is a first linking functionality linking $G_1$ to $G_2$ selected from a bond, amide, thioamide, sulfonamide, ether, sulfide, ureido, thioureido, and ester;

$G_2$ is a second linker comprising 2-20 carbon atoms in which one or more carbon atoms may be replaced with a heteroatom selected from N, O, and S, and/or one or more of carbon atoms may be substituted with a $C_1$-$C_6$ alkyl group or halogen;

$X_B$ is a second linking functionality linking $G_2$ to Prot selected from a bond, NH, amide, thioamide, sulfonamide, ether, sulfide, ureido, thioureido, and ester; and Prot is a protecting group that is capable of fragmenting by one dominant pathway at an efficiency of greater than 5% to provide a residual enzyme product fragment that is detectable by mass spectrometry; and wherein in the compound of Formula (PPT1-P1), W is selected from H and NHCO—$C_1$-$C_6$ alkyl; and Y is a $C_2$-$C_{19}$ alkylene.

13. The method of claim 1, wherein the one or more lysosomal enzymes comprises an enzyme selected from tripeptidyl peptidase 1 and palmitoyl protein thioesterase 1.

14. The method of claim 1, wherein in step (b), the one or more lysosomal enzyme substrates further comprises a compound having a carbohydrate moiety and an aglycone moiety and having Formula (MPS-S):

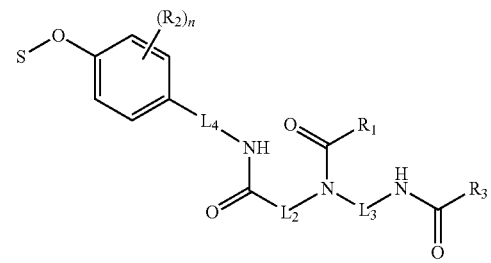

(MPS-S)

wherein S is the carbohydrate moiety that when covalently coupled to the aglycone moiety provides a substrate for an enzyme selected from the group consisting of:

(i) alpha-L-iduronidase;
(ii) iduronate 2-sulfatase;
(iii) heparan N-sulfatase;

(iv) N-acetyl-alpha-D-glucosaminidase;
(v) N-acetylgalactosamine 6-sulfate-sulfatase;
(vi) N-acetylgalactosamine 4-sulfate-sulfatase; and
(vii) beta-glucuronidase;

$L_2$ is a linker comprising 1-20 carbon atoms in which one or more carbon atoms may be replaced with a heteroatom selected from N, O, and S, and/or one or more of carbon atoms may be substituted with a $C_1$-$C_6$ alkyl group or halogen;

$L_3$ is a linker comprising 1-20 carbon atoms in which one or more carbon atoms may be replaced with a heteroatom selected from N, O, or S, and/or one or more of carbon atoms may be substituted with a $C_1$-$C_6$ alkyl group or halogen;

$L_4$ is optional and when present is a linker comprising 1-20 carbon atoms in which one or more carbon atoms may be replaced with a heteroatom selected from N, O, or S), and/or one or more of carbon atoms may be substituted with a $C_1$-$C_6$ alkyl group or halogen;

$R_1$ is a $C_1$-$C_{10}$ alkyl group or a $C_1$-$C_{10}$ alkoxy group;

$R_2$ at each occurrence is independently selected from a $C_1$-$C_{10}$ alkyl group, a $C_1$-$C_{10}$ alkoxy group, halogen, nitro, C(=O)NHR, and C(=O)OR, where R is $C_1$-$C_8$ alkyl group;

$R_3$ is a $C_1$-$C_{10}$ alkyl group or a substituted or unsubstituted $C_6$-$C_{10}$ aryl group; and n is 0, 1, 2, 3, or 4.

15. The method of claim 14, further comprising contacting the one or more enzyme products with a glycohydrolase to provide glycohydrolase enzyme products.

16. The method of claim 1, further comprising adding an inhibitor to block endogenous glycohydrolase enzymatic activity that acts on a substrate for one or more of an enzyme selected from the group consisting of:
    (a) N-acetylgalactosamine 6-sulfate-sulfatase; and
    (b) N-acetylgalactosamine 4-sulfate-sulfatase.

17. The method of claim 1, further comprising adding an internal standard for each lysosomal enzyme to be analyzed before, after, or simultaneously with contacting the lysosomal enzymes with the one or more substrates.

18. The method of claim 1 wherein the sample is a blood or tissue sample.

19. The method of claim 1, wherein determining the quantities of the one or more enzyme products comprises mass spectrometric analysis or fluorescence analysis.

20. The method of claim 1, further comprising using the quantities of the one or more enzyme products to determine whether the sample is from a candidate for treatment for a condition associated with one or more lysosomal storage diseases.

\* \* \* \* \*

UNITED STATES PATENT AND TRADEMARK OFFICE
CERTIFICATE OF CORRECTION

PATENT NO. : 10,788,499 B2  
APPLICATION NO. : 15/744736  
DATED : September 29, 2020  
INVENTOR(S) : Gelb et al.

Page 1 of 1

It is certified that error appears in the above-identified patent and that said Letters Patent is hereby corrected as shown below:

In the Claims

| Column | Line |   |
|--------|------|---|
| 102    | 12   | "(PPY1-P1)" to -- (PPT1-P1) -- |
| 103    | 25   | "nitro, C" to -- nitro, -C -- |
| 103    | 25   | "and C" to -- and –C -- |

Signed and Sealed this  
Fifteenth Day of December, 2020

Andrei Iancu  
*Director of the United States Patent and Trademark Office*